United States Patent
Ross et al.

(10) Patent No.: US 11,311,624 B2
(45) Date of Patent: Apr. 26, 2022

(54) INHIBITORS OF MEK/PI3K, JAK/MEK, JAK/PI3K/MTOR AND MEK/PI3K/MTOR BIOLOGICAL PATHWAYS AND METHODS FOR IMPROVING LYMPHATIC UPTAKE, BIOAVAILABILITY, AND SOLUBILITY OF THERAPEUTIC COMPOUNDS

(71) Applicant: THE REGENTS OF THE UNIVERSITY OF MICHIGAN, Ann Arbor, MI (US)

(72) Inventors: Brian D. Ross, Ann Arbor, MI (US); Marcian Van Dort, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/637,305

(22) PCT Filed: Aug. 8, 2018

(86) PCT No.: PCT/US2018/045703
§ 371 (c)(1),
(2) Date: Feb. 7, 2020

(87) PCT Pub. No.: WO2019/032640
PCT Pub. Date: Feb. 14, 2019

(65) Prior Publication Data
US 2020/0164081 A1 May 28, 2020

Related U.S. Application Data

(60) Provisional application No. 62/544,332, filed on Aug. 11, 2017.

(51) Int. Cl.
| | |
|---|---|
| *A61K 47/60* | (2017.01) |
| *A61K 47/54* | (2017.01) |
| *C07C 259/10* | (2006.01) |
| *C07D 239/48* | (2006.01) |
| *C07D 401/04* | (2006.01) |
| *C07D 401/14* | (2006.01) |
| *C07D 403/04* | (2006.01) |
| *C07D 471/04* | (2006.01) |

(52) U.S. Cl.
CPC .............. *A61K 47/60* (2017.08); *A61K 47/54* (2017.08); *C07C 259/10* (2013.01); *C07D 239/48* (2013.01); *C07D 401/04* (2013.01); *C07D 401/14* (2013.01); *C07D 403/04* (2013.01); *C07D 471/04* (2013.01)

(58) Field of Classification Search
None
See application file for complete search history.

(56) References Cited

U.S. PATENT DOCUMENTS

| | | |
|---|---|---|
| 7,897,792 B2 | 3/2011 | Iikura et al. |
| 9,284,315 B2 | 3/2016 | Wu et al. |
| 9,611,258 B2 | 4/2017 | Ross et al. |
| 2010/0249099 A1 | 9/2010 | Rewcastle et al. |
| 2011/0009405 A1 | 1/2011 | Rewcastle et al. |
| 2011/0053907 A1 | 3/2011 | Rewcastle et al. |

FOREIGN PATENT DOCUMENTS

| | | |
|---|---|---|
| WO | WO-2006/122806 A2 | 11/2006 |
| WO | WO-2009/018238 A1 | 2/2009 |
| WO | WO-2010/003816 A1 | 1/2010 |
| WO | WO-2012/068106 A2 | 5/2012 |
| WO | WO-2014/164942 A1 | 10/2014 |
| WO | WO-2018/009638 A1 | 1/2018 |

OTHER PUBLICATIONS

Spicer et al. "4-Anilino-5-carboxamido-2-pyridone Derivatives as Noncompetitive Inhibitors of Mitogen-Activated Protein Kinase Kinase" J. Med. Chem. 2007, vol. 50, No. 21, pp. 5090-5102.*
Anighoro et al., Polypharmacology: challenges and opportunities in drug discovery, J. Med. Chem., 57(19):7874-87 (2014).
Bakhru et al., Oral delivery of proteins by biodegradable nanoparticles. Adv Drug Deliv Rev 65(6): 811-21 (2013).
Caliph et al., Effect of short-, medium-, and long-chain fatty acid-based vehicles on the absolute oral bioavailability and intestinal lymphatic transport of halofantrine and assessment of mass balance in lymph-cannulated and non-cannulated rats. J Pharm Sci 89(8): 1073-84 (2000).
Charman, Estimating the maximum potential for intestinal lymphatic transport of lipophilic drug molecules. Int. J. Pharm 34:175-8 (1986).
Choo et al., The role of lymphatic transport on the systemic bioavailability of the Bcl-2 protein family inhibitors navitoclax (ABT-263) and ABT-199. Drug Metab Dispos 42(2): 207-12 (2014).
Doddapaneni et al., A three-drug nanoscale drug delivery system designed for preferential lymphatic uptake for the treatment of metastatic melanoma, J. Control. Release, 220(Pt. A):503-14 (Dec. 2015).
Engelman et al., Effective use of PI3K and MEK inhibitors to treat mutant Kras G12D and PIK3CA H1047R murine lung cancers, Nat Med., 14(12):1351-6 (Dec. 2008).
Faisal et al., A novel lipid-based solid dispersion for enhancing oral bioavailability of Lycopene—in vivo evaluation using a pig model. Int J Pharm 453(2): 307-14 (2013).

(Continued)

*Primary Examiner* — Joseph R Kosack
(74) *Attorney, Agent, or Firm* — Marshall, Gerstein & Borun LLP

(57) ABSTRACT

Inhibitors of mTOR, MEK, JAK and PI3K and compositions containing the same are disclosed. Methods of using the inhibitors in the treatment of a variety of diseases and conditions wherein inhibition of one or more of mTOR, MEK, JAK and PI3K provides a benefit also are disclosed. Methods of using chemical attachment moieties and linkers for the purposes of modifying compound solubility and/or lymphatic absorption are also disclosed.

3 Claims, 7 Drawing Sheets

(56) References Cited

OTHER PUBLICATIONS

Florence, Nanoparticle uptake by the oral route: Fulfilling its potential? Drug Discov Today Technol 2(1): 75-81 (2005).
Gershkovich et al., The role of molecular physicochemical properties and apolipoproteins in association of drugs with triglyceride-rich lipoproteins: in-silico prediction of uptake by chylomicrons. J Pharm Pharmacol 61(1): 31-39 (2009).
Gershkovich et al., Uptake of lipophilic drugs by plasma derived isolated chylomicrons: linear correlation with intestinal lymphatic bioavailability. Eur J Pharm Sci 26(5): 394-404 (2005).
Han et al., (2014). Targeted delivery of a model immunomodulator to the lymphatic system: comparison of alkyl ester versus triglyceride mimetic lipid prodrug strategies. J Control Release 177: 1-10 (2014).
Hauss et al., Lipid-based delivery systems for improving the bioavailability and lymphatic transport of a poorly water-soluble LTB4 inhibitor. J Pharm Sci 87(2): 164-9 (1998).
Holm et al., Successful in silico predicting of intestinal lymphatic transfer. Int J Pharm 272(1-2): 189-93 (2004).
Hopkins et al., The role of ligand efficiency metrics in drug discovery. Nat Rev Drug Discov 13(2): 105-21 (2014).
Hu et al., Glyceride-Mimetic Prodrugs Incorporating Self-Immolative Spacers Promote Lymphatic Transport, Avoid First-Pass Metabolism, and Enhance Oral Bioavailability. Angew Chem Int Ed Engl 55(44): 13700-5 (2016).
International Application No. PCT/US2018/045703, International Search Report and Written Opinion, dated Jan. 25, 2019.
Karaman et al., Mechanisms of lymphatic metastasis. J Clin Invest 124(3): 922-8 (2014).
Khoo et al., Intestinal lymphatic transport of halofantrine occurs after oral administration of a unit-dose lipid-based formulation to fasted dogs. Pharm Res 20(9): 1460-5 (2003).
Kunisawa et al., Gut-associated lymphoid tissues for the development of oral vaccines. Adv Drug Deliv Rev 64(6): 523-30 (2012).
Lambert, Rationale and applications of lipids as prodrug carriers. Eur J Pharm Sci 11 Suppl 2: S15-27 (2000).
Lawless et al., Exploring the impact of drug properties on the extent of intestinal lymphatic transport—in vitro and in vivo studies. Pharm Res 32(5): 1817-1829 (2015).
Leeson et al., The influence of drug-like concepts on decision-making in medicinal chemistry. Nat Rev Drug Discov 6(11): 881-890 (2007).
Li et al., Synthesis and biological evaluation of RGD-conjugated MEK1/2 kinase inhibitors for integrin-targeted cancer therapy, Molecules, 18(11):13957-78 (Nov. 2013).
Lindenberg et al., Classification of orally administered drugs on the World Health Organization Model list of Essential Medicines according to the biopharmaceutics classification system. Eur J Pharm Biopharm 58(2): 265-278 (2004).
Lipinski et al., Experimental and computational approaches to estimate solubility and permeability in drug discovery and development settings, Adv. Drug Deliv. Rev., 46(1-3):3-26 (2001).
Lu et al., Biomimetic reassembled chylomicrons as novel association model for the prediction of lymphatic transportation of highly lipophilic drugs via the oral route. Int J Pharm 483(1-2): 69-76 (2015).
Ma et al., Polyethylene glycol 400 (PEG400) affects the systemic exposure of oral drugs based on multiple mechanisms: taking berberine as an example. RSC Adv 7: 2435-2442 (2017).
Myers et al., Factors affecting the lymphatic transport of penclomedine (NSC-338720), a lipophilic cytoxic drug-comparison to DDT and hexachlorobenzene. Int. J. Pharm. 80: 51-62 (1992).
O'Driscoll, Lipid-based formulations for intestinal lymphatic delivery. Eur J Pharm Sci 15(5): 405-415 (2002).
Oprea et al., Is there a difference between leads and drugs? A historical perspective. J Chem Inf Comput Sci 41(5): 1308-1315 (2001).
Paliwal et al., Engineered chylomicron mimicking carrier emulsome for lymph targeted oral delivery of methotrexate. Int J Pharm 380(1-2): 181-188 (2009).
Porter et al., Lymphatic transport of halofantrine in the conscious rat when administered as either the free base or the hydrochloride salt: effect of lipid class and lipid vehicle dispersion. J Pharm Sci 85(4): 357-361 (1996).
Rautio et al., Prodrugs: design and clinical applications. Nat Rev Drug Discov 7(3): 255-270 (2008).
Reddy et al., Polypharmacology: drug discovery for the future. Expert Rev Clin Pharmacol 6(1): 41-47 (2013).
Shackleford et al., Contribution of lymphatically transported testosterone undecanoate to the systemic exposure of testosterone after oral administration of two andriol formulations in conscious lymph duct-cannulated dogs. J Pharmacol Exp Ther 306(3): 925-933 (2003).
Sugihara et al., Studies on intestinal lymphatic absorption of drugs. I. Lymphatic absorption of alkyl ester derivatives and alpha-monoglyceride derivatives of drugs. J Pharmacobiodyn 11(5): 369-376 (1988).
Sugihara et al., Studies on intestinal lymphatic absorption of drugs. II. Glyceride prodrugs for improving lymphatic absorption of naproxen and nicotinic acid. J Pharmacobiodyn 11(8): 555-562 (1988).
Trevaskis et al., A mouse model to evaluate the impact of species, sex, and lipid load on lymphatic drug transport. Pharm Res 30(12): 3254-3270 (2013).
Trevaskis et al., From sewer to saviour—targeting the lymphatic system to promote drug exposure and activity. Nat Rev Drug Discov 14(11): 781-803 (2015).
Trevaskis et al., Intestinal lymphatic transport enhances the postprandial oral bioavailability of a novel cannabinoid receptor agonist via avoidance of first-pass metabolism. Pharm Res 26(6): 1486-1495 (2009).
Trevaskis et al., Lipid-based delivery systems and intestinal lymphatic drug transport: a mechanistic update. Adv Drug Deliv Rev 60(6): 702-716 (2008).
Trevaskis et al., The mechanism of lymphatic access of two cholesteryl ester transfer protein inhibitors (CP524,515 and CP532,623) and evaluation of their impact on lymph lipoprotein profiles. Pharm Res 27(9): 1949-1964 (2010).
Turecek et al., PEGylation of Biopharmaceuticals: A Review of Chemistry and Nonclinical Safety Information of Approved Drugs. J Pharm Sci 105(2): 460-475 (2016).
Van Dort et al., Discovery of Bifunctional Oncogenic Target Inhibitors against Allosteric Mitogen-Activated Protein Kinase (MEK1) and Phosphatidylinositol 3-Kinase (PI3K), J. Med. Chem., 59(6):2512-22 (Mar. 2016).
Van Dort et al., Structure-Guided Design and Initial Studies of a Bifunctional MEK/PI3K Inhibitor (ST-168), ACS Med. Chem. Lett., 8(8):808-13 (Jul. 2017).
Van Witteloostuijn et al., Half-Life Extension of Biopharmaceuticals using Chemical Methods: Alternatives to PEGylation. ChemMedChem 11(22): 2474-2495 (2016).
Yanez et al., Intestinal lymphatic transport for drug delivery. Adv Drug Deliv Rev 63(10-11): 923-942 (2011).

* cited by examiner

INHIBITORS OF MEK/PI3K, JAK/MEK, JAK/PI3K/MTOR AND MEK/PI3K/MTOR BIOLOGICAL PATHWAYS AND METHODS FOR IMPROVING LYMPHATIC UPTAKE, BIOAVAILABILITY, AND SOLUBILITY OF THERAPEUTIC COMPOUNDS

CROSS-REFERENCE TO RELATED APPLICATIONS

This application is the U.S. National Stage application of International Patent Application No. PCT/US2018/045703, filed Aug. 8, 2018, which claims the benefit of U.S. Provisional Patent Application No. 62/544,332, filed Aug. 11, 2017.

STATEMENT OF GOVERNMENTAL INTEREST

This invention was made with government support under grants CA197701 and CA085878 awarded by the U.S. National Institutes of Health. The government has certain rights in the invention.

FIELD OF THE INVENTION

The present invention relates to inhibitors, including monofunctional inhibitors, bifunctional inhibitors, trifunctional inhibitors, and tetrafunctional inhibitors, of mTOR, MEK, JAK and PI3K, and to therapeutic methods of treating conditions and diseases wherein inhibition of one or more of mTOR, MEK, JAK and PI3K provides a benefit. The present inhibitors are useful as agents for cancer therapy, either alone or in combination with radiation, immunotherapy and/or chemotherapeutics.

The present inhibitors demonstrate an improved lymphatic-directed absorption of therapeutic drugs, while increasing the solubility and bioavailability of a therapeutic drug by covalent attachment of a lymphatic-directing chemical moiety that alters the physiochemical properties of the parent therapeutic drug. Nonlimiting embodiments include mono-attachment of a therapeutic drug on a single end of a lymphatic-directing functional moiety, attachment of a therapeutic drug to each end of the moiety, attachment of multiple therapeutic drugs using branched/star moieties (e.g., multiple moieties emanating from a central core group), and combination moieties (e.g., multiple chains grafted onto a polymer backbone) to provide multifunctional activities.

BACKGROUND OF THE INVENTION

Oral bioavailability of a therapeutic drug is limited when the compound has poor aqueous solubility (Log P>5) and poor dissolution, low intestinal permeability, or rapid metabolic degradation. Compounds that have a high affinity for an intended cellular target in isolated enzyme assays may have negligible solubility, thus bioavailability is limited and drug suitability compromised. Efforts have been undertaken to improve the uptake of a drug through delivery in an excipient material that improves solubilization of the drug. However, the physicochemical and biochemical processes by which lipid excipients enhance the oral delivery of poorly-absorbed drugs are complex.

Lipid formulations have been used to improve the bioavailability of poorly-soluble drugs. However, many potential drugs have been abandoned at the research stage due to poor solubility and lack of suitable absorption. Formulations can assist solubilizing a drug, i.e., an active pharmaceutical ingredient (API), in the aqueous environment of the digestive tract through emulsification and micellization processes. Lipid formulations therefore are used to improve bioavailability of poorly soluble drugs by maintaining the drug in a solubilized state until the drug reaches the site of absorption.

Following oral administration, the predigested contents of the stomach empty into the duodenum, where it combines with salts and surfactants in bile. This process aids in dispersion of hydrophobic lipid structures within the water-rich environment of the small intestine. For orally delivered drugs dissolved using lipid formulations, the components undergo digestion and the lipids are released at the outer layer of the mixed micelles. Lipases convert the components to free fatty acids. As emulsification continues, a subsequent reduction in lipid droplet size occurs which results in an increased surface area facilitating additional lipolytic action by the lipases. The resulting micelles and lamellar structures trigger a further increase in solubilization capacity. While a lipid formulation may have the necessary constituents needed to self-emulsify in the gut in the presence of endogenous bile salt and pancreatic secretions, some excipients are able to undergo self-emulsification and can singly solubilize the API. Additionally, combinations of excipients may be used to provide for API-specific mixtures in order to customize the solubilization needs of the API. There also is a significant focus on achieving supersaturation of the API in the gastrointestinal (GI) lumen as a key mechanism for enhancing gut permeability. The development of lipid-based excipient formulations has evolved to assist the dissolution and absorption of drugs that have low solubility and high Log P values.

Pathways for drug absorption following oral delivery are via the blood or lymphatic system with un-solubilized material passing through the digestive tract into the feces. In general, fatty acids having hydrocarbon chains less than 12 carbon atoms tend to bind to albumin, which renders them water soluble. As a result, these fatty acids passively diffuse through epithelial cells lining of the intestine and are subsequently taken up by the blood stream through the portal vein prior to being transported to the liver. Fatty acids having a chain length of 14 carbons or longer can be substrates for transporting proteins into the cells due to their hydrophobicity, where they can be resynthesized into lipoproteins (i.e., chylomicrons) for uptake by the lymphatic route. Unsaturated long-chain fatty acids (LCFA), in particular, stimulate chylomicron secretion and increase lymphatic uptake, thus enhancing the bioavailability of certain drugs, such as saquinavir, ontazolast, and halofantrine, through preferential absorption via the lymphatic transport system with a consequent reduction in first-pass metabolism of the API by the liver (Hauss, Fogal et al. 1998, O'Driscoll 2002). Because absorption by the lymph system bypasses the liver, co-formulation of therapeutic drugs with unsaturated LCFAs can improve the activity of drugs that are susceptible to extensive metabolism in the liver. A general principle is that an enhanced lymphatic absorption following oral delivery for highly lipophilic drugs (c Log P>5) may be achieved if a compound is found to have high solubility in triglycerides (Cs>50 mg/mL). Therefore, compounds possessing these properties are considered potential API candidates for lymphatic absorption.

Lipid excipients traditionally enhance oral bioavailability enhancement of high Log P compounds due to their solubilization capability, along with their biopharmaceutical role in oral absorption processes. Lipid excipients also can stimulate biliary secretion as soon as the fatty acids, e.g., unsaturated LCFAs, reach the stomach. Furthermore, stimulation of chylomicron secretion by the unsaturated LCFAs aids in enhanced passage into the lymphatic pathway. However, APIs are evaluated individually to assess compatibility for solubilization in specific formulation excipients and for an ability to be absorbed following oral administration and a relative partitioning between hepatic (blood) and lymphatic delivery.

As discussed above, significant efforts have been directed to the development of improved formulations for enhancing the bioavailability of a therapeutic drug for oral delivery. However, chemical alteration of a therapeutic drug for the purpose of improving oral delivery properties is uncommon because attachment of additional atoms to the therapeutic drug may significantly alter chemical activity towards the intended cellular target(s). Also, there has not been an identified or agreed upon approach in which chemical drug modification can be achieved to consistently improve lymphatic absorption or compound solubility. Thus, optimization of bioavailability and efficacy traditionally is accomplished by evaluating routes of administration (e.g., oral, intravenous, intradermal) together with exploration of dose ranges, drug delivery schedules, combination therapies, and optimization of formulations.

One area of significant interest is the development of approaches that enhance delivery of therapeutic drugs into the lymphatic system. However, therapeutic drugs developed for high activity against their intended targets typically are not compatible for lymphatic absorption due to current knowledge requiring high Log P values. The needs of pharmaceutical companies for a consistent and reliable lymph-directed drug delivery approach have not been met. Therefore, an important need exists for the discovery and development of compounds and methods that provide a lymph-directed uptake of drugs.

U.S. Pat. No. 9,611,258 and PCT/US2017/040866, each incorporated herein by reference in their entirety, disclose multifunctional inhibitors that target KRAS-activated cancers by targeting the MAP kinase and PI3K pathways. Co-targeting was achieved by linking individual inhibitors, e.g., mTOR, PI3K, and MEK inhibitors, after chemical modification, to a linker to provide a multifunctional inhibitor compound. Individual mTOR, PI3K, and MEK inhibitors, chemically modified to accommodate a linker, while maintaining high binding affinity towards their respective enzyme targets, were conjugated to provide bifunctional, trifunctional, and tetrafunctional mTOR/MEK/PI3K inhibitors. The compounds inhibited KRAS-driven tumor progression by simultaneously targeting two or three critical regulatory nodes, i.e., mTOR, MEK, and PI3K, and in so doing intercepted the cross-talk that occurs between their respective pathways.

mTOR, MEK, and PI3K inhibitors are known in the art. For example, U.S. Pat. No. 7,897,792 discloses a class of coumarin-based MEK inhibitors. PI3K inhibitors are disclosed, for example, in U.S. Patent Nos. 2010/0249099; 2011/0009405; and 2011/0053907. The combined use of PI3K and MEK inhibitors to treat lung cancer is disclosed, for example, in Engelman et al., Nature Medicine, Vol. 14, Number 14, pages 1351-56 (2008).

mTOR inhibitors also are known in the art, for example in WO 2006/122806, WO 2010/003816, U.S. Pat. No. 9,284,315, and WO 2012/068106. In some embodiments, a prior art inhibitor is a dual mTOR and PI3K inhibitor.

Janus kinase inhibitors, also known as JAK inhibitors or jakinibs, are known in the art for example in U.S. Patent No. 2001/0220139. In some embodiments, a prior art JAK inhibitor known as Cerdulatinib is a type of medication that functions by inhibiting the activity of one or more of the Janus kinase family of enzymes (JAK1, JAK2, JAK3, TYK2), thereby interfering with the JAK-STAT signaling pathway. These inhibitors have therapeutic application in the treatment of cancer and inflammatory diseases such as rheumatoid arthritis. There is interest in their use for various skin conditions. JAK3 inhibitors are attractive for potential treatment of various autoimmune diseases since this signaling pathway is mainly restricted to lymphocytes.

SUMMARY OF THE INVENTION

The present invention is directed to compounds that target the MAP kinase, JAK and PI3K pathways via a lymphatic-directed uptake of the compounds, and to methods of treating a disease or condition by administering such a compound to an individual in need thereof. The present compounds have been developed to target these important signaling pathways via lymphatic transport in order to combat diseases associated with their pathway dysregulation.

The present invention therefore is directed to single-agent functional compounds designed to bind to mTOR, MEK, JAK and PI3K, and to inhibit mTOR, MEK, and PI3K activity via a lymphatic delivery.

The present compounds are designed to possess physiochemical properties, such as lipid solubility, that allows a lymphatic-directed absorption of the compounds. In particular, the present compounds exhibit a c Log P between 1 and 10, and preferably between 1 and 5.

More particularly, the present invention is directed to novel compounds that are capable of inhibiting key signal transduction pathways (i.e., mTOR, MEK, JAK and PI3K) implicated in tumor growth, progression, and metastasis of cancers.

The present invention therefore is directed to inhibitors of mTOR, MEK, JAK and PI3K enzymes, to compositions comprising the inhibitors, and to methods of using the inhibitors in a therapeutic treatment of conditions and diseases wherein inhibition of mTOR, MEK, JAK and PI3K activity provides a benefit. The present compounds are potent inhibitors of mTOR activation, MEK activation, JAK activation and PI3K activation, and are useful in the treatment of cancers, and particularly KRAS mutant tumors as well as fibrotic, autoimmune and inflammatory disorders.

The present invention is particularly directed to therapeutic drugs that have been covalently bound to linkers, which provide the physiochemical properties and solubility for lymphatic-directed absorption after administration. The functional inhibitors have a c Log P of from 1 to 10, and typically from 1 to 7.

In various embodiments, the present inhibitors are mono-, di-, tri, or tetra-functional compounds, wherein one or more therapeutic drug is covalently bound to a linker. In one embodiment, a single therapeutic drug is bound to a linker. In other embodiments, two to four therapeutic drug molecules, the same or different, are bound to a single linker.

In one embodiment, the present invention provides a method of treating a condition or disease by administering a therapeutically effective amount of a present compound to an individual in need thereof. The disease or condition of interest is treatable by inhibition of mTOR and/or MEK and/or PI3K and/or JAK, for example, a cancer.

Yet another embodiment of the present invention is to provide a method of treating a disease or condition comprising providing a therapeutic drug, modifying the drug by covalent attachment of a linker to the drug to provide a modified drug, and administering the modified drug to an individual in need thereof, wherein the modified drug is absorbed by the lymphatic system of the individual for delivery to a target in the individual.

Another embodiment of the present invention is to provide a composition comprising (a) a present inhibitor and (b) an excipient and/or pharmaceutically acceptable carrier useful in treating diseases or conditions wherein inhibition of one or more of mTOR, MEK, JAK and PI3K provides a benefit.

Another embodiment of the present invention is to utilize a composition comprising a present compound and a second therapeutically active agent in a method of treating an individual for a disease or condition wherein inhibition of at least one of mTOR, MEK, JAK and PI3K provides a benefit.

In a further embodiment, the invention provides for use of a composition comprising a present inhibitor and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising a present inhibitor, and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

These and other embodiments and features of the present invention will become apparent from the following detailed description of the preferred embodiments.

DETAILED DESCRIPTION OF THE PREFERRED EMBODIMENTS

Figure 1:
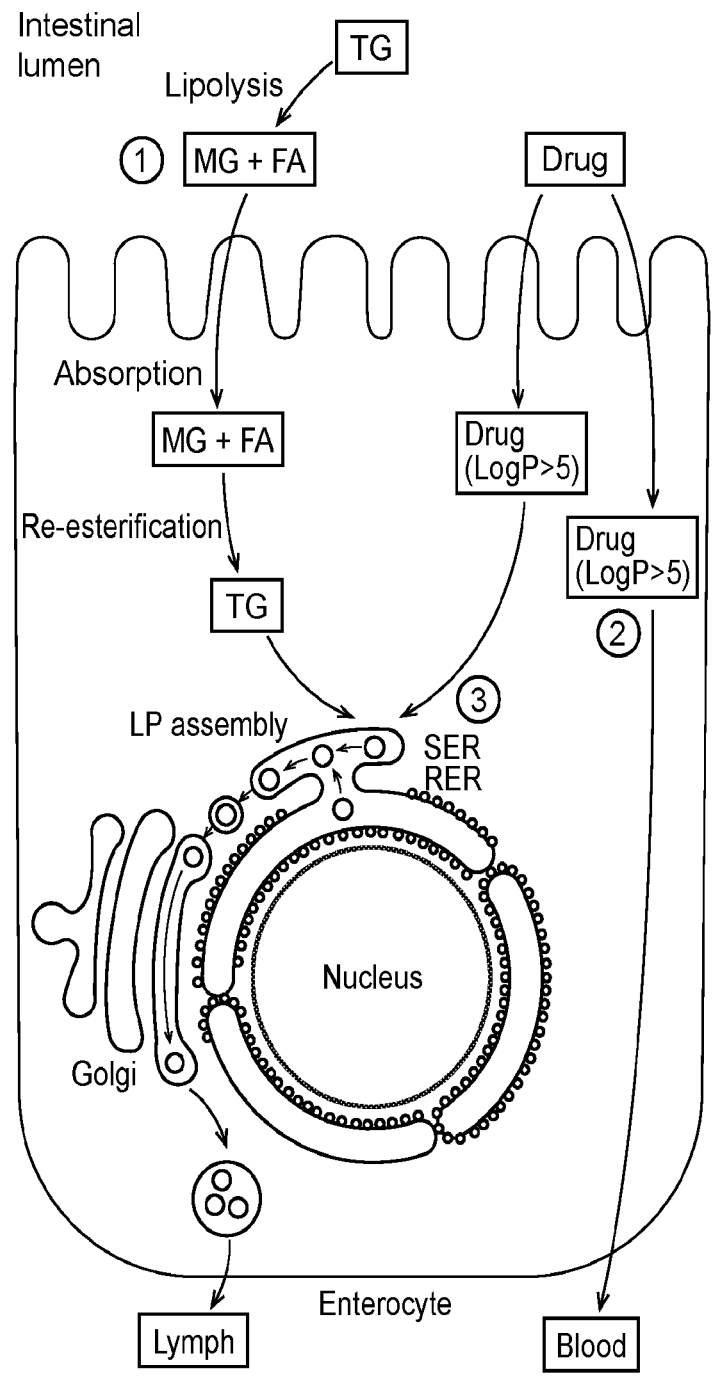
FIG. 1 illustrates therapeutic drug absorption via the vascular system and the lymph system.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "PI3K" as used herein means a Class I (including Class Ia and Class Ib), Class II, or Class III phosphonoinositide-3-kinase, as defined in U.S. Patent Publication No. 2011/0009405, incorporated herein by reference in its entirety.

The term "MEK" as used herein means mitogen-activated protein kinase.

The term "mTOR" as used herein means mechanistic target of rapamycin.

The term "JAK" as used herein means Janus kinase.

The term "a disease or condition wherein inhibition of mTOR and/or PI3K and/or JAK and/or MEK provides a benefit" pertains to a condition in which at least one of mTOR, PI3K, JAK and MEK, and/or an action of at least one of mTOR, PI3K, JAK and MEK, is important or necessary, e.g., for the onset, progress, expression of that disease or condition, or a disease or a condition which is known to be treated by an mTOR, PI3K, JAK or MEK inhibitor. An example of such a condition includes, but is not limited to, a cancer. One of ordinary skill in the art is readily able to determine whether a compound treats a disease or condition mediated by one or more of mTOR, PI3K, JAK and MEK for any particular cell type, for example, by assays which conveniently can be used to assess the activity of particular compounds.

The term "second therapeutic agent" refers to a therapeutic agent different from a present functional inhibitor and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, compounds of the present invention are potent inhibitors of MEK and PI3K or mTOR, MEK, PI3K and JAK can be used in treating diseases and conditions wherein inhibition of mTOR and/or MEK and/or PI3K and/or JAK provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce mTOR, MEK, JAK and PI3K signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a present inhibitor can be administered at the same time or sequentially in any order at different points in time as a second therapeutic agent. A present inhibitor and the second therapeutic agent can be administered separately, in any appropriate form and by any suitable route. When a present inhibitor and the second therapeutic agent are not administered concurrently, it is understood that they can be administered in any order to a subject in need thereof. For example, a present inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a present inhibitor and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Research has established that targeting mTOR, MEK, JAK and PI3K using small molecule inhibitors is a viable cancer therapeutic strategy. However, cancers with KRAS mutation are known to be constitutively activated, refractory to standard of care, and a marker for poor prognosis. Two KRAS effector pathways, MAPK and PI3K, are important harbingers of proliferation and survival, respectively, and are mechanism of resistance for each other. Pre-clinical studies of cancers have shown that multiple inhibition of effector pathways have synergistic effects, which provides a rationale for combination therapies in a clinical setting.

The present compounds and methods provide a lymphatic-directed absorption of therapeutic drugs, and an increased solubility and bioavailability of the therapeutic drug by covalent attachment of a chemical moiety, i.e., a linker, to the therapeutic drug, which alters the physiochemical properties of the drugs. Embodiments include, but are not limited to, mono-attachment of a drug on a single end of the lymphatic-directing functional moiety, attachment of a drug to each end of the moiety, or attachment of drugs using branched/star moieties (multiple moieties emanating from a central core group) or combination moieties (multiple chains grafted onto a polymer backbone) to provide multifunctional activities. Functional attachment of a therapeutic drug to a linker confers physiochemical alterations leading to improved lymphatic-directed absorption, thus reducing first-pass hepatic metabolism.

The intestinal lymphatic system has gained significant interest for the delivery of hydrophobic drugs, macromolecules, e.g., peptides, proteins and vaccines, and particulate drug carriers, such as nanoparticles (Paliwal, Paliwal et al. 2009). There has been significant effort in the development of lymph-directing strategies, but these strategies have primarily focused on promoting lymphatic uptake using lipid prodrug conjugates with alkyl esters and triglyceride mimetics (Trevaskis, Kaminskas et al. 2015) (Hu, Quach et al. 2016), nanoparticulates, such as chylomicron mimicking carriers (Paliwal, Paliwal et al. 2009), lipid class and lipid vehicle dispersions (Porter, Charman et al. 1996, Faisal, Ruane-O'Hora et al. 2013), co-administration with food (Trevaskis, Shackleford et al. 2009), and attachment of hydrophobic moieties (Shackleford, Faassen et al. 2003), as well as other strategies (Trevaskis, Kaminskas et al. 2015). Lymph-directed drug absorption is of significant interest to eliminate first-pass hepatic metabolism, reduce overall systemic toxic side effects, and reduce drug doses required to reach efficacious levels. Moreover, the ability to target the lymphatic system with cancer chemotherapies would provide significant opportunities for direct treatments of metastatic spread of cancers into the lymphatic system (Karaman and Detmar 2014), as well as to treat hematological/lymphatic cancers.

The physiological path involved in the absorption of drugs following oral delivery of a compound or drug delivery system is through initial entry through the intestinal epithelium to access the underlying interstitial space. This space is connected to blood and lymph capillaries whereby drainage or removal of compounds can be accomplished. Access to the lymphatic system is a selective process because substantial physical and biological barriers prohibiting lymphatic entry following oral delivery exist. It was theorized that therapeutic drugs require a composition containing, for example, macromolecular constructs including nanoparticles or particulate materials (artificial or biological). However, the instability of macromolecules within the gastrointestinal tract, with a low permeability across the gastrointestinal mucosa, are significant physical and biological barriers for a drug to enter into the lymphatic system following oral administration. Further limiting lymphatic absorption of therapeutic drugs is that the flow rate of blood through intestinal blood capillaries and portal vein is higher by about four hundred fold more than the flow rate of lymph fluid through the intestinal lymphatic system. Most small molecules, which are able to readily diffuse into both blood (Trevaskis, Charman et al. 2008) and lymph capillaries, are thus absorbed and transported from the intestine via the blood circulation rather than the lymphatic system owing to higher mass transport (Trevaskis, Kaminskas et al. 2015).

Substantial lymphatic transport may occur following oral administration when macromolecular access to the gastrointestinal interstitium is possible and where access to blood capillaries is restricted. This has been described for lipophilic small-molecule drugs and prodrugs that are absorbed, then associate with intestinal lipoproteins during passage across enterocytes, and with macromolecular constructs, such as antigens, tolerogens, peptides, proteins, and nano-sized delivery systems, that are stable in the gastrointestinal tract and are permeable, at least to some extent, across the gastrointestinal epithelium (Trevaskis, Charman et al. 2008, Yanez, Wang et al. 2011, Kunisawa, Kurashima et al. 2012) (Florence 2005, Bakhru, Furtado et al. 2013) (Trevaskis, Kaminskas et al. 2015).

The current understanding of lymphatic-directed approaches for drug delivery require compounds to be highly lipophilic (Trevaskis, Shanker et al. 2010) (Choo, Boggs et al. 2014), with a log P>5 and with a solubility >50 mg per gram in long-chain triglyceride lipid (Charman 1986) in order to allow partitioning of the compound into developing lipoproteins in the enterocyte, thereby providing a mechanism of preferential access to the intestinal lymph.

FIG. 1 shows that dietary lipids (including triglycerides (TGs)) and lipophilic drugs access the mesenteric lymph vessels following absorption across enterocytes. TGs are digested within the gastrointestinal lumen at the sn-1 and sn-3 position to release fatty acids (FAs) and 2-monoglyceride (MG). FAs and MG are absorbed from the gastrointestinal lumen into enterocytes where they are re-synthesized to TG in the smooth endoplasmic reticulum (SER). The TG droplets formed in the SER combine with 'primordial lipoproteins' consisting of phospholipids and apolipoproteins that are assembled in the rough endoplasmic reticulum (RER), ultimately resulting in the assembly of nascent lipoproteins (LPs). Intestinal LPs are trafficked to the Golgi apparatus, exocytosed from the enterocyte and transported away from the intestine via the mesenteric lymphatics. Most drugs are absorbed across the enterocyte into the vascular capillaries that drain the small intestine and are transported to the systemic circulation via the portal vein (as the rate of fluid flow in the portal vein is 500-times higher than that of the mesenteric lymph). In contrast, highly lipophilic drugs (typically, but not exclusively, those with log P values >5 and solubility >50 mg per g in long-chain TG lipid) partition into developing LPs in the enterocyte, providing a mechanism of preferential access to the intestinal lymph. Drug delivery to the intestinal lymph avoids first-pass metabolism in the liver as lymph drains directly into the systemic circulation via the thoracic lymph duct (Trevaskis, Kaminskas et al. 2015).

An advantage of drug delivery to the intestinal lymph is that the drug will avoid first-pass metabolism in the liver because lymph drains directly into the systemic circulation via the thoracic lymph duct. For some highly lipophilic drugs, intestinal lymphatic transport may be more efficient for transport to the systemic circulation following oral delivery (Trevaskis, Charman et al. 2008). For these drugs, lymphatic access occurs via association with lipid absorption and lipoprotein assembly pathways during diffusion across intestinal absorptive cells (enterocytes) (Trevaskis, Charman et al. 2008, Yanez, Wang et al. 2011) (FIG. 1). Upon exocytosis from enterocytes, drug-lipoprotein complexes are transported across the basement membrane and trafficked from the intestinal lamina propria via the lymphatics. The generalized concept which has emerged from the scientific literature is that the intestinal lymphatic transport of lipophilic drugs is only substantial when the drug is administered with a source of lipid (from food or a formulation) because this is required to promote lipoprotein formation (Khoo, Shackleford et al. 2003, Trevaskis, Charman et al. 2008, Yanez, Wang et al. 2011). The type and dose of lipid with which the drug is administered therefore becomes important in directing lymphatic transport. After absorption, the majority of long-chain (>C14) lipids are assembled into intestinal lymph lipoproteins, whereas the reverse is true for medium-chain lipids (<C12), for which the majority diffuse across enterocytes to directly enter the blood circulation (Caliph, Charman et al. 2000, Trevaskis, Caliph et al. 2013). Drug administration with long-chain lipids can therefore promote lymphatic transport more effectively than administration with short- or medium-chain lipids (Caliph, Charman et al. 2000, Trevaskis, Charman et al. 2008, Trevaskis, Caliph et al. 2013).

The art (Charman 1986) suggested that the physicochemical properties required to promote drug association with intestinal lipoproteins (and therefore to promote lymphatic transport) were a log P value of >5 and solubility of >50 mg per g in long-chain TG. These approximations have been used to successfully predict the potential for intestinal lymphatic transport, although some exceptions are evident, including examples of low lymphatic transport for compounds with high TG solubility (Myers 1992) and substantial lymphatic transport for drugs with relatively low TG solubility (Trevaskis, Shanker et al. 2010, Choo, Boggs et al. 2014). In the latter cases, drug affinity for the interfacial region of lipoproteins rather than the triglyceride-rich core, or affinity for an unidentified active transport process, have been suggested as alternative drivers of lymphatic transport (Gershkovich and Hoffman 2005, Gershkovich, Fanous et al. 2009, Trevaskis, Shanker et al. 2010).

Drugs also may influence their own disposition into the lymph by altering the production of lymph lipoproteins (Trevaskis, Shanker et al. 2010, Lawless, Griffin et al. 2015), further complicating predictive strategies. Nonetheless, the potential for drugs to associate with intestinal lymph lipoproteins in vivo, and therefore to access the intestinal lymph, has been estimated with some success using in vitro drug affinity assays using isolated or reassembled chylomicrons (Gershkovich and Hoffman 2005, Trevaskis, Shanker et al. 2010, Lu, Qiu et al. 2015) or by analysis of a series of molecular descriptors using in silico approaches (Holm and Hoest 2004, Gershkovich, Fanous et al. 2009). However, as described above, what has emerged is a general understanding for properties to aid in lymphatic-directed uptake rather than a consistent or generalizable methodological chemical solution. Thus, there is an urgent need for a lymphatic-targeted approach that is flexible for adaptation across many different drugs.

The present invention therefore provides for significant partitioning of drugs into the lymphatic system following delivery. The present invention involves attachment of a multi-ethylene glycol (mEG) functional moiety, i.e., a linker, to a drug which in turn provides for lymphatic-directed uptake. The present compounds and methods are a novel approach for facilitation of lymphatic uptake of small molecules. Historically, long-chain polyethylene glycol (PEG) chemical units (Turecek, Bossard et al. 2016, Ma 2017), as well at other chemical groups (van Witteloostuijn, Pedersen et al. 2016), have been investigated for protecting kidney and liver filtration of biologicals (peptides, proteins, etc.) and nanoparticles for improving their overall biological half-life.

It has been observed that increasing lipoprotein affinity is a property that can enhance intestinal lymphatic transport. As a first order approach, this was achieved by the introduction of structural modifications to enhance lipophilicity, and thereby generate highly lipophilic structural drug analogues. However, this is inconsistent with the drug development 'rule of 5' used to evaluate possible drug candidates (Lipinski, Lombardo et al. 2001). Furthermore, drugs with properties outside of the 'rule of 5' are questioned regarding their lipophilic efficiency and toxicity (Hopkins, Keseru et al. 2014).

In part, a significant barrier in the drug development arena is the Lipinski 'rule-of-five' (Lipinski, Lombardo et al. 2001). The 'rule of five' states that in general, an orally active drug should not violate more than one of the following criteria: 1) No more than 5 hydrogen bond donors (the total number of nitrogen-hydrogen and oxygen-hydrogen bonds); 2) No more than 10 hydrogen bond acceptors (all nitrogen or oxygen atoms); 3) The molecular mass should be less than 500 Daltons; 4) An octanol-water partition coefficient log P not greater than 5. All criteria numbers are multiples of five hence the origin of the rule's name. These rules provide a rule of thumb for development of a drug candidate with required chemical properties needed for it to be orally active in humans. The rules were based on the observation that most orally administered drugs are relatively small in terms of their molecular weight (<500 Daltons) and moderately lipophilic molecules (Lipinski, Lombardo et al. 2001). While the rule describes molecular properties important for a drug pharmacokinetics in the human body, including absorption, distribution, metabolism, and excretion ("ADME"), it does not predict whether a compound is pharmacologically active.

Furthermore, the 'rule of five' is used in drug discovery to guide lead structure optimization through a step-wise process to increase the activity and selectivity of the compound as well as to ensure drug-like physicochemical properties are maintained (Oprea, Davis et al. 2001). Candidate drugs that conform to the "rule of 5" tend to have lower attrition rates during clinical trials, thereby increasing a likelihood of reaching final clinical approval (Leeson and Springthorpe 2007). While there are exceptions to Lipinski's Rule, the rule is used as a basic guideline by many pharmaceutical companies. Moreover, the 'rule of five' is not compatible with the synthetic development of a drug having the chemical properties required for lymph-directed uptake.

An alternative approach proposed to boost lipophilicity has been to synthesize a lipophilic prodrug, whereby the parent drug (API) is conjugated to a lipid or lipophilic moiety via a cleavable linker (Lambert 2000). The simplest approach to a lipid prodrug is to produce an alkyl ester that promotes passive partition into lipoproteins in the enterocyte to facilitate lymphatic transport. However, this prodrug approach has been found to be relatively inefficient. Furthermore, lipophilic prodrugs that can integrate into lipid processing pathways, such as triglyceride or phospholipid re-synthesis, are found to be more effective (Sugihara, Furuuchi et al. 1988, Lambert 2000, Han, Quach et al. 2014). In this regard, triglyceride mimetic prodrugs of the immunosuppressant mycophenolic acid were reported to be more effective in promoting lymphatic transport than simple alkyl esters or amides (Han, Quach et al. 2014). This study (Han, Quach et al. 2014) and others (Sugihara, Furuuchi et al. 1988) revealed substantial structural sensitivities in the absorption and lymphatic transport of glyceride prodrugs, in particular the point of conjugation and the nature of the conjugation chemistry. In general, conjugation at the sn-2 position and via an ester bond appears to promote lymphatic transport most effectively (Sugihara, Furuuchi et al. 1988, Lambert 2000, Han, Quach et al. 2014), with exceptions (Sugihara, Furuuchi et al. 1988). From the scientific literature, a generalized approach for directing drugs into the lymphatic system has not emerged to provide a unified approach generally applicable, accepted, and utilized by the pharmaceutical industry.

As discussed below, the present invention provides the following benefits:

chemical modification of a therapeutic drug by attachment of a chemical moiety, i.e., a linker, as a lymphatic modifier, which is compatible with a lymphatic-directed uptake;

synthesizing or chemically modifying a therapeutic drug with the linker to significantly increase its bioavailability and/or lymphatic uptake to improve the overall therapeutic benefit following administration;

improving the lymph-directed partitioning of orally delivered drugs and reducing the lipophilicity of a compound;

providing therapeutic applications of mono-targeted and multi-targeted drugs for oral administration, while providing for lymphatic absorption, improved pharmacokinetics, and reduced systemic toxicity;

attaching one or more molecules of a given drug or attachment of two or more different drugs to a single lymphatic modifier;

providing formulations of two or more modifier-drug combinations within a single dose mixture with independent concentrations depending upon the requirements of the clinical application;

providing chemical linkers that are covalently attached to a drug for lymphatic absorption. Following administration, the chemical modifier may be detached by enzymatic or chemical processes in the body, resulting in separation and release of the linker modifier from its attached drug; and providing a linker for lymphatic-directed uptake to allow optimization of Log P values for compounds in order to improve formulation and ADME parameters.

The present compounds also can be used with small molecules, peptides, nanoparticles/nanostructures and biologics to adjust Log P values to further enhance ADME properties.

Lymphatic-system targeting chemical linkers contain multi-ethylene glycol (mEG) molecular structures. Attachment of the parent drug to the linker maintains sufficient activity of the parent drug to achieve the intended therapeutic effect. The present compounds have a covalent attachment wherein separation of the drug can occur following administration by normal metabolic processes in the body, including hepatic metabolism. Additionally, the lymphatic-directing linker can be attached as a bioreversible derivative of the drug molecule, which is chemically designed to undergo an enzymatic and/or chemical transformation following in vivo administration.

The transformation process releases active parent drug from the lymphatic-targeting moiety to exert its desired pharmaceutical effect. This approach is termed "a lymphatic-directed prodrug strategy" wherein following administration, the drug is taken up into the lymphatic system, thus bypassing first pass hepatic metabolism. Later in the process, the parent drug detaches from the targeting moiety. Prodrug strategies allow for improvement in the physiochemical, biopharmaceutical, and/or pharmacokinetic properties of a pharmacologically active compound (Rautio, Kumpulainen et al. 2008), and in the present invention, directs the therapeutic drug through a lymphatic absorption process. The lymphatic-directing ligand also overcomes barriers of drug formulation and delivery, including improving aqueous solubility, chemical instability, insufficient oral absorption, rapid pre-systemic metabolism, toxicity, and local irritation.

An additional drug therapy concept, termed "polypharmacology", has emerged. An urgent need exists for pharmaceutical agents that are able to act on multiple targets or disease pathways because signaling pathways are complex, interconnected with significant levels of cross talk, and numerous compensatory possibilities making agents which target a single signaling node prone to failure. Drug combinations are frequently withdrawn from use due to adverse side-effects or toxicities because drugs often interact with multiple targets and the unintended drug-target interactions can result in side-effects. Polypharmacology is a major challenge in drug development because it requires next generation drugs to be more effective and less toxic (Reddy and Zhang 2013). Inherent in the concept of polypharmacology is that effective drugs can be developed by specifically modulating multiple targets because complex diseases, such as cancer and central nervous system diseases, may require multi-targeted therapeutic approaches. In this respect, a drug that has activities against multiple signaling nodes related to a network of interacting targets should provide for higher efficacy with less toxicity using single-targeted agents or a combination of multiple drugs (Anighoro, Bajorath et al. 2014). The limitation of polypharmacology is that a drug with multiple targets may not provide reduced systemic toxicity than over single or combination therapies. While lymphatic-targeting can be used via attachment of a single drug using a pharmaceutically acceptable linker, it also can be used to couple two or more pharmacologically identical or different active drugs together in a single molecule.

Relevant to this strategy is attachment of lymphatic-targeting linkers to functional groups on the drug molecule amenable to modification, including, for example, carboxylic, hydroxyl, amine, phosphate/phosphonate, and carbonyl groups. Additional functional groups for attachment and targeting are also feasible. Illustrated below are nonlimiting lymphatic-targeting linkers that can be covalently attached to a drug to provide lymphatically-targeted compounds.

Table 1 contains nonlimiting examples of multi-ethylene glycol (mEG) functional lymphatic-targeting moieties that can be attached to a therapeutic drug to improve drug ADME characteristics, as well as improve lymphatic uptake following administration (e.g., oral, intramuscular, subdermal). This approach also provides a flexible chemical approach to adjust the overall Log P of the drug, while maintaining a lymphatic directed delivery. For example, a drug with a very low Log P value (Log P<0) is not predicted to be delivered and absorbed by the lymphatic system. However, by addition of the mEG functional units in combination with an alkyl moiety, the Log P can be adjusted to optimize the drug ADME properties, together with lymphatic uptake of the drug. As shown in Table 2, a wide variety of chemical structures can be used to achieve the required ADME properties for an individual drug compound.

The lymphatic-targeting functional and ADME-adjusting linkers are removed by enzymatic and/or chemical means in the body following administration. The mEG functional linkers offer a flexible approach to drug development because they provide opportunities to modify and optimize drug solubility, toxicology, pharmacokinetics, pharmacodynamics, metabolism, drug absorption, drug distribution, drug formulation, drug combination therapies, and improve overall drug delivery and efficacy. The flexibility arises from the combinations of $R_1$, $R_2$, X, and Y chemical groups that are available for drug optimization purposes.

TABLE 1

Examples of multi-ethylene glycol (mEG) functional lymphatic targeting linkers that can be attached to drugs.

Single and multi-pronged mEG ProDrugs

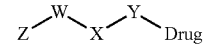

Z, X = phenyl, 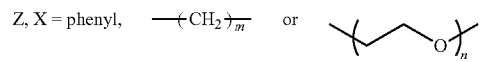

m = 0-20; n = 1-20 or any combination of m, n

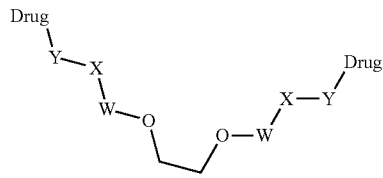

W = phenyl, 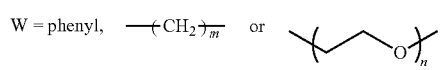

m = 0-20; n = 0-20 or any combination of m, n

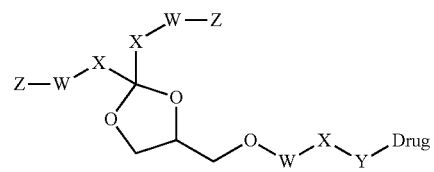

X, Z = phenyl, 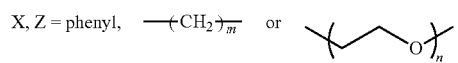

TABLE 1-continued

Examples of multi-ethylene glycol (mEG) functional lymphatic targeting linkers that can be attached to drugs.

Single and multi-pronged mEG ProDrugs m = 0-20; n = 0-20 or any combination of m, n

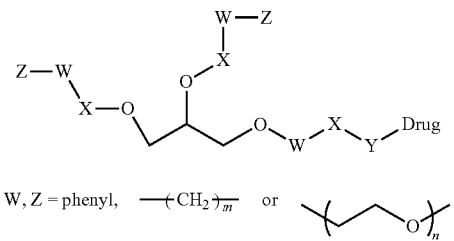

W, Z = phenyl, $-(CH_2)_{\overline{m}}$ or $-\{\!\!\!-\!\!\!\}_n\!\!\!O\!\!\!-\!\!\!\}$ m = 0-20; n = 0-20 or any combination of m, n

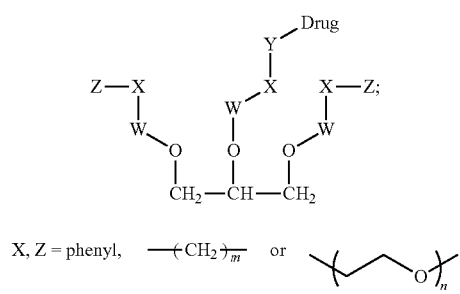

X, Z = phenyl, $-(CH_2)_{\overline{m}}$ or $-\{\!\!\!-\!\!\!\}_n\!\!\!O\!\!\!-\!\!\!\}$ m = 0-20; n = 0-20 or any combination of m, n

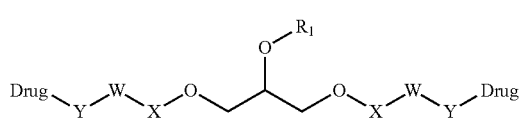

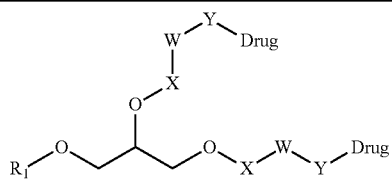

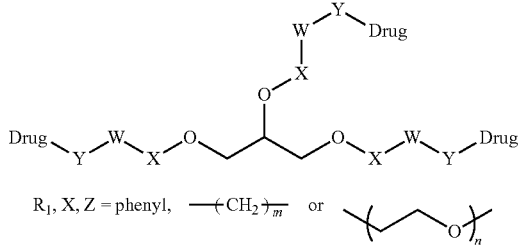

$R_1$, X, Z = phenyl, $-(CH_2)_{\overline{m}}$ or $-\{\!\!\!-\!\!\!\}_n\!\!\!O\!\!\!-\!\!\!\}$ m = 0-20; n = 0-20 or any combination of m, n $$W = \begin{matrix} O \\ \| \\ -C- \end{matrix}$$

or $$\begin{matrix} O \\ \| \\ -S- \\ \| \\ O \end{matrix}$$

or $$\begin{matrix} R \\ | \\ -N- \end{matrix}$$

or $$\begin{matrix} O & H \\ \| & | \\ -C-N- \end{matrix}$$

and R = H, alkyl or phenyl
Y = see Table 2 of Functional groups

In Table 1, m and n, independently, preferably are 1 to 15, and more preferably 2 to 10; and "Drug" is a pharmaceutically active compound having a functional group capable of bonding to functional group "Y".

TABLE 2

Functional group attachments (Y) for mEG linkers.

1) Alcohols (HO—R)

| Functional Group | Ester | Carbonate | Carbamate | Phosphate I | Phosphate II |
|---|---|---|---|---|---|
| Y | $\overset{O}{\underset{\|}{-C-O-R}}$ | $\overset{O}{\underset{\|}{-O-C-O-R}}$ | $\overset{O}{\underset{\|}{-NH-C-O-R}}$ | $\overset{O}{\underset{OH}{-O-\overset{\|}{P}-O-R}}$ | $-O-\overset{O}{\underset{OH}{\overset{\|}{P}}}-O-R$ |

2) Amines (H₂N—R)

| Functional Group | Amide | Carbamate | Oxime | Imine |
|---|---|---|---|---|
| Y | $\overset{O}{\underset{\|}{-C-N-R}}\overset{}{\underset{H}{}}$ | $\overset{O}{\underset{\|}{-O-C-N-R}}\overset{}{\underset{H}{}}$ | $R_3O-N=R$ | $R_3O-N=R$ |

TABLE 2-continued

Functional group attachments (Y) for mEG linkers.

3) Carboxylic acids (HO—(C=O)—R)

| Functional Group | Amide | Carbamate |
|---|---|---|
| Y | —O—C(=O)—R | —N(H)—C(=O)—R |

4) Aldehydes/Ketones ($R_3$—(C=O)—R)

| Functional Group | Oxime | Imine |
|---|---|---|
| Y | $R_3$O—N=R | $R_3$—N=R |

(R is hydrogen, $C_{1-4}$alkyl, or phenyl)

Table 3 provides nonlimiting examples wherein c Log P [20] values are modified from >10 (Compounds 1-3) to <5 (Compound 4), which shows a wide range available for ADME optimization purposes. Further examples are provided in the examples in Table 4.

TABLE 3

Examples of triglyceride prodrug inhibitors and bivalent inhibitor prodrugs of MEK.

Triglyceride Prodrug Inhibitors of MEK (PD0316684)

| Compound | X | Y | clog P |
|---|---|---|---|
| PD0316684 | n/a | n/a | 3.68 |
| 1 | null | $C_7H_{15}$ | 11.19 |
| 2 | $CH_2$ | $C_7H_{15}$ | 12.04 |
| 3 | —O— | $C_7H_{15}$ | 11.17 |
| 4 | —O— | —(CH₂CH₂O)₃— | 4.34 |

TABLE 3-continued

Examples of triglyceride prodrug inhibitors and bivalent inhibitor prodrugs of MEK.

Bivalent Inhibitor Prodrugs of MEK

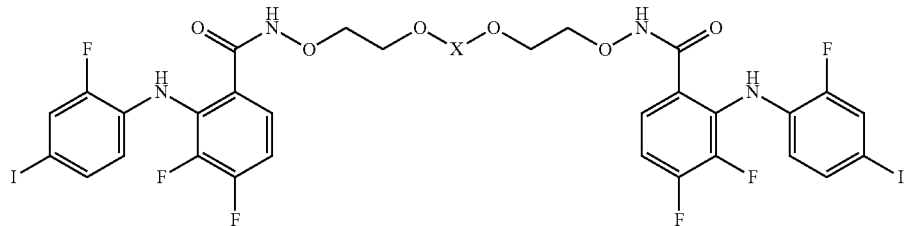

| Compound | X | clog P |
|---|---|---|
| PD0316684 | n/a | 3.68 |
| ST-5-37 | —CH$_2$CH$_2$OCH$_2$CH$_2$— | 8.44 |
| 3 | —(CH$_2$CH$_2$O)$_4$— | 7.91 |
| 4 | —C(O)—C(O)— | 8.80 |
| 5 | —C(O)—CH$_2$—C(O)— | 8.86 |
| 6 | —C(O)—O—C(O)— | 8.62 |

TABLE 4

Examples of mEG-derivatized Anti-cancer Drugs a) 5-Fluorouracil

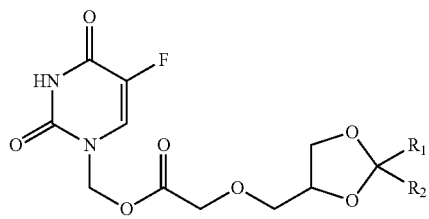

a) R$_1$ = R$_2$ = propyl; cLogP = 2.40 b) R$_1$ =  —(CH$_2$CH$_2$O)$_2$CH$_2$CH$_2$OCH$_3$;

R$_2$ = C$_9$H$_{19}$; cLogP = 3.43

TABLE 4-continued
Examples of mEG-derivatized Anti-cancer Drugs
b) Carboplatin
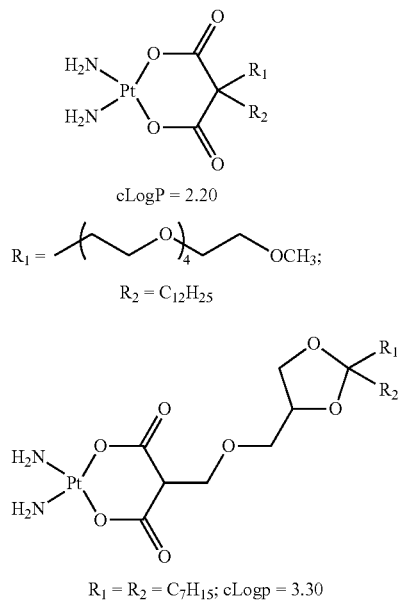
cLogP = 2.20
$R_1 = $ –(CH$_2$CH$_2$O)$_4$–CH$_2$CH$_2$OCH$_3$;
$R_2 = C_{12}H_{25}$
$R_1 = R_2 = C_7H_{15}$; cLogp = 3.30
C) Doxorubicin
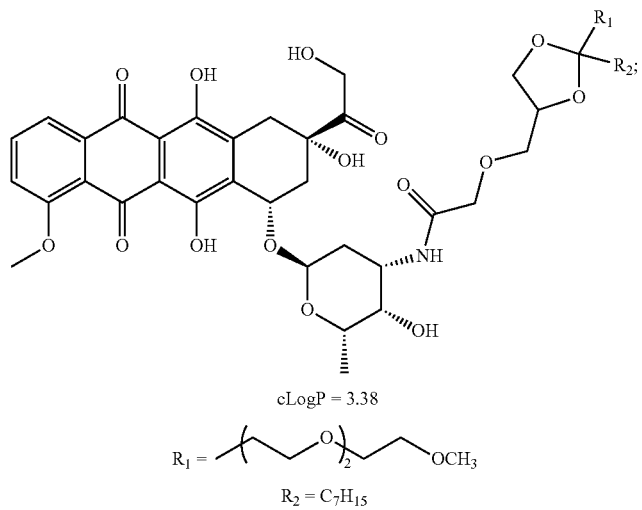
cLogP = 3.38
$R_1 = $ –(CH$_2$CH$_2$O)$_2$–CH$_2$CH$_2$OCH$_3$
$R_2 = C_7H_{15}$
d) Methotrexate
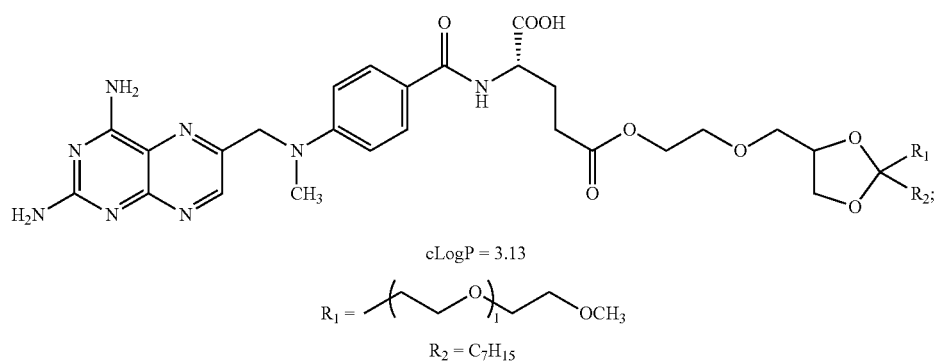
cLogP = 3.13
$R_1 = $ –(CH$_2$CH$_2$O)$_1$–CH$_2$CH$_2$OCH$_3$
$R_2 = C_7H_{15}$ TABLE 4-continued Examples of mEG-derivatized Anti-cancer Drugs e) Acetaminophen

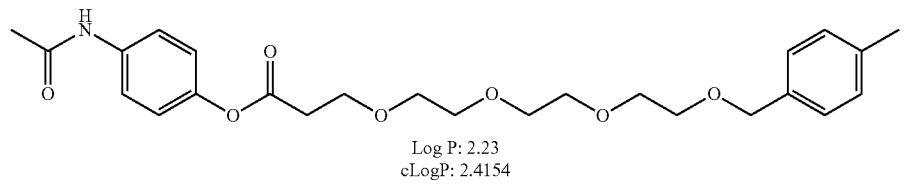 [SMILES: CC(=O)Nc1ccc(OC(=O)CCOCCOCCOCCOCc2ccc(C)cc2)cc1]

Log P: 2.23
cLogP: 2.4154 f) Aspirin

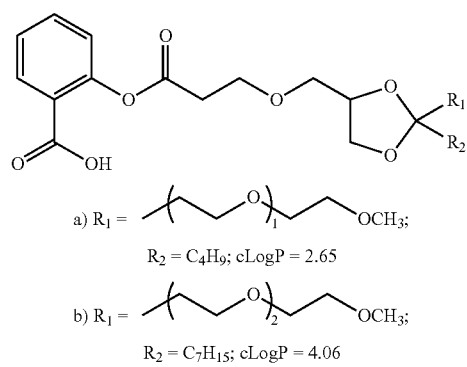

a) $R_1 =$ ⁓⁓(O)$_1$OCH$_3$;

$R_2 = C_4H_9$; cLogP = 2.65 b) $R_1 =$ ⁓⁓(O)$_2$OCH$_3$;

$R_2 = C_7H_{15}$; cLogP = 4.06 g) Ibuprofen

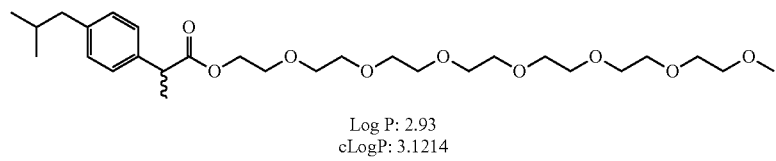 [SMILES: COCCOCCOCCOCCOCCOCCOCCOC(=O)C(C)c1ccc(CC(C)C)cc1]

Log P: 2.93
cLogP: 3.1214

Additional nonlimiting examples are provided in the following Tables 5-8, which include lymphatically-targeted signaling inhibitors for MEK, PI3K mTOR/PI3K, JAK either as direct chemical attachment or using a prodrug moiety in combination with the lymphatic-targeting functional moiety. As shown in the examples, a broad array of Log P values can be achieved by altering the length of the attached lymphatic targeting moiety, attachment of an alkyl moiety, and/or changing one moiety for another. The flexibility of this approach allows optimization of the formulation and ADME properties of a therapeutic drug to improve overall therapeutic efficacy in part through enhanced bioavailability. Additionally, a single drug can be attached or alternatively multiple drugs can be attached to a single linker to provide multi-functional targeting activities achieved by a single molecule that is absorbed lymphatically.

Attachment of a lymphatic directed functional moiety (mEG) is versatile and adaptable to a wide number of known drugs as shown in selected examples (Table 4). In Table-4, several embodiments of attachment of mEG lymphatic targeting moieties to known drugs are shown while maintaining the Log P values in the range of typical drugs. Examples include 5-fluorouracil (5-FU), carboplatin, doxorubicin, methotrexate, acetaminophen, aspirin and ibuprofen. Log P values that are lower than considered optimal from the traditional values needed for lymphatic uptake (i.e., Log P>5) can be adjusted upwards by chemical modifications to the attached functional moiety. Conversely, compounds with high Log P values can be adjusted downwards as well by addition of increased numbers of mEG units to reach a desired level. The present invention allows for flexibility to adjust ADME properties and Log P values for individual compounds by addition or subtraction of mEG lengths or the addition of alkyl or other moieties depending upon the particular biological and/or formulation requirements. Table 4 provides several examples implementing an approach involving attachment of mEG lymphatic-functional linkers for improving lymphatic uptake. Attachment of the mEG functional linkers can be accomplished for a wide variety of functional groups on drug molecules as shown in Table 4 providing a diverse set of chemical solutions to improve drug ADME properties as well as lymphatic uptake.

TABLE 5

Examples of MEK, PI3K and mTOR/PI3K lymphatic system directed mEG prodrugs.

Examples of MEK, PI3K and mTOR/PI3K targeting mEG Prodrugs a) MEK Inhibitors

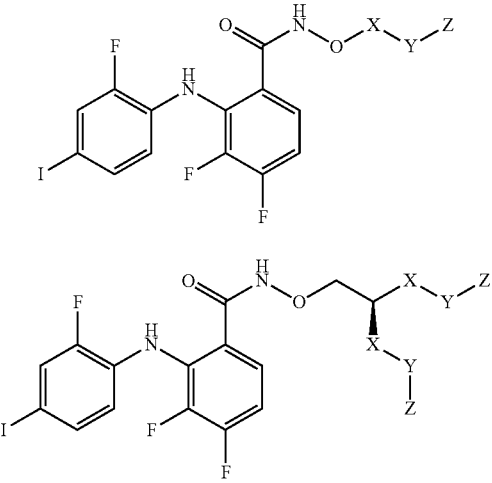

$X = \{CH_2CH_2O\}_m$ ; $Z = (CH_2)_n$ ;

m = 0-20; n = 0-20 or any combination of m, n and Y = —C(=O)—   —C(=O)—O—

—C(=O)—NH—

—P(=O)(OH)—O—

Specific example: palmitoyl ester of PD0316684

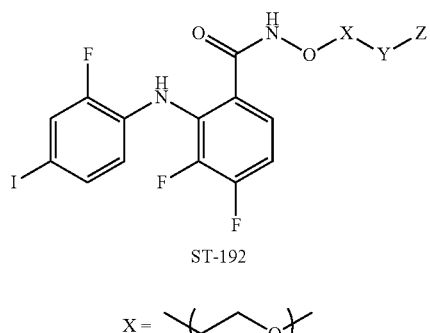

ST-192

$X = \{CH_2CH_2O\}$

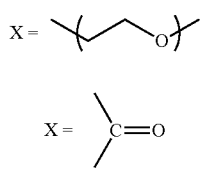

TABLE 5-continued

Examples of MEK, PI3K and mTOR/PI3K lymphatic system directed mEG prodrugs.

Examples of MEK, PI3K and mTOR/PI3K targeting mEG Prodrugs $Z = C_{15}H_{31}$
cLogP = 11.98 b) PI3K Inhibitor

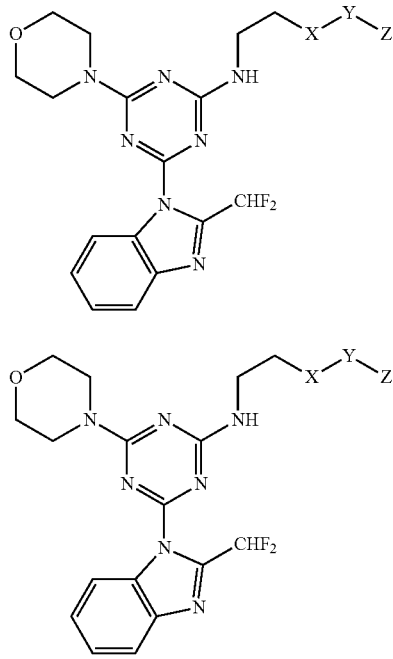

X = O

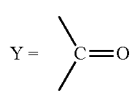

$Z = C_{15}H_{31}$
cLogP = 9.27

$X = (CH_2)_m$ ; $\{CH_2CH_2O\}_n$ ; NH, O m = 0-20; n = 0-20 or any combination of m, n and Y = —C(=O)—   —C(=O)—O—

—C(=O)—NH—

—P(=O)(OH)—O—

TABLE 5-continued

Examples of MEK, PI3K and mTOR/PI3K lymphatic system directed mEG prodrugs.

Examples of MEK, PI3K and mTOR/PI3K targeting mEG Prodrugs

Specific example: palmitoyl ester of ST-187
c) mTOR/PI3K Bifunctional Inhibitor Prodrugs

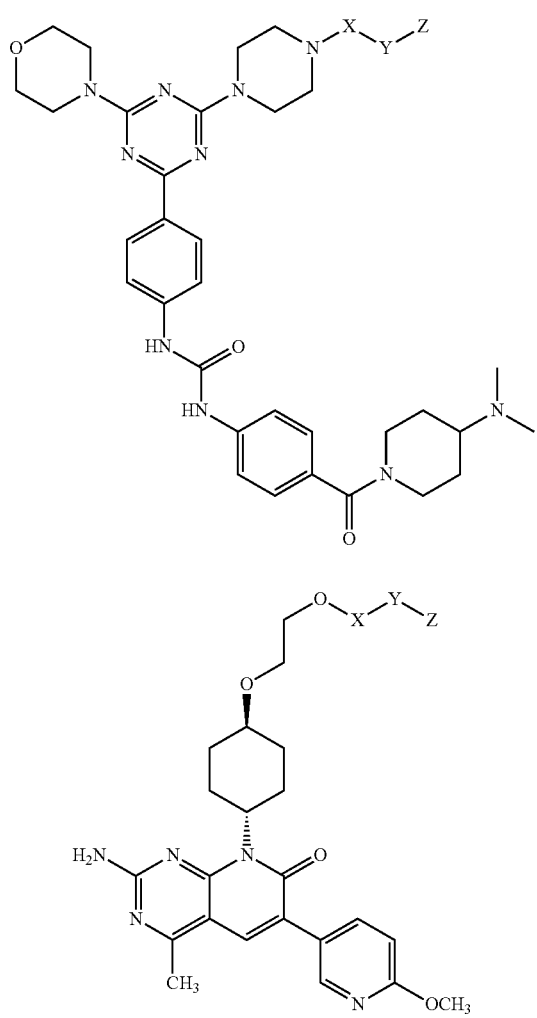

TABLE 5-continued

Examples of MEK, PI3K and mTOR/PI3K lymphatic system directed mEG prodrugs.

Examples of MEK, PI3K and mTOR/PI3K targeting mEG Prodrugs

Y, Z = —(CH$_2$)$_{\overline{m}}$ ; $\{(\phantom{x})_2 O\}_n$ NH, O, H m = 0-20; n = 0-20 or any combination of m, n
Specific example: Palmitoyl ester of PF-04691502

$X = \overset{O}{\underset{\|}{-C-}}$
Y = C$_{15}$H$_{31}$
Z = H
cLogP = 9.49
palmitoyl ester of PF04691502
(ST-5-6)

TABLE 6

Examples of mono and bis-MEK, PI3K and mTOR/PI3K lymphatic system directed mEG drugs.

a) Mono and bis MEK Inhibitors

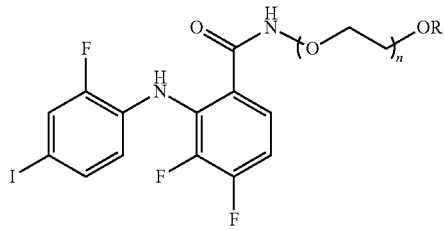

where n = 1-20 and R = H, alkyl, phenyl

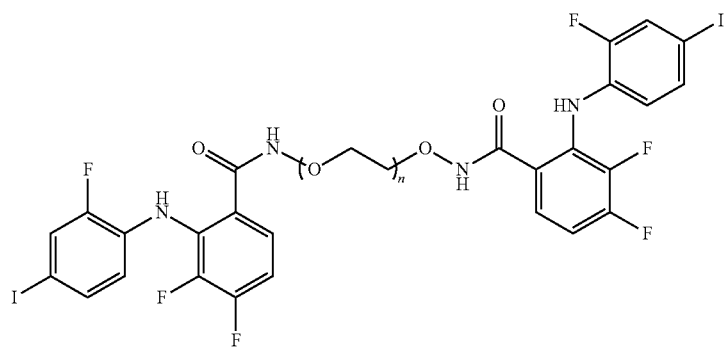

where n = 1-20
Specific example: ST-5-37

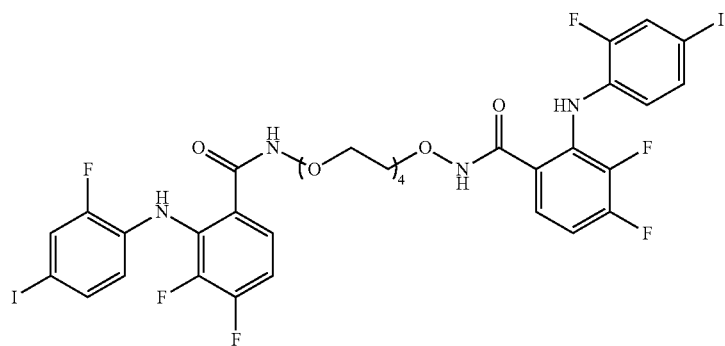

n = 4; cLogP = 8.44 b) Mono and bis PI3K Inhibitors

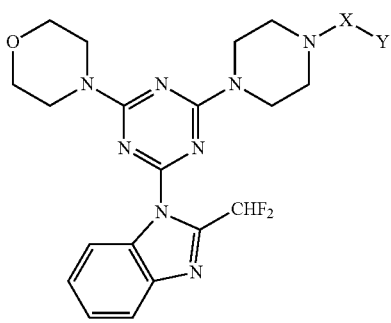

X = null, $CR_1R_2$ (where $R_1$, $R_2$ = H, alkyl, phenyl or any combination), carbonyl, CONH, S=O, $SO_2$, $SOCH_2$, $SO_2CH_2$, SONH, $SO_2NH$ or any combination.
where Y = $(CH_2CH_2O)_n$ R and n = 1-20 and R = H, alkyl, phenyl

TABLE 6-continued

Examples of mono and bis-MEK, PI3K and mTOR/PI3K lymphatic system directed mEG drugs.

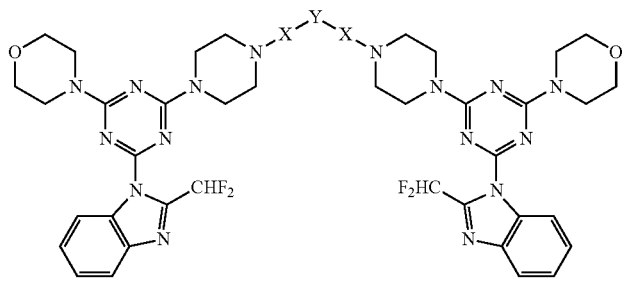

where Y = (CH$_2$CH$_2$O)$_n$ and n = 1-20
X = Z = null, CR$_1$R$_2$ (where R$_1$, R$_2$ = H, alkyl, phenyl or any combination), carbonyl, CONH, S=O, SO$_2$, SOCH$_2$, SO$_2$CH$_2$, SONH, SO$_2$NH or any combination.

20

TABLE 7

Examples of mono and bis-mTOR/PI3K inhibitors with lymph-directed targeting mEG moieties attached.

Mono and bis mTOR/PI3K Inhibitors

Example 1

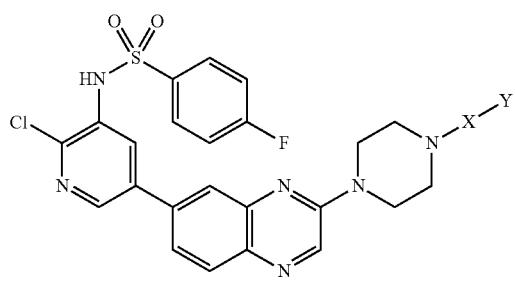

where Y = (CH$_2$CH$_2$O)$_n$R and n = 1-20 and R = H, alkyl, phenyl
X = null, CR$_1$R$_2$ (where R$_1$, R$_2$ = H, alkyl, phenyl or any combination), carbonyl, CONH, S=O, SO$_2$, SOCH$_2$, SO$_2$CH$_2$, SONH, SO$_2$NH or any combination.

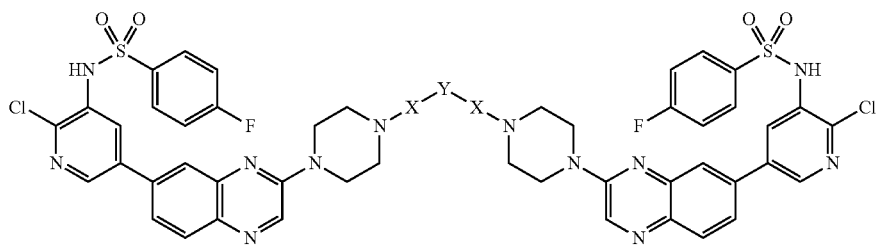

where Y = (CH$_2$CH$_2$O)$_n$ and n = 1-20
X = Z = null, CR$_1$R$_2$ (where R$_1$, R$_2$ = H, alkyl, phenyl or any combination), carbonyl, CONH, S=O, SO$_2$, SOCH$_2$, SO$_2$CH$_2$, SONH, SO$_2$NH or any combination.

Example 2

TABLE 7-continued

Examples of mono and bis-mTOR/PI3K inhibitors with lymph-directed targeting mEG moieties attached.

Mono and bis mTOR/PI3K Inhibitors

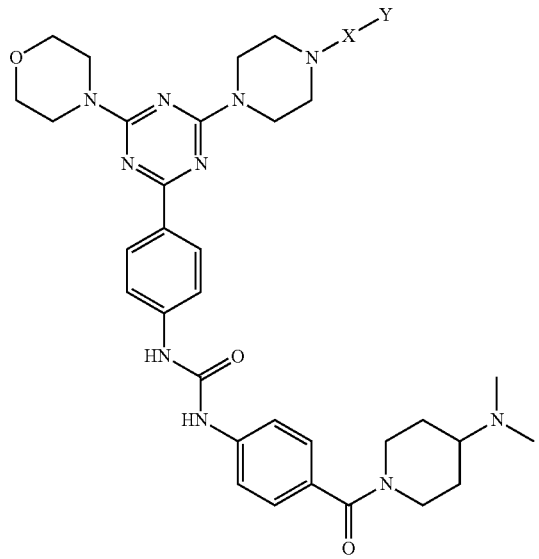

where Y = (CH$_2$CH$_2$O)R and n = 1-20 and R = H, alkyl, phenyl

X = null, CR$_1$R$_2$ (where R$_1$, R$_2$ = H, alkyl, phenyl or any combination), carbonyl, CONH, S=O, SO$_2$, SOCH$_2$, SO$_2$CH$_2$, SONH, SO$_2$NH or any combination.

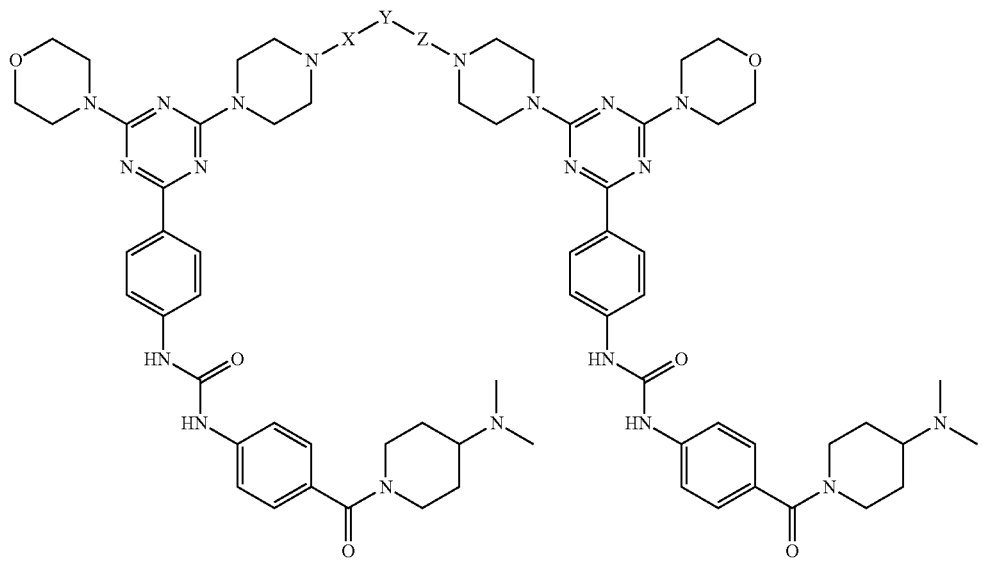

where Y = (CH$_2$CH$_2$O), and n = 1-20

X = Z = null, CR$_1$R$_2$ (where R$_1$, R$_2$ = H, alkyl, phenyl or any combination), carbonyl, CONH, S=O, SO$_2$, SOCH$_2$, SO$_2$CH$_2$, SONH, SO$_2$NH or any combination.

TABLE 8

Examples of JAK/MEK, JAK/mTOR and JAK/PI3K/mTOR Inhibitors with lymph-directed targeting mEG moieties/linkers attached

| Compound | Structure | Inhibitor Target |
|---|---|---|
| Cerdulatinib | 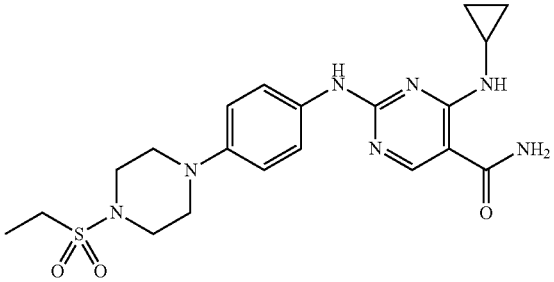 [SMILES: CCS(=O)(=O)N1CCN(c2ccc(Nc3ncc(C(N)=O)c(NC4CC4)n3)cc2)CC1] | JAK |
| A | 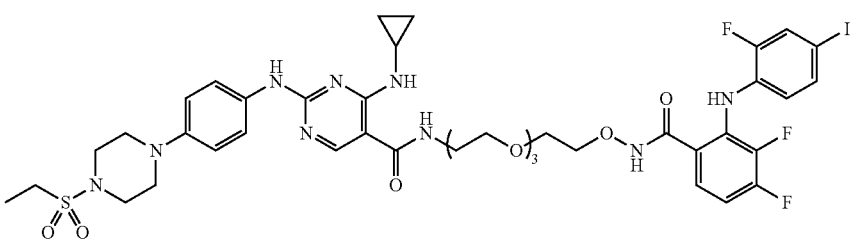 | JAK-MEK |
| B | 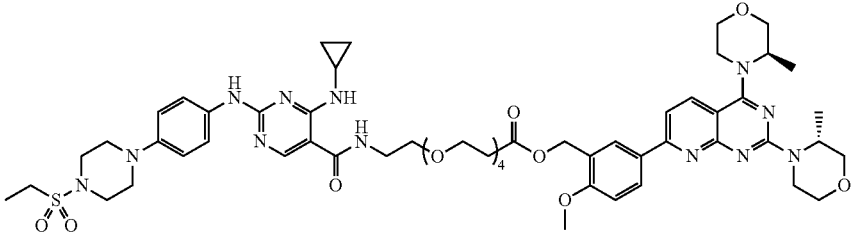 | JAK-mTOR |
| C | 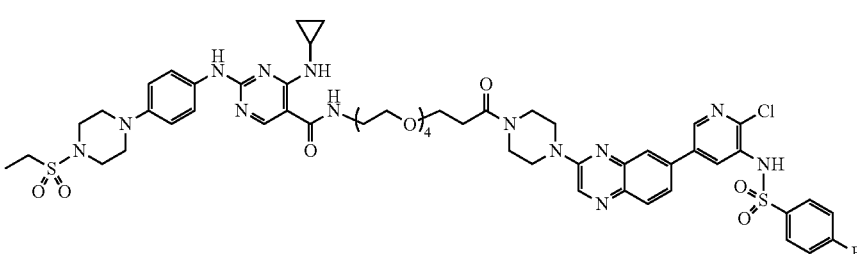 | JAK-PI3K/mTOR |

Multifunctional JAK Inhibitor Analogs (A, B, C) Shown in Table 8 are Obtained by Conjugation of the Prototype JAK Inhibitor Cerdulatinib with the MEK Inhibitor PD0325901 (Analog A), the mTOR Inhibitor AZD8055 (Analog B) or the PI3K/mTOR Inhibitor GSK458 (Analog C)

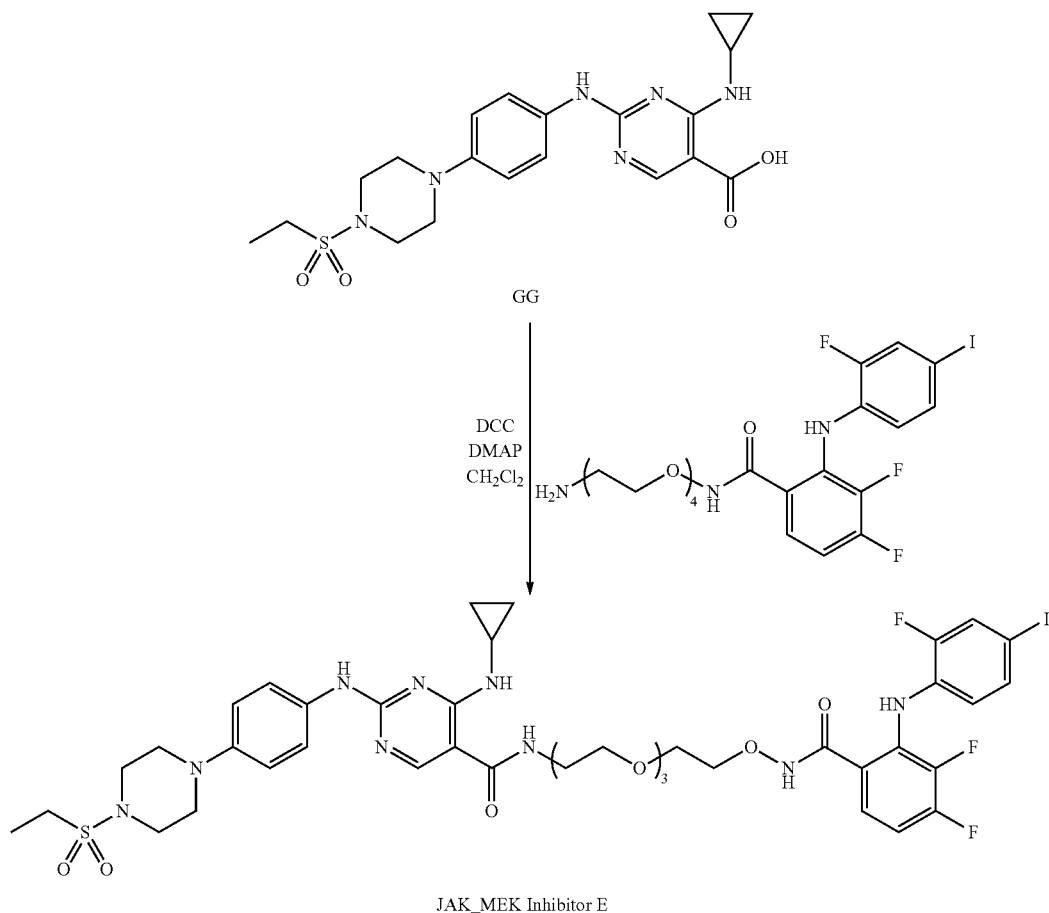

JAK_MEK Inhibitor E

Results from Additional Embodiments

Inhibitor compounds were synthesized to discover the underlying parameters needed in the development of chemical modifiers compatible with attachment to drug molecules to provide a drug having the physiochemical characteristics needed for uptake into the lymphatic system. Shown in Table 9, six different tool molecules (Compounds 1-6) or 3 pairs of structures (pairs 1-2, 3-4 and 5-6) with each of the three pairs differing only in the chemical linker (mEG or alkyl chain) were prepared. Compounds 1 through 4 shown in Table 9 were mixed with Maisine, an excipient material developed for oral delivery of molecules to humans. This excipient vehicle contains long chain fatty acids and is used for hydrophobic compound solubilization. A total of 10 mg of each of Compound 1-4 was added to 200 micro-liters of Maisine. Compounds 1 and 3 were completely solubilized in Maisine while Compounds 2 and 4 were incompletely solubilized as they were found to produce a white cloudy suspension. This data provides direct evidence of a unique chemical attribute provided by the short mEG chemical modifier, namely an improved solubility of a drug following attachment. Compounds 2 and 4 do not have sufficient solubility for complete dissolution at this dosage level, thus bioavailability is much more limited. This data revealed that alkyl chain moieties are not optimal for providing improved solubility of attached compounds and that mEG moieties are needed for this purpose. Each of the mixtures consisting of Compounds 1-4 was delivered orally to mice and tissues were harvested at time points 0.5, 2, and 4 hours post-administration to allow for quantification of compound concentrations in the host plasma, mesenteric lymph node, and mesenteric fat tissues using LC-MS/MS tissue analysis.

Effect of mEG Linker on c Log P.

As shown in Table 9, the overall impact of an mEG linker versus an alkyl linker was to significantly lower the overall molecular c Log P for a given end group moiety pair. For example, Compounds 1 and 2 had identical functional end groups consisting of a benzyl functional group. However, the mEG linker used in Compound 1 was determined to have a c Log P of only 1.6824 versus Compound 2 which was found to have a c Log P of 5.789. Likewise, Compounds 3 and 4 which had bis-naphthalene functional moieties linked to mEG and alkyl linkers, respectively revealed c Log P values of 4.0304 and 8.137, respectively. Furthermore, Compounds 5 and 6 which had bis-anthracene functional moieties linked to mEG and alkyl linkers, revealed c Log P values of 6.3784 and 10.485, respectively. Overall these results demonstrate that the presence of a mEG linker provides for significantly lower values of c Log P for a given identical structure compared to the use of an alkyl chain linker. When using a chemical linker to tether multiple molecules with limited solubility (relatively high c Log P), not only would the molecular weight increase but correspondingly the solubility could be significantly reduced making the compound impractical to solubilize for animal or human dose delivery, thus limiting its bio-absorption and tissue distribution.

TABLE 9
Compounds demonstrating the impact of an mEG versus alkyl linker on cLogP and lymphatic uptake in mice following oral administration.
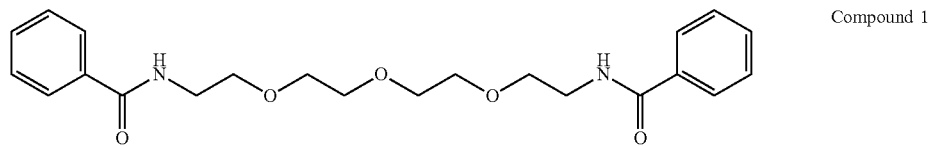
Compound 1
Log P: 1.64
tPSA: 85.89
CLogP: 1.6824
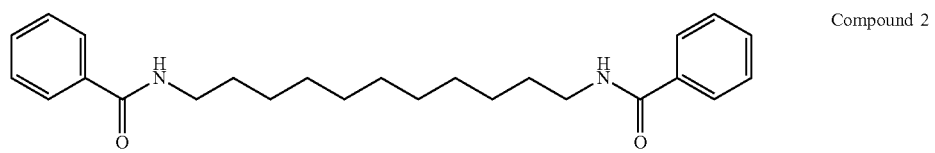
Compound 2
Log P: 5.59
tPSA: 58.2
CLogP: 5.789
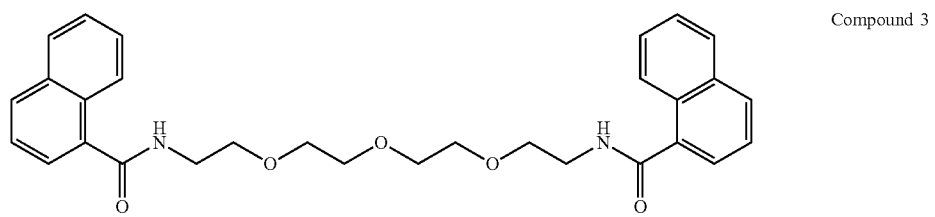
Compound 3
Log P: 3.64
tPSA: 85.89
CLogP: 4.0304
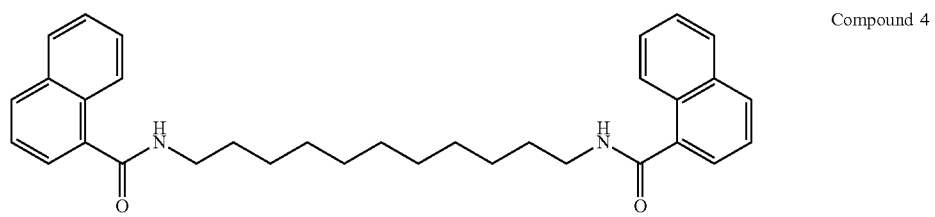
Compound 4
Log P: 7.58
tPSA: 58.2
CLogP: 8.137
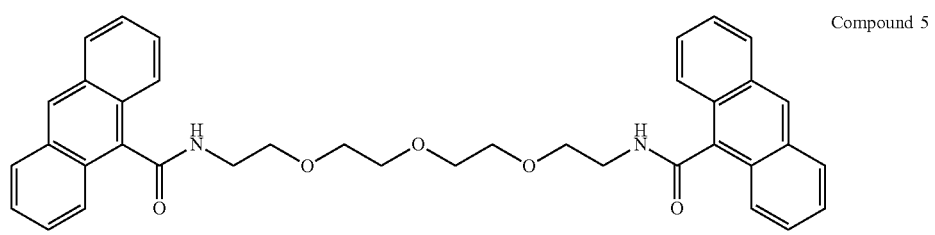
Compound 5
Log P: 5.63
tPSA: 85.89
CLogP: 6.3784

TABLE 9-continued

Compounds demonstrating the impact of an mEG versus alkyl linker on cLogP and lymphatic uptake in mice following oral administration.

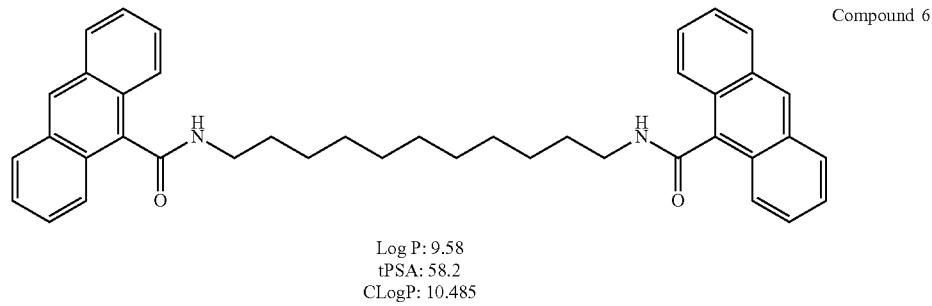

Compound 6

Log P: 9.58
tPSA: 58.2
CLogP: 10.485

Effect of Linker on Solubility.

Notably, Compounds 1 and 3 were completely solubilized in Maisine while Compounds 2 and 4 were not completely solubilized, but yielded a white cloudy suspension. Compound 4 had a lower solubility versus Compound 2, but neither compound was fully soluble. Furthermore, Compound 1 was completely soluble in Maisine, which is a triglyceride mixture, even though Compound 1 has a relatively low c Log P of 1.6824. This was an unexpected result because Compound 1 was not expected to be soluble based upon its oil/water ratio. In addition, another unexpected result was that Compounds 2 and 4 had very limited solubility in Maisine. Based upon c Log P, Compound 2 is expected to be completely soluble, while Compound 1 would not be expected to desolubilize in Maisine. The exact opposite was experimentally determined. Thus, the addition of a mEG linker, which is polar, conveyed solubility properties to these molecules in long chain fatty acid excipients (Maisine). This is an unexpected finding and points to features of mEG linkers in the context of linking relatively non-polar molecular compounds to convey solubility in unexpected solvents.

Effect of Linker on Tissue Concentration Partitioning.

Figure 2:
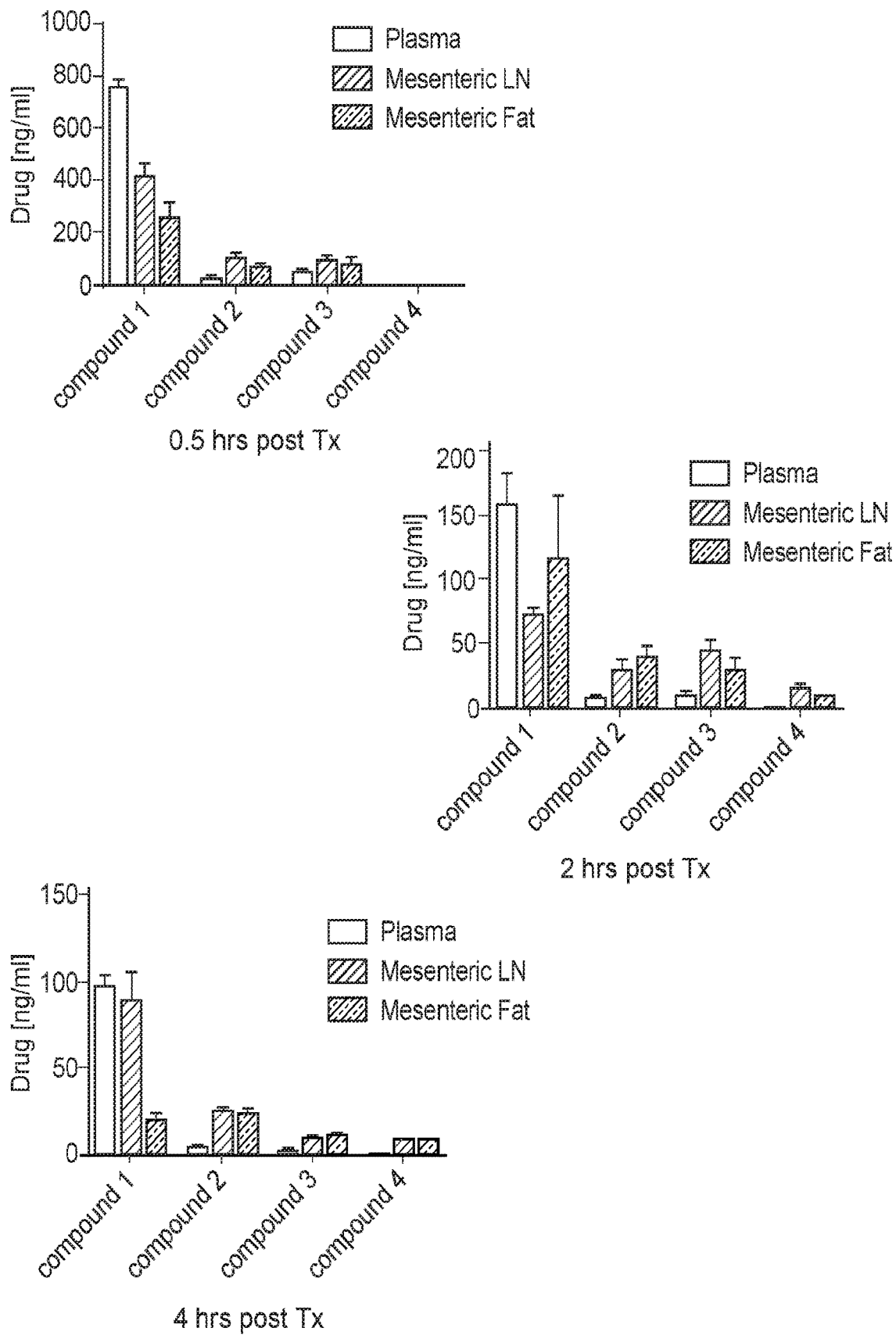
FIG. 2 contains bar graphs showing the effect of a present linker on tissue concentration partitioning.

Results from tissue sampling experiments from mice at three time points are provided in FIG. 2 for Compounds 1 through 4. FIG. 2 contains the results from mouse studies on Compounds 1 through 4 shown over time following a single oral administration of 10 mg of each compound in 200 microliters of excipient solvent Maisine followed by 100 microliters of water. Results were quantified using LC-MS/MS for plasma, mesenteric lymph node (LN) and mesenteric fat tissues.

Based upon current understanding, lymph-directed compounds are required to have a c Log P greater than five (c Log P>5) (Charman 1986). Compound 1 with a c Log P value of only 1.6824 would not be anticipated to partition into the lymphatic system. However, as shown in FIG. 2, Compound 1 was unexpectedly found to have a very significant lymph/plasma ratio of about 0.6 at 0.5 hours, which increased to about 1 at the 4 hour time point. Thus, Compound 1 has a high uptake into the lymphatic system following oral administration as demonstrated by the approximately 85 ng/ml lymphatic concentration of Compound 1 versus approximately 95 ng/ml in the plasma in the same animals at 4 hours post-dosing. This is an unexpected result because, according to current understanding, lymphatic partitioning is not anticipated to occur for Compound 1 due to the low c Log P value (c Log P=1.6824), which is far outside of the required hydrophobic value of greater than 5 for lymphatic transport.

Evaluation of Compound 2, which had the same structural benzene rings, revealed a higher relative lymph-directed uptake with lymph/plasma ratios of approximately 3-5 between time points 0.5, 2, and 4 hours. However, Compound 2 had much lower concentrations in all tissues tested presumably due to the much lower drug solubility due to the chemical nature of the alkyl linker and the higher c Log P value as compared to Compound 1. Compound 3, which has a c Log P value of 4.0304 and below the threshold for lymphatic transport (a requirement of c Log P>5), had a lymph/plasma ratio of approximately 5 at the 4 hour time interval which was similar to that of Compound 2. The difference in c Log P of Compound 2 and Compound 3 was −1.7586 (c Log P[Compound 3]–c Log P[Compound 2]). However, both compounds had similar lymph/plasma ratios following oral dosage. Compound 4 with a c Log P of 8.137 had the highest lymph/plasma ratio of approximately 6 at the 4 hour time point. While the high c Log P value conveys Compound 4 with a high level of lymphatic partitioning versus plasma, the lack of solubility makes compounds with high c Log P values impractical in terms of solubility, which limits bioabsorption and bioavailability in mammalian systems. The data in FIG. 2 reveal that the addition of an mEG linker modifier is critical for not only an ability to solubilize hydrophobic compounds, but also conveys physiochemical properties to allow for suitable formulation and provides unique characteristics for high lymphatic uptake.

A novel class of lymphatic-targeted compounds using a mEG linker modifier, which provides for improved solubility and lymphatic uptake, have been prepared. Nonlimiting examples of the present compounds are shown in Table 10, which were designed to simultaneously inhibit the RAS-RAF-MEK-ERK and PI3K-AKT-mTOR signaling pathways, in which clinical progress has been severely hampered due to significant systemic toxicities when single agent compounds are delivered as combination therapies. The examples of Table 10 show significant biological activity of a drug can be maintained with linkage to an mEG linker. Furthermore, Table 10 compounds have c Log P values ranging from 5.06-7.64. If an alkyl chain linker was substituted for an mEG linker of similar length, c Log P values would increase dramatically resulting in an inability to solubilize the compounds. Bioavailability therefor would be dose limiting making the compounds impractical as therapeutic agents. However, incorporation of mEG linker modifiers onto the chemical structures of drugs allows sufficient solubility to be maintained or even improved and provides the physiochemical required for the modified compound to undergo lymphatic absorption following administration.

TABLE 10A

| Compound | Structure |
| --- | --- |
| ST-180 | 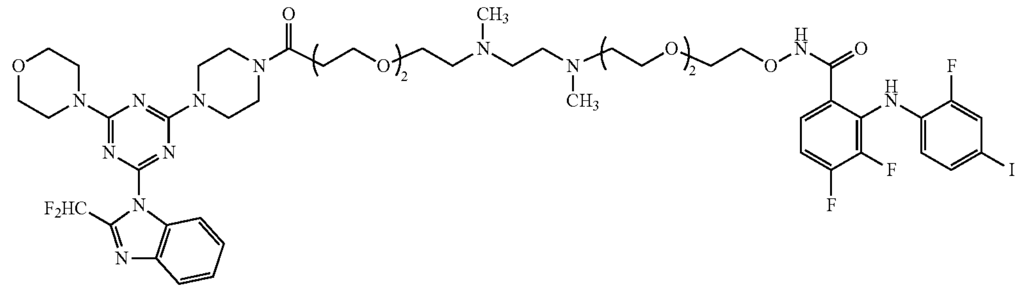 |
| ST-182 | 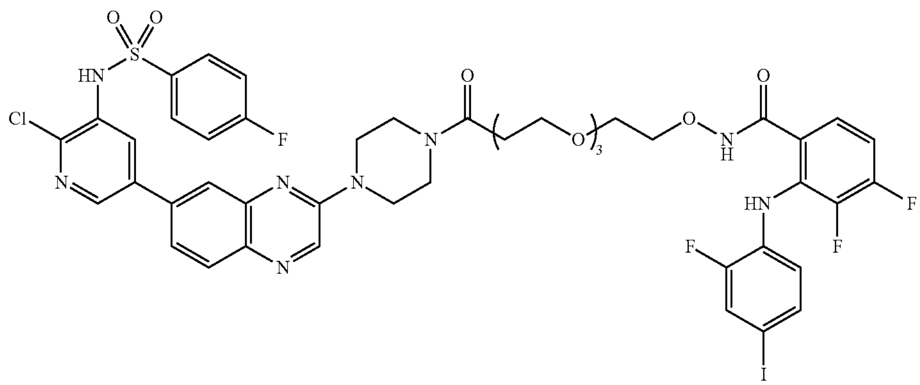 |
| ST-185 | 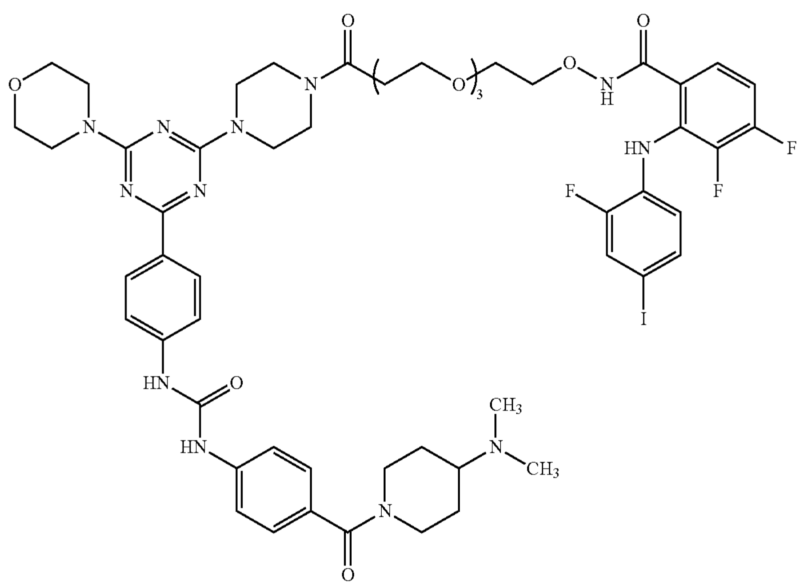 |
| ST-162 | 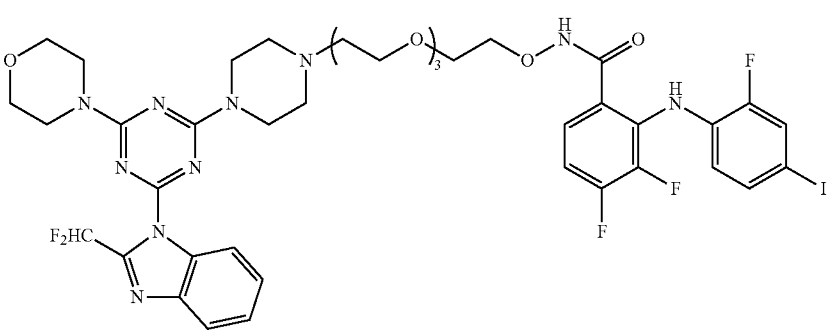 |

TABLE 10A-continued

| Compound | Structure |
|---|---|
| ST-168 | 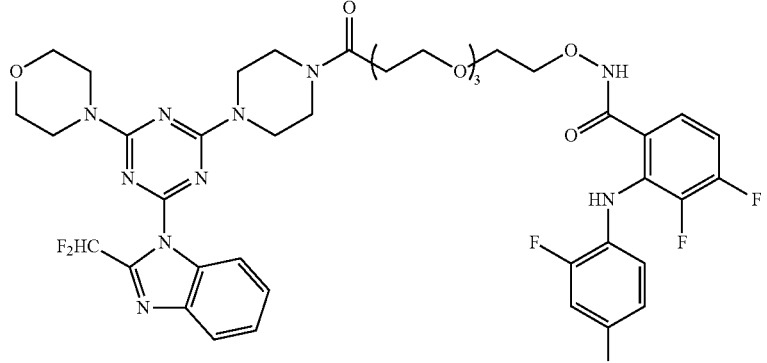 |

TABLE 10B

| Compound | clog P | mTOR | PI3Kα | PI3Kβ | PI3Kγ | PI3Kδ |
|---|---|---|---|---|---|---|
| ST-180 | 6.47 | n.a. | 39 ± 9 | 2215 ± 425 | 717 ± 136 | 52 ± 1.4 |
| ST-182 | 7.64 | 53.1 ± 2.5 | 2.0 ± 0.3 | 467 ± 44 | 34.1 ± 3.0 | 4.22 ± 0.64 |
| ST-185 | 5.49 | 50.4 ± 4.2 | 42.3 ± 4.0 | 1617 ± 442 | 325 ± 78 | 55.3 ± 3.9 |
| ST-162 | 5.71 | n.a. | 191 ± 64 | 4073 ± 290 | 5803 ± 511 | 942 ± 120 |
| ST-168 | 5.06 | n.a. | 69.2 ± 2.2 | 1482 ± 377 | 2293 ± 241 | 41.7 ± 2.1 |

Compounds based upon the mEG lymphatic directed strategy (Table 10A) allows solubilization, as well as lymphatic-directed absorption, following administration. Table 10B provides values for c Log P and individual inhibitory activities of cellular targets.

Demonstration of the effects of the chemical modifier methodology by attachment of a mEG moiety to a therapeutic drug is shown in FIG. 3. LC-MS/MS quantification of drug concentrations in mouse tissues over time following a single oral dose is shown. FIG. 3 contains block diagrams for formulations in ORA-Plus liquid particulate suspension: FIG. 3A compound ST-168 levels at 4 hours in plasma and lymphatic tissue versus the MEK inhibitor PD0325901 (henceforth referred to as PD901). FIG. 3B ST-168 time dependence in plasma and lymphatic tissue, and formulated in Maisine, FIG. 3C ST-168 time dependence in plasma and lymphatic tissue following 100 mg/kg dose. FIG. 3D shows ST-168 time dependence in plasma and lymphatic tissue following 400 mg/kg dose.

In a series of experiments, the ability of the chemical linker to improve lymphatic drug uptake was demonstrated. In FIG. 3, LC-MS/MS quantification of drug concentrations in mouse tissues over time are shown following a single oral suspension dose of ST-168 delivered in ORA-Plus®. ORA-Plus is an aqueous-based vehicle (ORA-Plus Product Data Sheet available at Perrigo Company's website) containing a synergistic blend of suspending agents having a high degree of colloidal activity. The suspending agents form a structured, gel-like matrix which suspends particles and allow for little settling. ORA-Plus is buffered to a slightly acidic pH to help reduce degradation of medicinal agents through oxidation. The ORA-Plus contains purified water, microcrystalline cellulose, carboxymethylcellulose sodium, xanthan gum, carrageenan, calcium sulfate, trisodium phosphate, citric acid and sodium phosphate as buffers and dimethicone antifoam emulsion, preserved with methylparaben and potassium sorbate. Suspension of a compound in this formulation for oral dosing does not facilitate lymphatic transport because it is an aqueous-based excipient formulation. Any compound delivered in ORA-Plus is distributed to the plasma and lymphatic system based upon the physiochemical properties of the drug. Thus, the formulation itself only serves to provide for a suspension of drug particulates and dissolution of drug will be based upon water solubility.

Figure 3A:
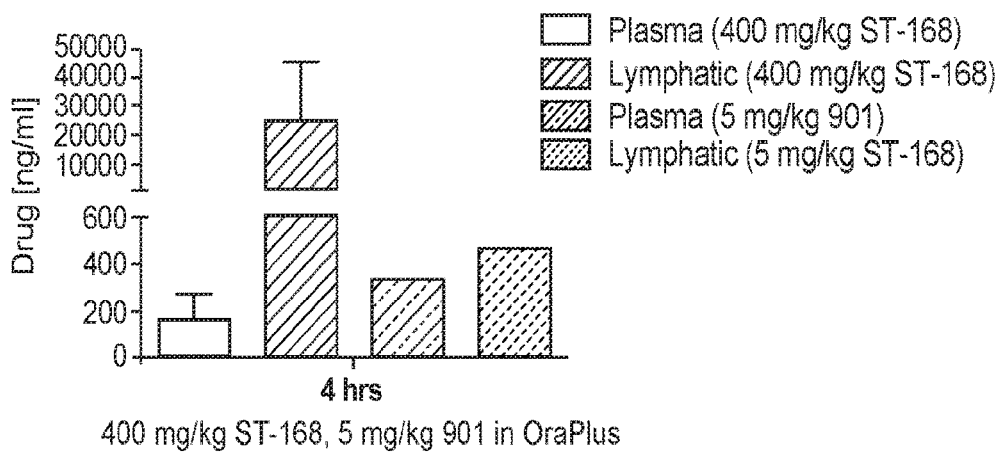
FIG. 3A, FIG. 3B, FIG. 3C, and FIG. 3D are bar graphs showing concentrations in mouse tissue following a single oral dose of compound ST-168.
Figure 3B:
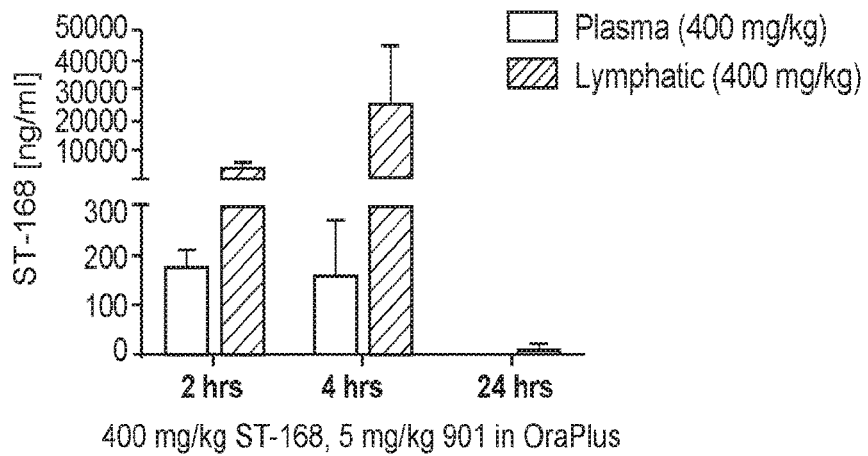
Figure 3C:
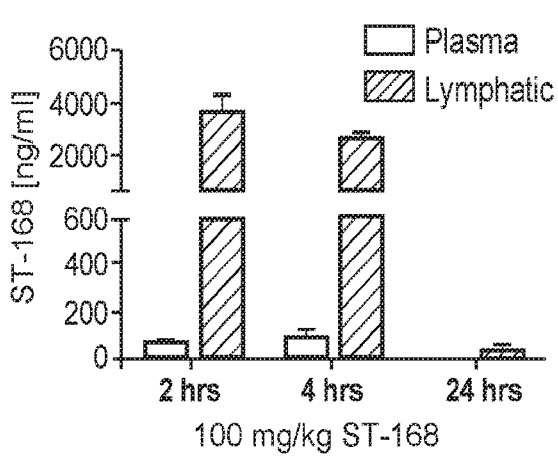
Figure 3D:
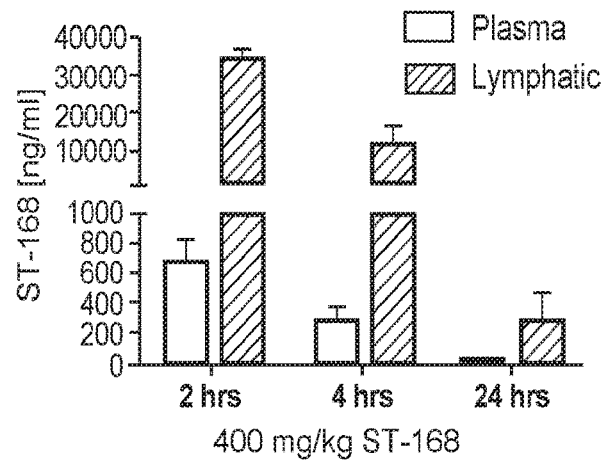

Shown in FIG. 3A, the uptake profile of Compound 901 into the plasma and lymphatic system reveals a lymphatic/plasma ratio of approximately 1.2 at 4 hours post-administration. The impact of attachment of a mEG linker modifier to a compound for improving solubility and lymphatic uptake is shown in FIG. 3A, where attachment of a mEG linker to Compound PD0325901 and attaching the other end of the linker to another targeted inhibitor (PI3K) (Compound ST-168 in Table 10) was found to increase the lymphatic/plasma ratio to approximately 120. Moreover partitioning of ST-168 between lymphatic/plasma is maintained over a 24 hour time period (FIG. 3B) following a single oral dose of 400 mg/kg in ORA-Plus excipient, which delivered ST-168 in the form of a compound suspension. This is an important distinction showing that Compound ST-168 has lymphatic absorptive properties because ORA-Plus is not a long chain fatty acid like Maisine. When Maisine is used, ST-168 was completely solubilized at the concentrations used (8 mg/200 microliters) and examples of tissue concentration levels over a 24 hour time frame (2, 4, and 24 hour) for single oral doses of 100 mg/kg (FIG. 3C) and 400 mg/kg (FIG. 3D) in Maisine changes are consistent with extraordinarily high lymphatic uptake. Data presented in FIGS. 3A through 3D reveal that the mEG linker technology for chemical coupling with drugs produces solubility properties consistent with formulation and bioavailability required for drug-like pharmaceutical characteristics and improved lymphatic absorption.

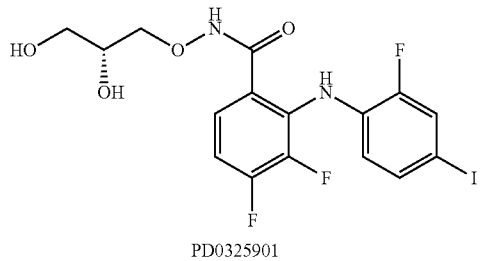 [SMILES: O=C(NOC[C@H](O)CO)c1ccc(F)c(F)c1Nc1ccc(I)cc1F]

PD0325901

Figure 4:
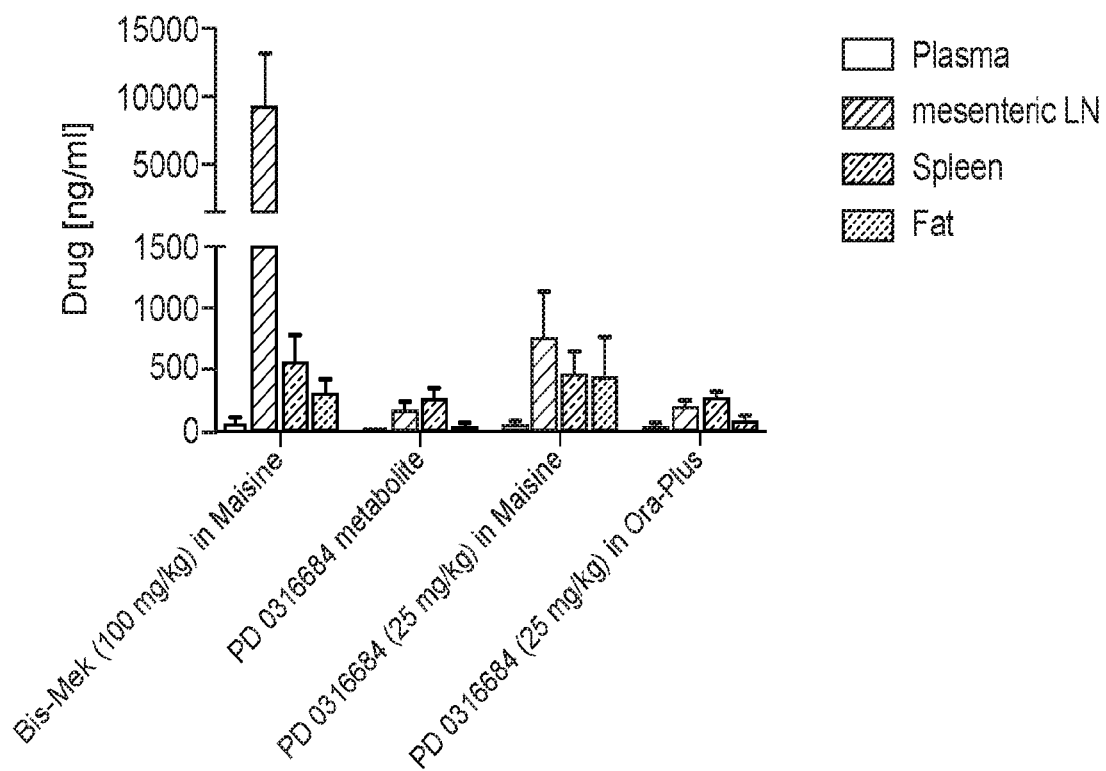
FIG. 4 contains graphs showing concentrations in mouse tissue following a single oral dose of compound ST-162, ST-168, and a control.
Figure 4:
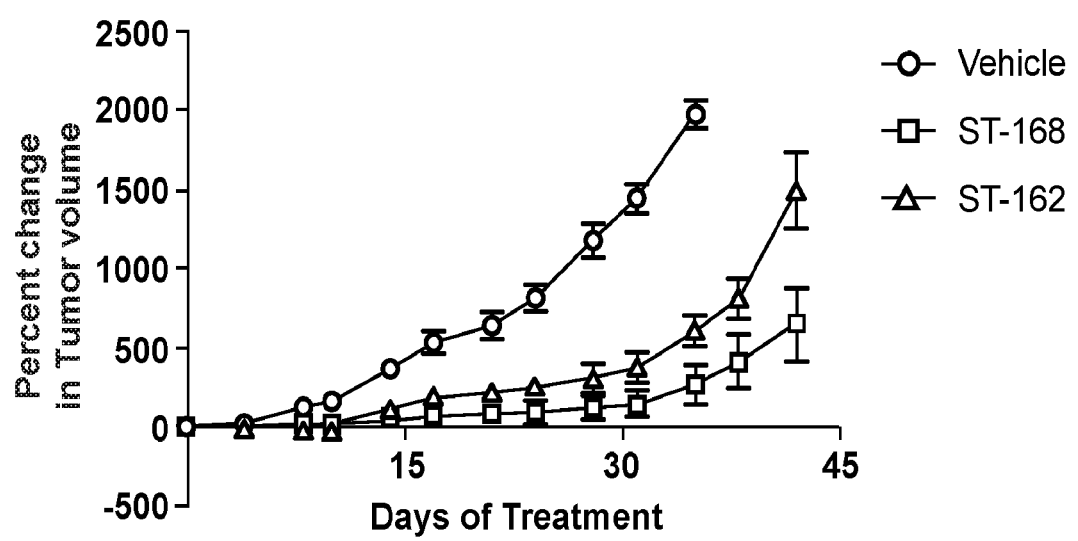

FIG. 4 shows the LC-MS/MS quantification of drug concentrations in mouse tissues over time following a single oral dose administration to a control and compounds ST-168 and ST-162 samples acquired at 4 hours post dosing. Formulations in ORA-Plus liquid particulate suspension or Maisine are shown for comparison: (Left to right) Bis-MEK compound shows high levels of lymphatic drug uptake at 4 hours. PD0316684 (an alternate high-affinity MEK inhibitor) metabolic breakdown product of Bis-MEK is shown. Comparisons also are provided for Maisine and Ora Plus formulations for PD0316684 for levels in plasma, mesenteric lymph node tissue, spleen and fat. Note that the linked Bis-MEK compound with the lymphatic-targeting linker yielded extremely high levels of compound within the lymphatic tissue.

Efficacy of ST-168 in Cancer Models.

Figure 5A:
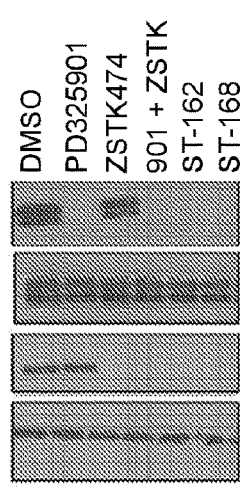
FIG. 5A, FIG. 5B, and FIG. 5C illustrate the target activity of compounds ST-162 and ST-168 in cells.
Figure 5B:
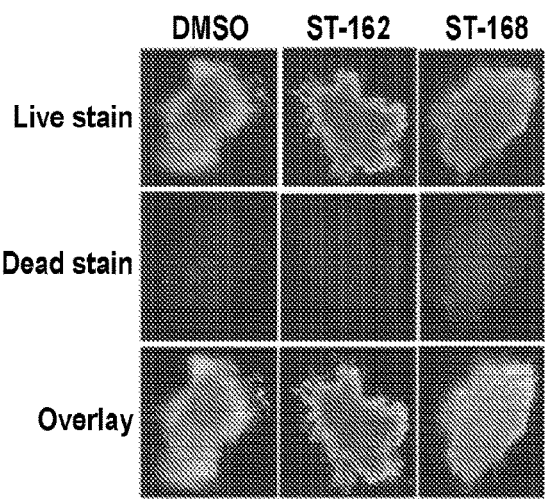
Figure 5C:
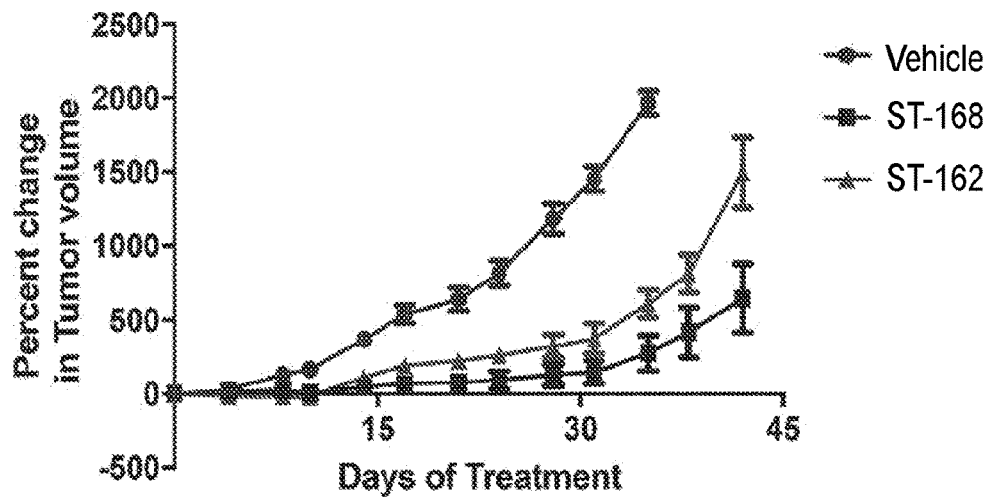

FIGS. 5A through 5C illustrates results from cell incubation studies of Compound 4 (ST-162) and Compound 7 (ST-168) showing their cellular permeability ability and ability to down regulate their intended therapeutic targets of pERK1/2 and pAKT. Treatment of colorectal, glioma, and melanoma mouse xenograft models show tolerance of ST-168 at doses of 400 mg/kg administered orally suspended in ORA-Plus with no observed toxicities. ADME (absorption, distribution, metabolism, and excretion) studies of ST-168 have shown that ST-168 is bioavailable following administration in mice. Mice with subcutaneously implanted human A374 melanoma tumors were treated with vehicle, Compound 4 (ST-162) or Compound 7 (ST-168) at 400 mg/kg for 30 days followed by maintenance therapy using 200 mg/kg for the subsequent 14 days. FIGS. 5A through 5C show a comparison of the efficacy of the two compounds which reveals that both ST-168 and ST-162 achieve tumor stasis for the initial 30 days.

In particular, FIGS. 5A through 5C shows the target activity of bifunctional inhibitors ST-162 and ST-168 in cells, 3D melanoma spheroids, and in vivo mouse models. In FIG. 5A, a two-dimensional assessment of ST-162 and ST-168. Immunoblot analysis of A375 melanoma cells treated for 1 h with PD0325901 (10 μM), ZSTK474 (10 μM), a combination of PD0325901 and ZSTK474 (10 μM each), ST-162 (20 μM), or ST-168 (20 μM) and compared to equimolar concentrations of DMSO control. Phosphorylation of ERK1/2 and AKT at serine 473 was used to define activities of MEK1 and PI3K, respectively. In FIG. 5B, assessment of dead cells in 3D melanoma spheroids post-treatment with ST-162 and ST-168. A375 melanoma spheroids were treated for 72 h with 20 μM each of ST-162 or ST-168 before staining with Calcein AM and ethidium homodimer-1 for fluorescence microscopy (live/dead viability assay, Molecular Probes). Green fluorescence indicates live cells, and red fluorescence indicates dead cells. Images were obtained with an Olympus IX70 fluorescent microscope using the SPOT advance program. In FIG. 5C tumor growth inhibition by ST-162 and ST-168 in a melanoma xenograft model. Tumor implantation consisted of inoculation of $5 \times 10^6$ A375 cells suspended in 100 μL of media into the flank of nude mice. Treatment was initiated once tumors reached >100 mm$^3$. Mice were randomized into two treatment groups and treated once daily with either vehicle (200 μL of OraPlus) or 400 mg/kg each of ST-162 or ST-168 by oral gavage until sacrifice (42 days). Changes in tumor growth of A375 xenografts were assessed by conducting MRI imaging twice per week. Tumor volume changes between ST-162 and ST-168 treatment were determined to be statistically significant ($p<0.05$) using an unpaired Student's t test at the last time point. Experimental design: n=4-6 tumors/treatment group. This data demonstrates the superior in vivo activity of bifunctional inhibitor ST-168 compared to ST-162 for suppression of MEK1/PI3K kinase activities in vivo in solid tumors.

The biopharmaceutical classification system (BCS) was introduced and is considered an important tool for regulation of drug products world-wide (Lindenberg, Kopp et al. 2004). Orally administered drugs on the Model list of Essential Medicines of the World Health Organization (WHO) are assigned BCS classifications on the basis of data available in the public domain. For the 130 orally administered drugs on the WHO list, 61 drugs are classified with certainty. Twenty-one (84%) of these belong to class I (highly soluble, highly permeable), 10 (17%) to class II (poorly soluble, highly permeable), 24 (39%) to class III (highly soluble, poorly permeable), and 6 (10%) to class IV (poorly soluble, poorly permeable) (Lindenberg, Kopp et al. 2004). An additional 28 drugs were provisionally assigned, while for 41 drugs insufficient or conflicting data precluded assignment to a specific BCS class. A total of 32 class I drugs (either certain or provisional classification) were identified.

Many drugs have a known and significant first pass effect (metabolism in the liver), degradation in the GI-tract, poor permeability, poor solubility, and overall less than optimal bioavailability. Attachment of a lymphatic linker provides needed chemical and biological modifications to enhance drug bioavailability, biological half-life, and overall effectiveness of many different compounds across clinical disease and drug target classes. As shown in Table 11, increasing the length of the lymphatic targeting moiety results in a reduction of the compounds c Log P value. Examples of additional applications include attachment of drugs that target lymphocytes, thus the immune system, as well as clearing the lymphatic system, lymphatic organs, and lymph nodes, from either primary and/or metastatic spread of tumor cells by redirection of targeted inhibitors into the lymphatic system. This can be accomplished using a single lymph-directed compound or a combination of lymphatically-targeted drugs depending upon the disease are of interest. Attachment of a lymph-targeting linker, which can be biologically removed, can be achieved by attachment to drug functionalities including for example nonlimiting carboxylic acid esters, hydroxyl, sulfhydryl, phosphates, amine, amide, and carbonyl. Some specific examples of drugs are listed in Table 4. Additional nonlimiting linker-modified drugs are listed in Table 12, which are examples of approved drugs having substituents that can be readily modified with a lymphatic-targeting moiety for improving lymphatic uptake. Additional drugs can be modified for example from the list of Essential Medicines, as defined by the World Health Organization (WHO), as well as other drugs, including investigational compounds.

TABLE 11
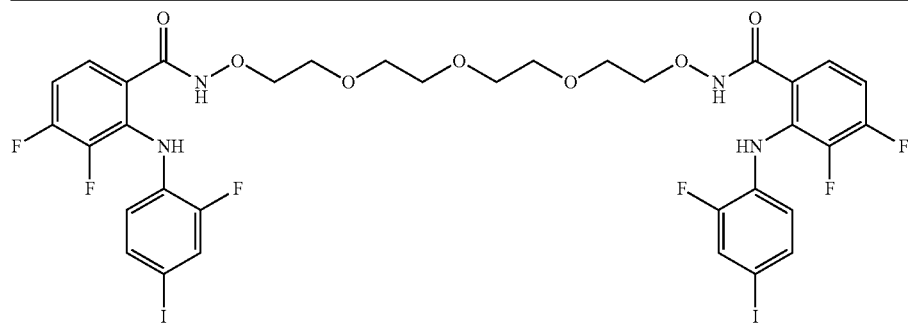
Log P: 8.62
tPSA: 128.41
CLogP: 8.4409
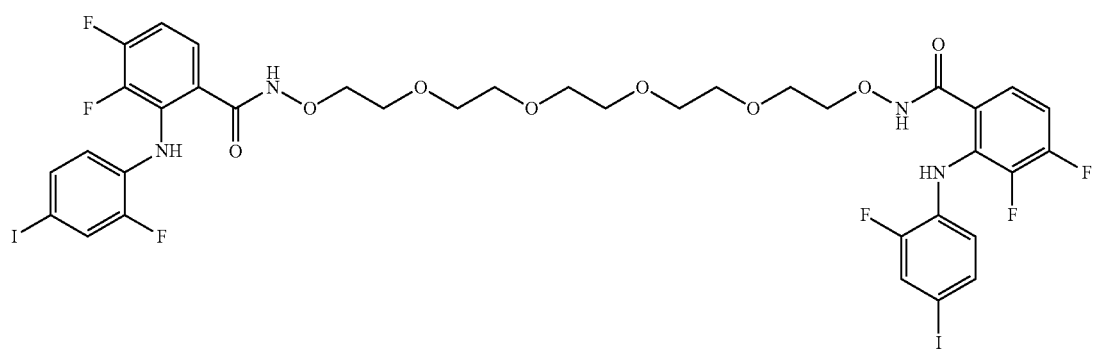
Log P: 8.47
tPSA: 137.64
CLogP: 8.2653
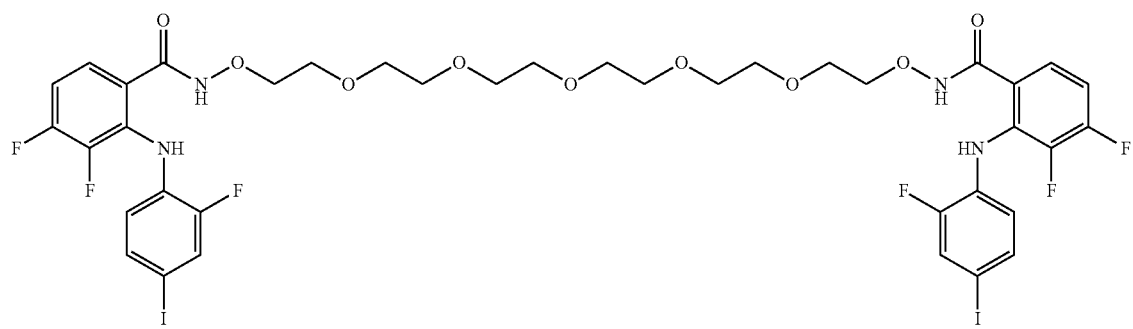
Log P: 8.31
tPSA: 146.87
CLogP: 8.0897
Table 11 contains examples of mEG-linker modified Bis(PD 0316684) MEK inhibitors showing the impact of the mEG length on c Log P of a drug.
TABLE 12
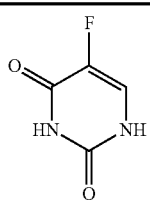
Flourouracil
TABLE 12-continued
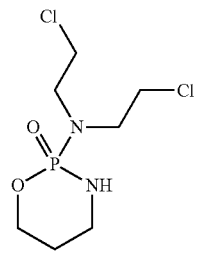
Cyclophosphamide

TABLE 12-continued

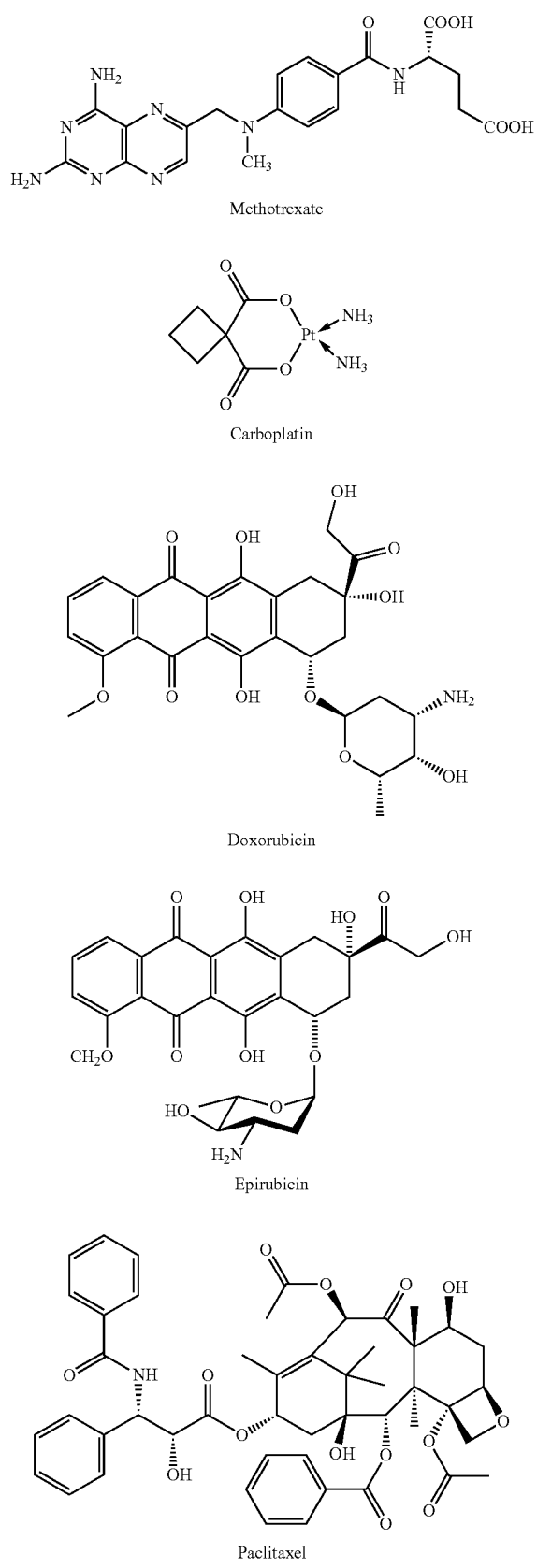

Methotrexate

Carboplatin

Doxorubicin

Epirubicin

Paclitaxel

TABLE 12-continued

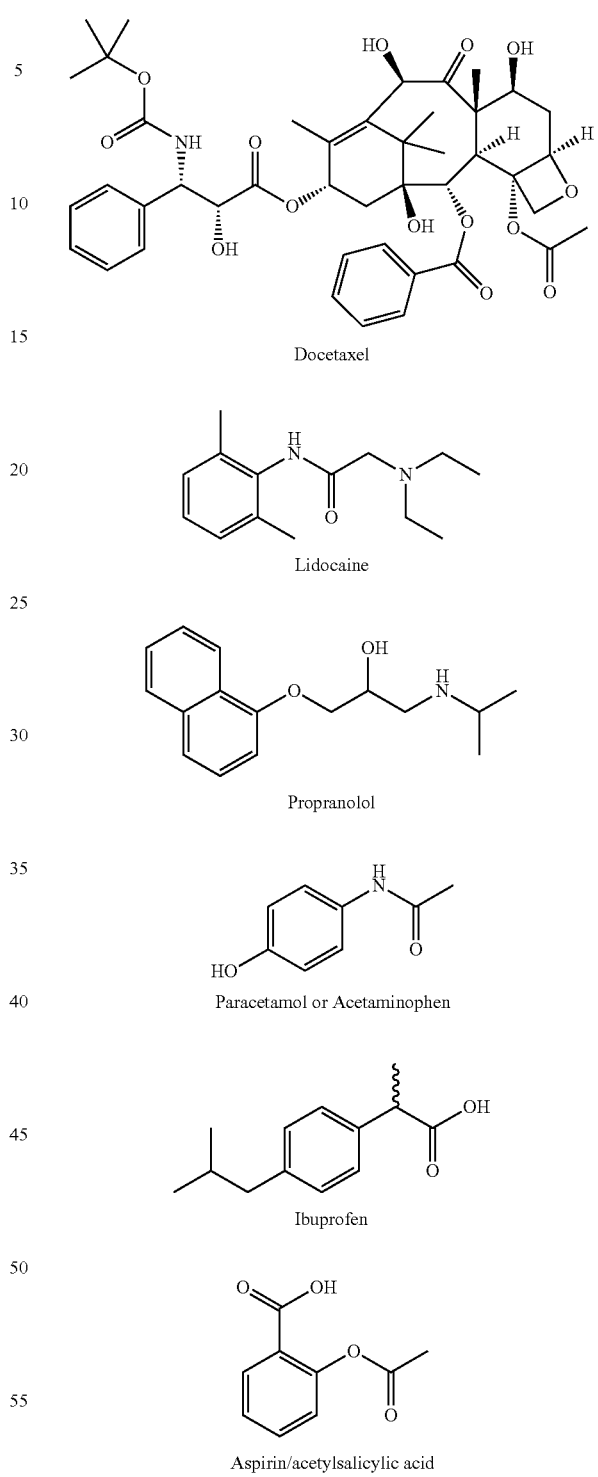

Docetaxel

Lidocaine

Propranolol

Paracetamol or Acetaminophen

Ibuprofen

Aspirin/acetylsalicylic acid

The examples in Table 12 are a subset of approved and marketed drugs having a functional substituent wherein attachment of lymphatic-targeting moieties can be used to enhance lymphatic uptake. In these examples, the targeting linker can be prepared to biologically detach after administration and following lymphatic uptake to release the parent drug as shown in Table 4.

The following are nonlimiting, novel mTOR_MEK and mTOR_PI3K Targeting Prodrugs/Inhibitors.

AZD8055 is a small molecule ATP-competitive, dual mTORC1/mTORC2 inhibitor (IC$_{50}$=0.8 nM) having excellent selectivity towards the Class 1 PI3K isoforms (>1 μM). AZD2014 is a second generation dual mTOR inhibitor (IC$_{50}$=2.8 nM) with similar PI3K selectivity, which additionally shows superior liver metabolic stability compared to AZD8055. The design and synthesis of a new dual mTOR_MEK inhibitor (ST-65) based on the AZD8055 core structure and the MEK inhibitor PD0316684 was undertaken for initial biological studies.

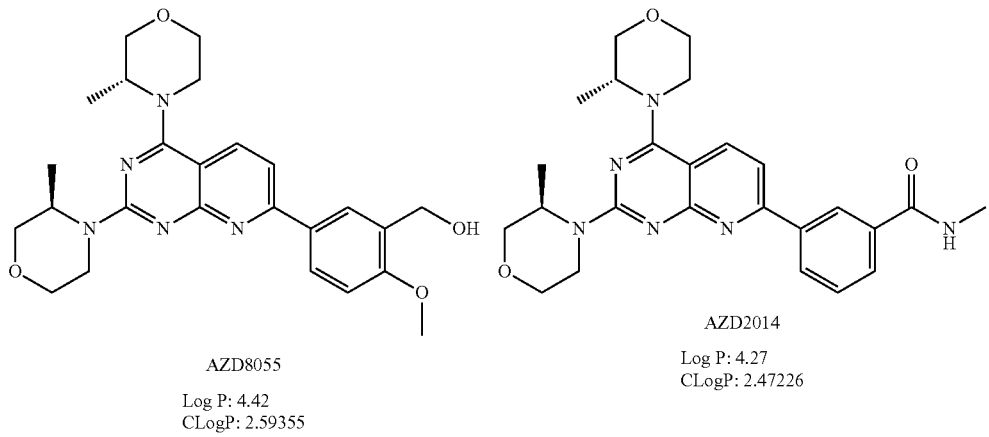

AZD8055
Log P: 4.42
CLogP: 2.59355

AZD2014
Log P: 4.27
CLogP: 2.47226

Synthesis of ST-65

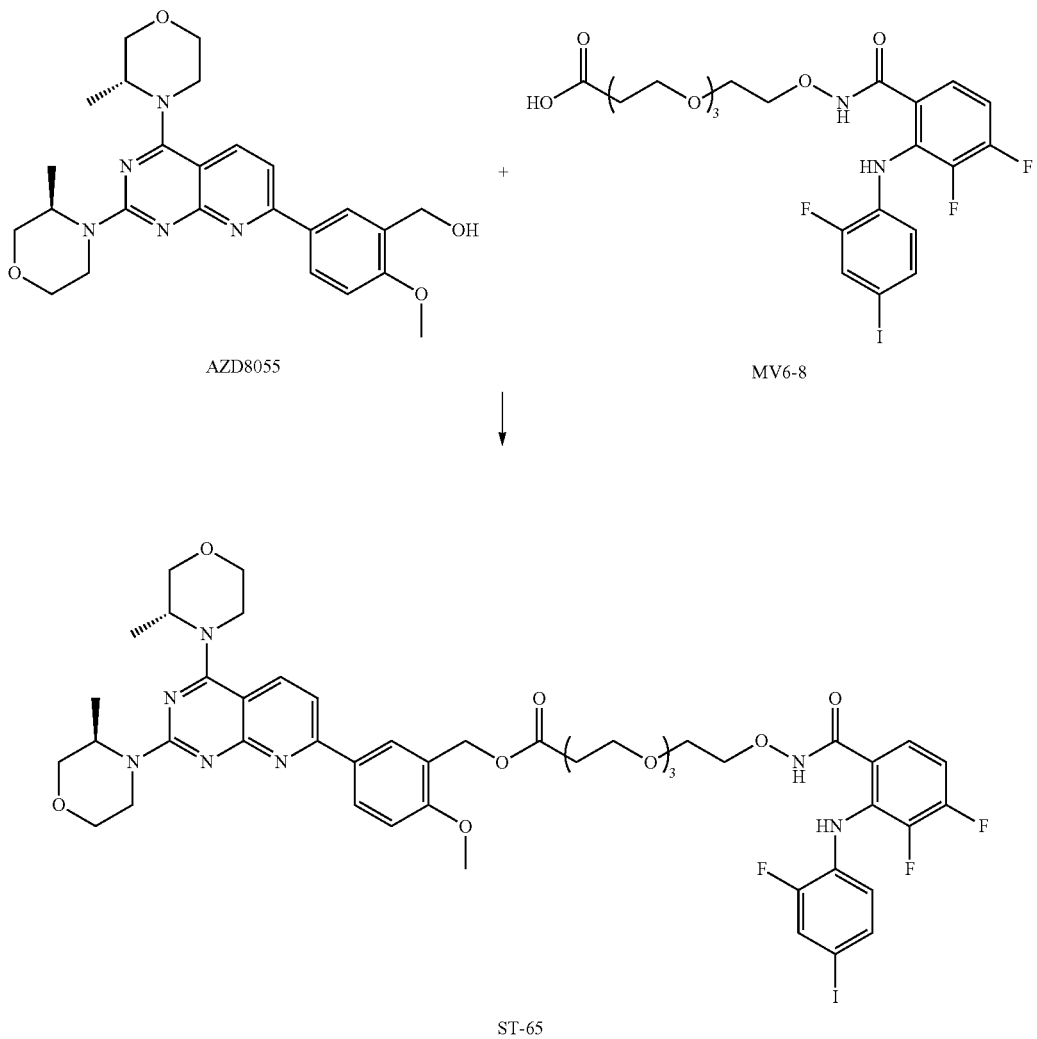

AZD8055

MV6-8

ST-65

A stirred mixture of AZD8055 (700 mg, 1.14 mmol), MV6-8 (530 mg, 1.14 mmol) in anhydrous dichloromethane (DCM) was cooled to 0° C. with an ice-bath under a nitrogen atmosphere and treated with dicyclohexylcarbodimide (258 mg, 1.25 mmol) and dimethylaminopyridine (14 mg, 0.11 mmol). The mixture was allowed to warm to ambient temperature and stirred overnight under nitrogen. The precipitated dicyclohexylurea was removed by filtration, the residue rinsed with ice-cold DCM, and the filtrate was concentrated under vacuum. The crude product was chromatographed thrice with a solvent gradient of 2%-6% $CH_3OH$ in DCM with 1% added $NH_4OH$ to give 447 g (37% yield) of ST-65. HPLC analysis shows 99.2% purity ($t_R$=16.7 min). HRMS (ESI$^+$): m/z calculated for $C_{47}H_{54}F_3IN_7O_{10}$ (M+H$^+$), 1060.2923. Found 1060.2925.

| | $IC_{50}$ (nM) | |
|---|---|---|
| Compound | mTOR | MEK1 |
| AZD 8055 | 1.07 ± 0.12 | N/A |
| MV6-8 | N/A | 72.3 ± 1.9 |
| ST-65 | 40.5 ± 2.2 | 83.2 ± 4.5 |

A) mTOR Prodrugs/Inhibitors with AZD8055 Core Structure and mEG Ester Linkers

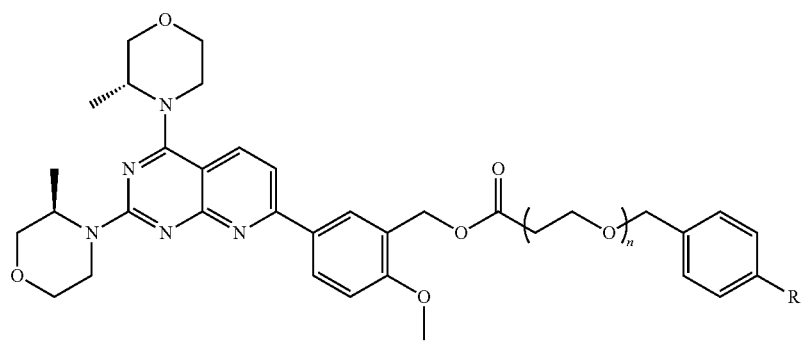

AZD8055 containing Core Structure

| Compound | | n | R | clog P |
|---|---|---|---|---|
| AZD8055 | | n/a | n/a | 2.59 |
| 1 | | 3 | H | 4.89 |
| 2 | | 3 | $CH_3$ | 5.39 |
| 3 | | 3 | $CH_3CH_2$ | 5.92 |
| 4 | | 3 | isopropyl | 6.32 |
| 5 | | 3 | tert-butyl | 6.72 |
| 6 | | 4 | $CH_3$ | 5.21 |
| 7 | | 4 | $CH_3CH_2$ | 5.74 |
| 8 | | 4 | isopropyl | 6.14 |
| 9 | | 4 | tert-butyl | 6.54 |

(n = 3 – 12)

B) mTOR Inhibitors with AZD8055 Core Structure and mEG Alkyl Linkers
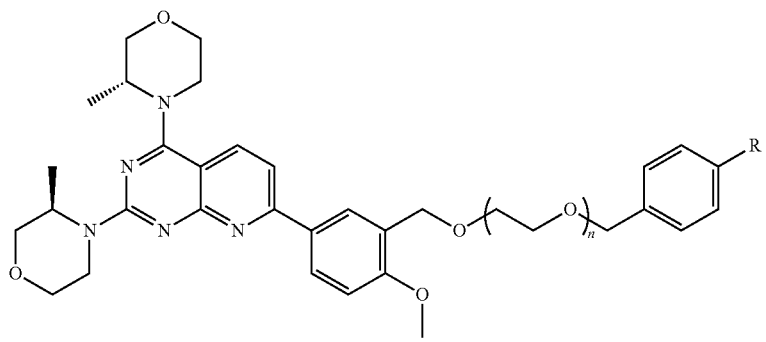
AZD8055 containing Core Structure
| Compound | n | R | clog P |
|---|---|---|---|
| 10 | 3 | H | 4.53 |
| 11 | 3 | $CH_3$ | 5.03 |
| 12 | 3 | $CH_3CH_2$ | 5.56 |
| 13 | 3 | isopropyl | 5.96 |
| 14 | 3 | tert-butyl | 6.36 |
| 15 | 4 | $CH_3CH_2$ | 5.38 |
| 16 | 4 | isopropyl | 5.78 |
| 17 | 4 | tert-butyl | 6.18 |
(n = 3 – 12)
C) mTOR Inhibitors with AZD2014 Core Structure and mEG amide Linkers
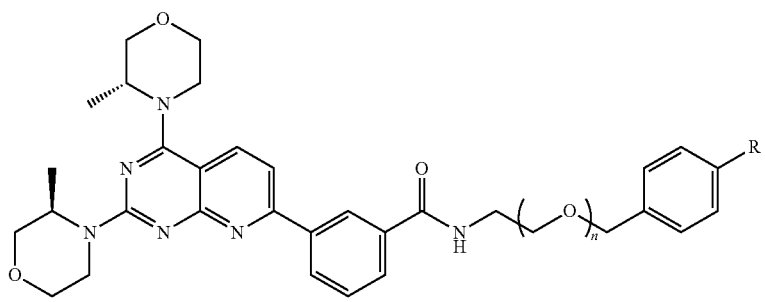
AZD2014 containing Core Structure
| Compound | n | R | clog P |
|---|---|---|---|
| | n/a | n/a | 2.47 |
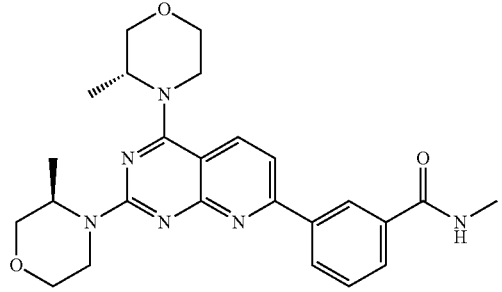
AZD2014
| | | | |
|---|---|---|---|
| 18 | 3 | $CH_3CH_2$ | 5.09 |
| 19 | 3 | isopropyl | 5.49 |
| 20 | 3 | tert-butyl | 5.89 |

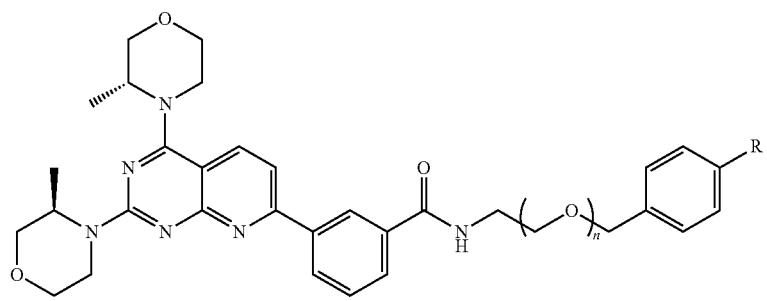
AZD2014 containing Core Structure
| Compound | n | R | clog P |
|---|---|---|---|
| 21 | 4 | $CH_3CH_2$ | 4.91 |
| 22 | 4 | isopropyl | 5.31 |
| 23 | 4 | tert-butyl | 5.71 |
(n = 3-6)
D) mTOR Inhibitors with AZD2014 Core Structure and mEG Amine Linkers
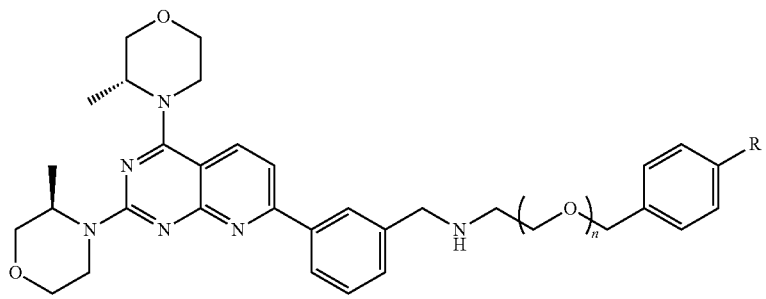
AZD2014 containing Core Structure
| Compound | n | R | clog P |
|---|---|---|---|
| 24 | 3 | $CH_3CH_2$ | 5.57 |
| 25 | 3 | isopropyl | 5.97 |
| 26 | 3 | tert-butyl | 6.37 |
| 27 | 4 | $CH_3CH_2$ | 5.40 |
| 28 | 4 | isopropyl | 5.80 |
| 29 | 4 | tert-butyl | 6.20 |
(n = 3-6)

E) Bivalent mTOR Inhibitor Prodrugs (AZD8055 Core Structure)
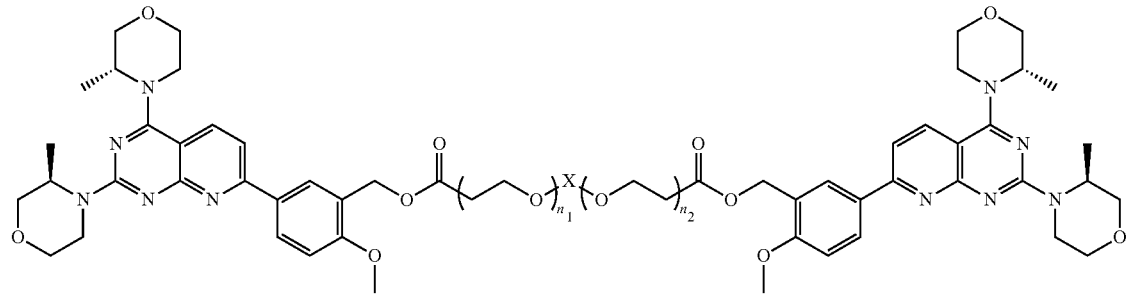
AZD8055 containing Core Structure
| Compound | | $n_1$ | $n_2$ | X | clog P |
|---|---|---|---|---|---|
| AZD8055 | (structure shown) | n/a | n/a | n/a | 2.59 |
| 30 | | 1 | 1 | —(C(=O)—O—C(=O))— | 6.74 |
| 31 | | 2 | 2 | —(C(=O)—O—C(=O))— | 6.38 |
| 32 | | 1 | 1 | —(C(=O)—CH$_2$—C(=O))— | 6.98 |
| 33 | | 3 | 3 | —(C(=O)—CH$_2$—C(=O))— | 6.26 |
| 34 | | 1 | 1 | *—(C(=O)—CH$_2$CH$_2$—C(=O))—* | 7.33 |
| 35 | | 4 | 4 | *—(C(=O)—CH$_2$CH$_2$—C(=O))—* | 6.25 |
($n_1$ and $n_2$ can vary from 1-10 or any combination)

F) Bivalent mTOR Inhibitors (AZD2014 Core Structure)
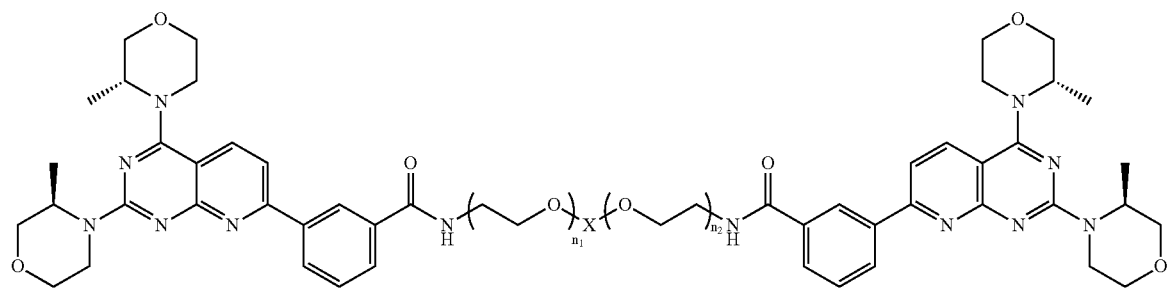
AZD2014 containing Core Structure
| Compound | $n_1$ | $n_2$ | X | clog P |
|---|---|---|---|---|
| | 1 | 1 | n/a | 2.47 |
| 36 | 1 | 1 | −(C(=O)−O−C(=O))− | 5.03 |
| 37 | 1 | 1 | −(C(=O)−CH$_2$−C(=O))− | 5.27 |
| 38 | 2 | 2 | −(C(=O)−CH$_2$−C(=O))− | 4.91 |
| 39 | 1 | 1 | *−(C(=O)−CH$_2$CH$_2$−C(=O))−* | 5.63 |
| 40 | 2 | 2 | *−(C(=O)−CH$_2$CH$_2$−C(=O))−* | 5.27 |
($n_1$ and $n_2$ can vary from 1-3 or any combination)

G) Bivalent mTOR Inhibitors (AZD8055 Core Structure) with mEG Linkers
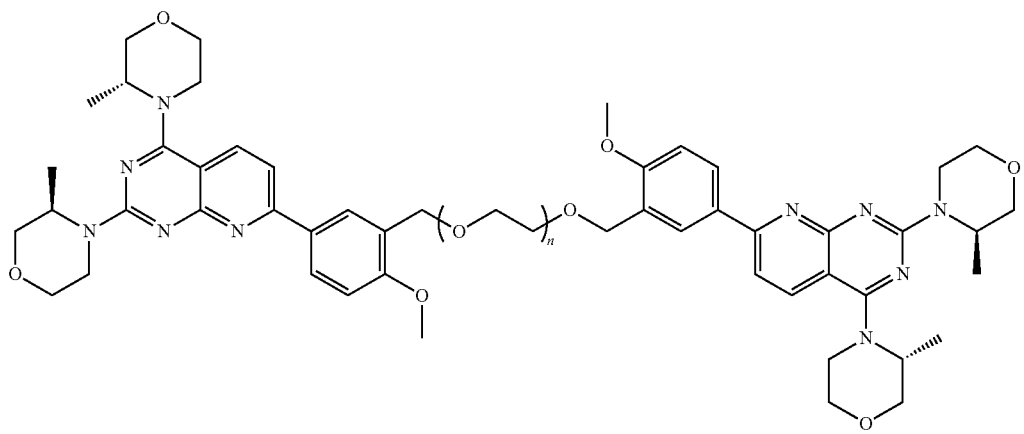
AZD8055 containing Core Structure
| Compound | n | clog P |
|---|---|---|
| 41 | 2 | 6.20 |
| 42 | 3 | 6.02 |
| 43 | 4 | 5.84 |
| 44 | 5 | 5.66 |
(n = 3-8)
H) Bivalent mTOR Inhibitors (AZD2014 Core Structure) with mEG Linkers
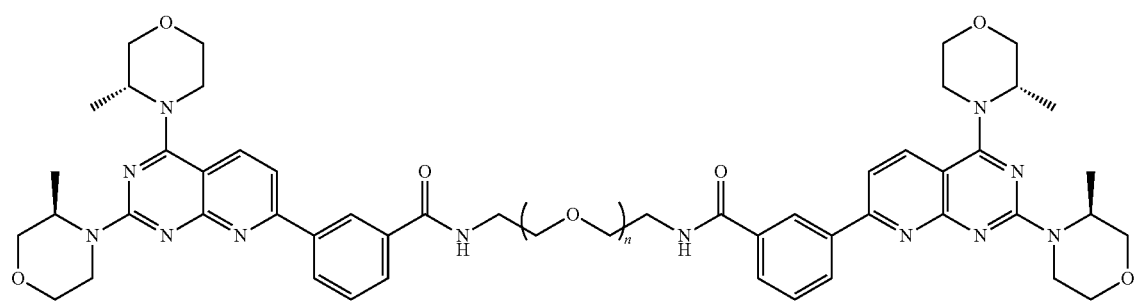
AZD2014 containing Core Structure
| Compound | n | clog P |
|---|---|---|
| 45 | 1 | 5.20 |
| 46 | 2 | 5.03 |
| 47 | 3 | 4.90 |
n = 1-3)

I) mTOR_MEK Targeting Bifunctional Inhibitors/Prodrugs with AZD8055 Core Structure
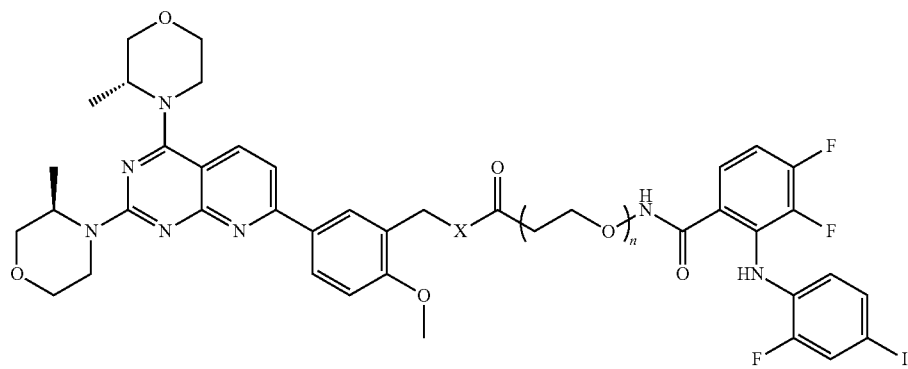
AZD8055 (mTOR) and PD0316684 (MEK) containing Core Structures
| Compound | X | n | clog P |
|---|---|---|---|
| 48 | O | 3 | 7.68 |
| 49 (ST-65) | O | 4 | 7.50 |
| 50 | O | 5 | 7.33 |
| 51 | NH | 3 | 6.93 |
| 52 | NH | 4 | 6.75 |
| 53 | NH | 5 | 6.58 |
(n = 3-15)
J) mTOR_MEK Targeting Bifunctional Inhibitors with AZD2014 Core Structure
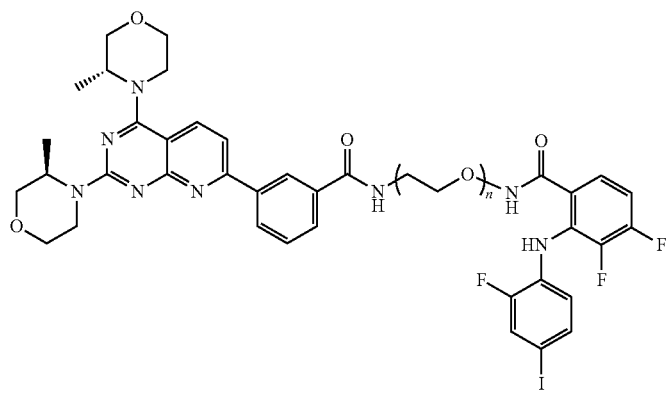
AZD2014 (mTOR) and PD0316684 (MEK) containing Core Structures
| Compound | n | clog P |
|---|---|---|
|  | n/a | 2.47 |
AZD2014

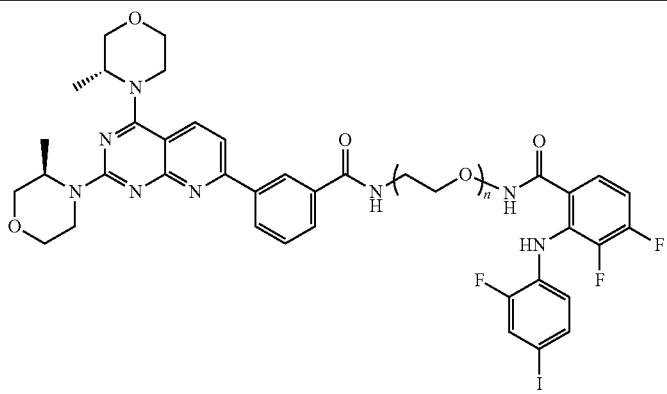
AZD2014 (mTOR) and PD0316684 (MEK) containing Core Structures
| Compound | n | clog P |
|---|---|---|
| 54 | 3 | 6.85 |
| 55 | 4 | 6.67 |
| 56 | 5 | 6.50 |
(n = 3-15)
K) mTOR Targeting Prodrugs Linked to the 2-Position of Triglycerides
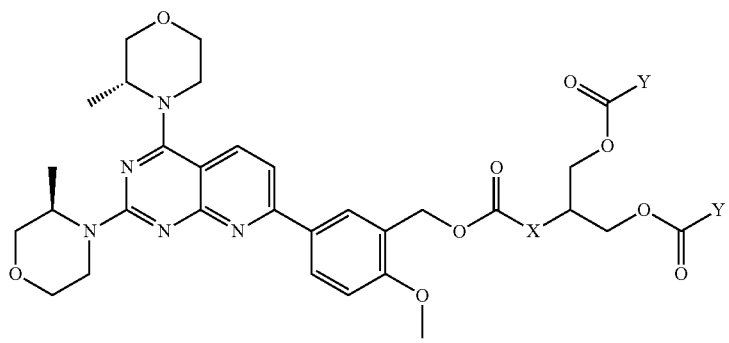
AZD8055 containing Core Structure
| Compound | X | Y | clog P |
|---|---|---|---|
|  | n/a | n/a | 2.59 |
AZD8055

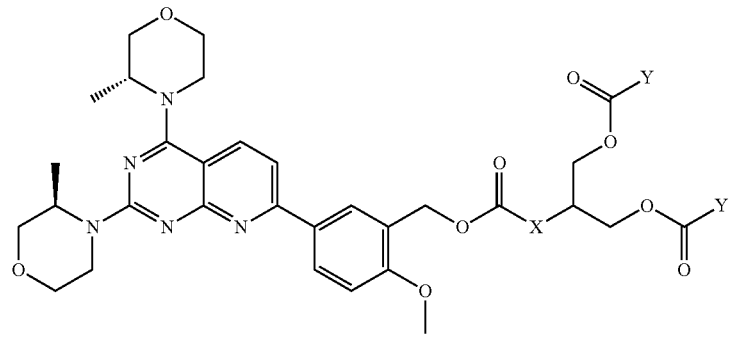
AZD8055 containing Core Structure
| Compound | X | Y | clog P |
|---|---|---|---|
| 57 | CH$_2$ | CH$_3$ | 4.48 |
| 58 | CH$_2$ | C$_2$H$_5$ | 5.53 |
| 59 | CH$_2$ | C$_3$H$_7$ | 6.60 |
| 60 | CH$_2$ | C$_5$H$_{11}$ | 8.71 |
| 61 | —O— | CH$_3$ | 3.56 |
| 62 | —O— | C$_2$H$_5$ | 4.62 |
| 63 | —O— | C$_3$H$_7$ | 5.68 |
| 64 | —O— | C$_4$H$_9$ | 6.73 |
| 65 | —O— | C$_5$H$_{11}$ | 7.79 |

L) mTOR Targeting Prodrugs Linked to the 2-Position of Triglyceride Core Structure
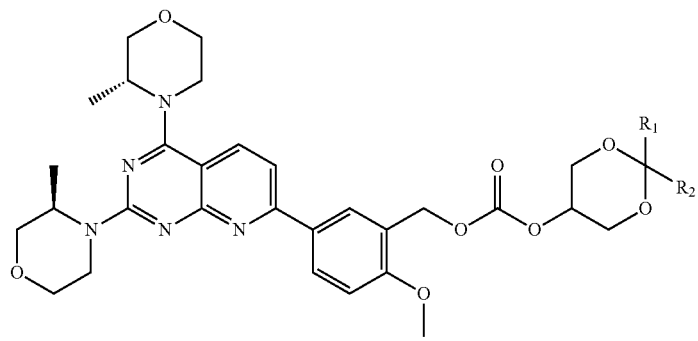
AZD8055 containing Core Structure
| Compound | R₁ | R₂ | clog P |
|---|---|---|---|
| AZD8055 | n/a | n/a | 2.59 |
| 66 | CH₃ | CH₃ | 4.17 |
| 67 | C₂H₅ | C₂H₅ | 5.22 |
| 68 | C₃H₇ | C₃H₇ | 6.28 |
| 69 | phenyl | CH₃ | 5.21 |
| 70 | phenyl | phenyl | 6.24 |
General Synthetic Route to Compounds 66-70 Above
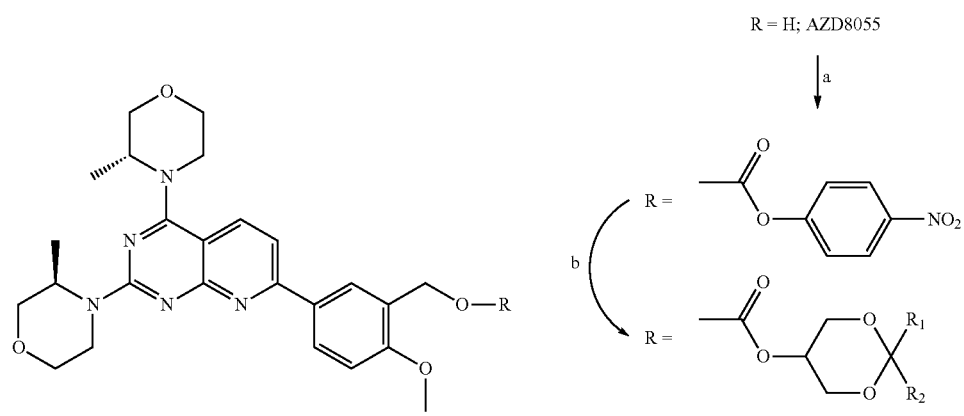
Reagents and conditions: (a) 4-nitrophenyl chloroformate, Et₃N, DCM;
(b) 1,3-dioxan-5-ol analog, Et₃N, DMAP, THF.

M) PI3K Targeting Inhibitors with ZSTK474 Core Structure and mEG Linkers

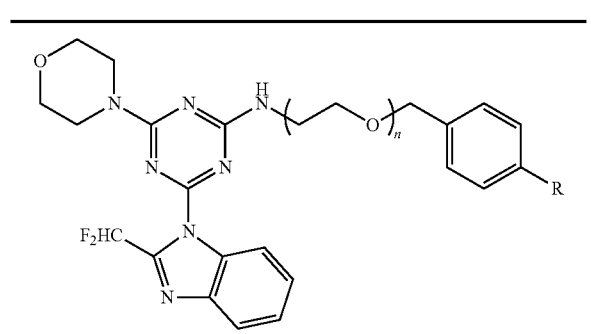

ZSTK474 containing Core Structure

| Compound | n | R | clog P |
|---|---|---|---|

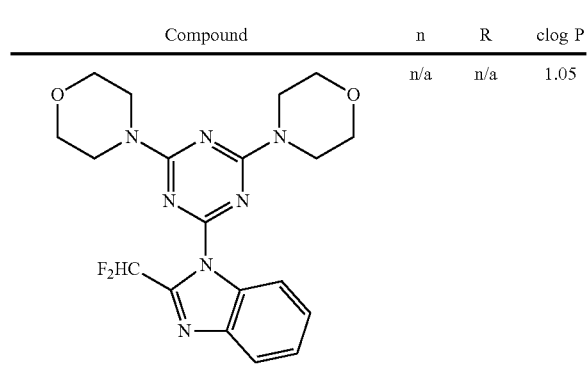

ZSTK474

| | n/a | n/a | 1.05 |

-continued

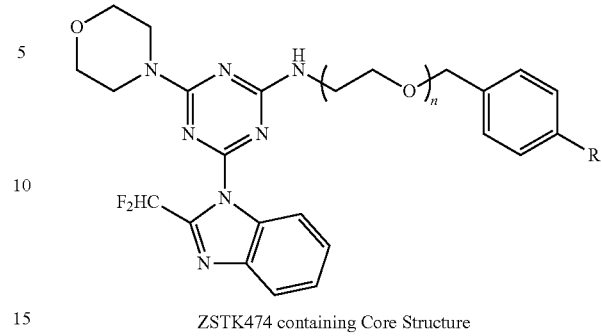

ZSTK474 containing Core Structure

| Compound | n | R | clog P |
|---|---|---|---|
| 71 | 3 | isopropyl | 4.54 |
| 72 | 3 | tet-butyl | 4.94 |
| 73 | 4 | isopropyl | 4.36 |
| 74 | 4 | tert-butyl | 4.76 |

N) mTOR/PI3K Targeting Inhibitors with Alkyl Bonded mEG Linkers (GSK458 Core Structure)

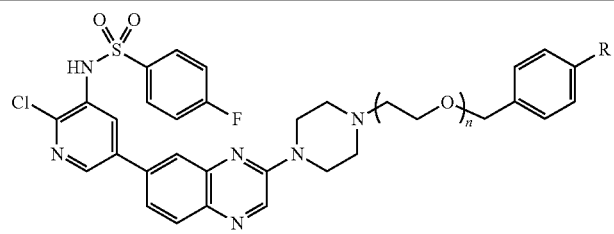

GSK458 type Core Structure with alkyl mEG Linker

| Compound | n | R | clog P |
|---|---|---|---|
| | n/a | n/a | 4.07 |

GSK458

| 75 | 3 | H | 5.44 |
| 76 | 3 | CH$_3$ | 6.02 |
| 77 | 4 | H | 5.26 |

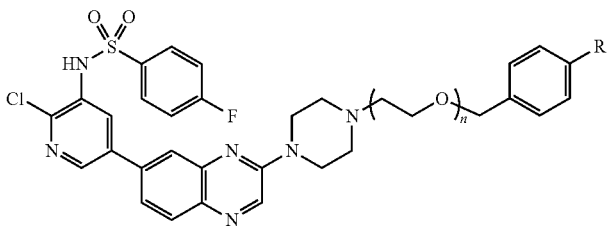

GSK458 type Core Structure with alkyl mEG Linker

| Compound | n | R | clog P |
|---|---|---|---|
| 78 | 4 | CH₃ | 5.84 |
| 79 | 4 | isopropyl | 6.77 |
| 80 | 4 | tert-butyl | 7.17 |

(n = 3-15)

O) mTOR/PI3K Targeting Inhibitors with Amide Bonded mEG Linkers (GSK458 Core Structure)

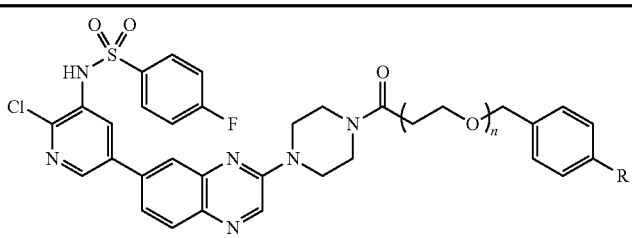

GSK458 type Core Structure with amide mEG Linker

| Compound | n | R | clog P |
|---|---|---|---|
| GSK458 | n/a | n/a | 4.07 |
| 81 | 3 | H | 5.02 |
| 82 | 3 | CH₃ | 5.52 |
| 83 | 4 | isopropyl | 6.28 |
| 84 | 4 | tert-butyl | 6.67 |

(n = 3-15)

Figure 6:
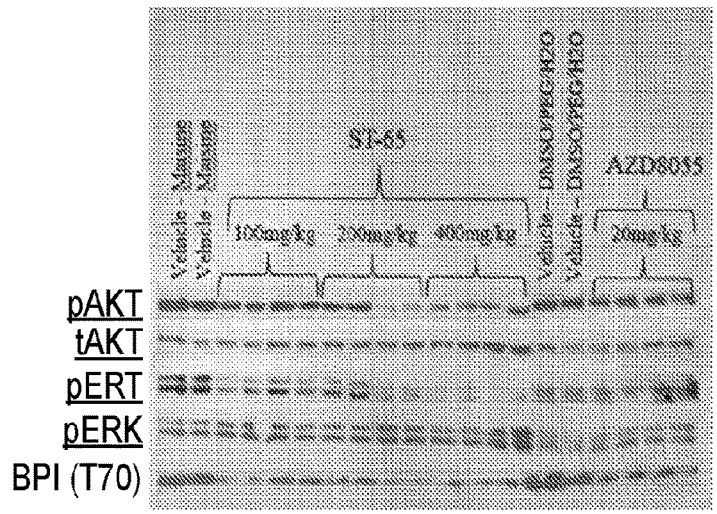
FIG. 6 contains Western blot analysis of tumor tissues from mice treated with a single oral dose of ST-65.

Treatment of a subcutaneously implanted A2058 melanoma cancer model was accomplished with a single oral dose of ST-65, followed by tumor tissue analysis at 4 hours by Western blot. In particular, FIG. 6 contains Western blots of tumor tissues analyzed from mice bearing subcutaneously implanted melanoma tumors. Mice received a single oral dose (100, 200 or 400 mg/kg) of ST-65 and were sacrificed for tissue analysis 4 hours later. Vehicle controls also were provided for comparison, as well as mice treated with a known mTOR inhibitor, AZD8055. As shown in the Western blot, a dose-dependent decrease in pAKT and pERK was detected.

These studies showed that ST-65 was highly active in a living mouse against its MEK/mTOR targets. ST-65 provides for a wide range of therapeutic indications including for example cancer, pulmonary diseases (IPF, COPD), fibrotic and inflammatory disorders (including autoimmune diseases), chronic pain, neurodegenerative diseases including, for example, MS and Alzheimer's disease.

A prototype mTOR/MEK inhibitor prodrug (ST-65), which also functions as a bifunctional inhibitor, has been developed for lymphatic targeting. ST-65 was synthesized by covalent linking of the potent mTOR inhibitor AZD 8055 and the MEK1 inhibitor PD0316684 via a multi-PEG (mEG) linker attachment. ST-65 (c Log P=7.50) displays high lymphatic targeting thus bypassing first-pass liver metabolism. Following lymphatic delivery, ST-65 undergoes slow release into the circulation where it is hydrolyzed by plasma esterases to provide the potent individual mTOR and MEK inhibitor ligands, AZD 8055 and ST-68, respectively. An added advantage is that the intact prodrug (ST-65) itself displays potent mTOR and MEK inhibition in the low nanomolar range (Table 13), thus functioning as a potent bifunctional mTOR/MEK inhibitor.

TABLE 13

In vitro Inhibition data for ST-65 and active mTOR and MEK Inhibitors

| Compound | cLogP | IC$_{50}$ (nM) mTOR1 | MEK1 |
|---|---|---|---|
| AZD 8055 | 4.42 | 1.07 ± 0.12 | N/A |
| ST-68 | 3.76 | N/A | 72.3 ± 1.9 |
| ST-65 | 7.50 | 40.5 ± 2.2 | 83.2 ± 4.5 |

Design of mTOR/MEK Inhibitor Prodrug ST-65

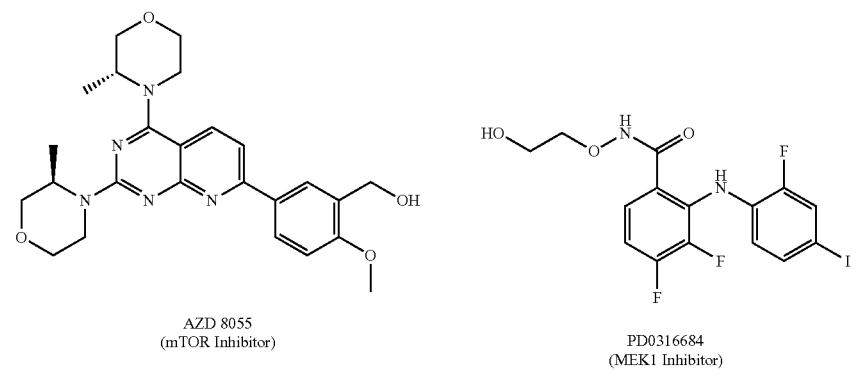 [SMILES: COc1ccc(-c2ccc3c(N4CCOC[C@H]4C)nc(N4CCOC[C@H]4C)nc3n2)cc1CO ; O=C(NOCCO)c1ccc(F)c(F)c1Nc1ccc(I)cc1F]

AZD 8055 (mTOR Inhibitor)

PD0316684 (MEK1 Inhibitor)

In vivo Lymph targeting and mTOR/MEK Inhibition of Prodrug ST-65

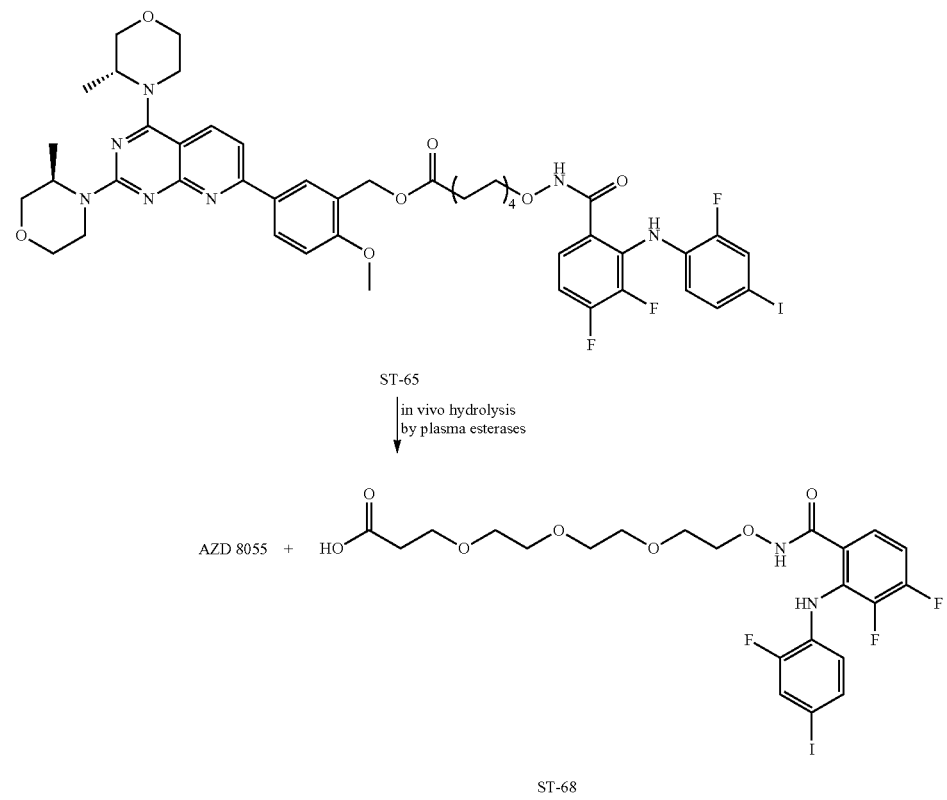

ST-65 in vivo hydrolysis by plasma esterases

AZD 8055 + ST-68

Additional nonlimiting compounds of the present invention are provided in Table 14. The compounds, and other compounds disclosed herein are prepared using the synthetic procedures disclosed in U.S. Pat. No. 9,611,258 and PCT/US2017/040866, each incorporated herein by reference.

TABLE 14

| Compound | Structure | IC$_{50}$ (nM) | | | | |
|---|---|---|---|---|---|---|
| | | PI3Kα | PI3Kβ | PI3Kγ | PI3Kδ | MEK1 |
| ST-5-31 | 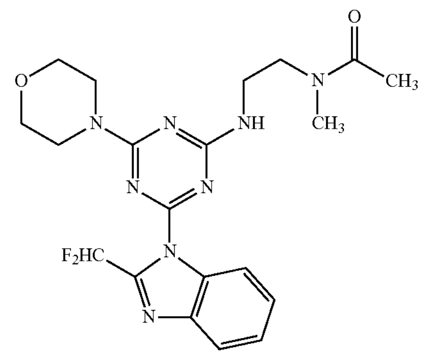 [SMILES: CC(=O)N(C)CCNc1nc(N2CCOCC2)nc(-n2c(C(F)F)nc3ccccc32)n1] | 10.3 ± 1.0 | 404 ± 63 | 55.2 ± 11.5 | 11.7 ± 2.2 | n/a |
| ST-5-32 | 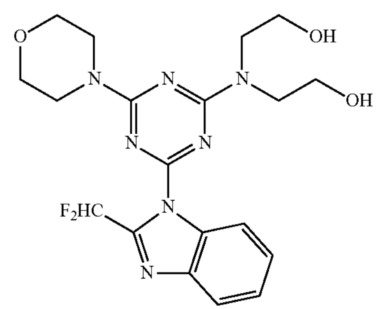 [SMILES: OCCN(CCO)c1nc(N2CCOCC2)nc(-n2c(C(F)F)nc3ccccc32)n1] | 3.74 ± 1.0 | 74 ± 5.7 | 14.6 ± 1.4 | 9.9 ± 0.4 | n/a |

TABLE 14-continued

| Compound | Structure | IC$_{50}$ (nM) | | | | |
|---|---|---|---|---|---|---|
| | | PI3Kα | PI3Kβ | PI3Kγ | PI3Kδ | MEK1 |
| ST-5-44 | 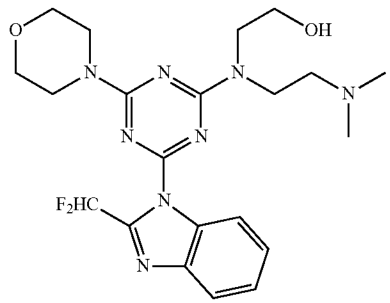 [SMILES: CN(C)CCN(CCO)c1nc(N2CCOCC2)nc(-n2c(C(F)F)nc3ccccc32)n1] | 148 ± 22 | 627 ± 174 | 869 ± 11 | 46.7 ± 3.3 | n/a |
| ST-6-01 | 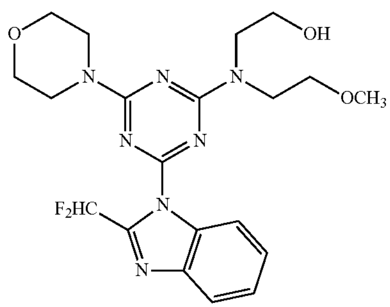 [SMILES: COCCN(CCO)c1nc(N2CCOCC2)nc(-n2c(C(F)F)nc3ccccc32)n1] | 5.1 ± 1.1 | 136 ± 6.4 | 30.7 ± 0.9 | 8.9 ± 0.5 | n/a |
| ST-5-50 | 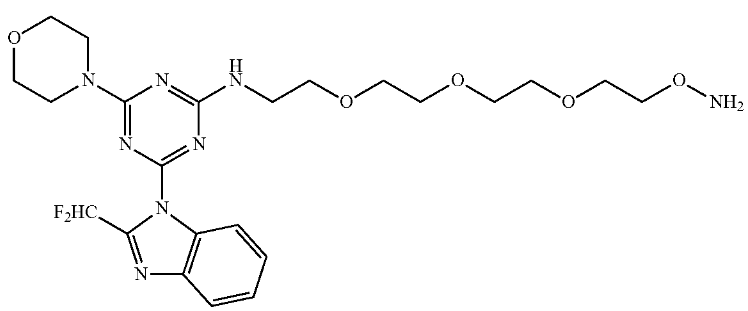 [SMILES: NOCCOCCOCCOCCNc1nc(N2CCOCC2)nc(-n2c(C(F)F)nc3ccccc32)n1] | 89.3 ± 9.5 | 1867 ± 245 | 502 ± 20 | 12.6 ± 1.0 | n/a |

TABLE 14-continued

| Compound | Structure | IC$_{50}$ (nM) | | | | |
|---|---|---|---|---|---|---|
| | | PI3Kα | PI3Kβ | PI3Kγ | PI3Kδ | MEK1 |
| ST-5-46 | 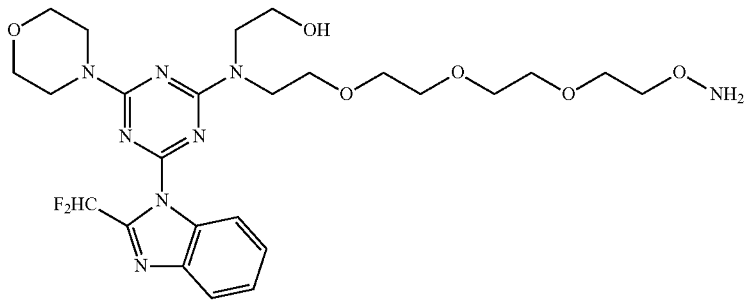 [SMILES: NOCCOCCOCCOCCN(CCO)c1nc(N2CCOCC2)nc(-n2c(C(F)F)nc3ccccc32)n1] | 10.9 ± 0.7 | 1085 ± 143 | 137 ± 21 | 8.6 ± 1.2 | n/a |
| ST-6-02 | 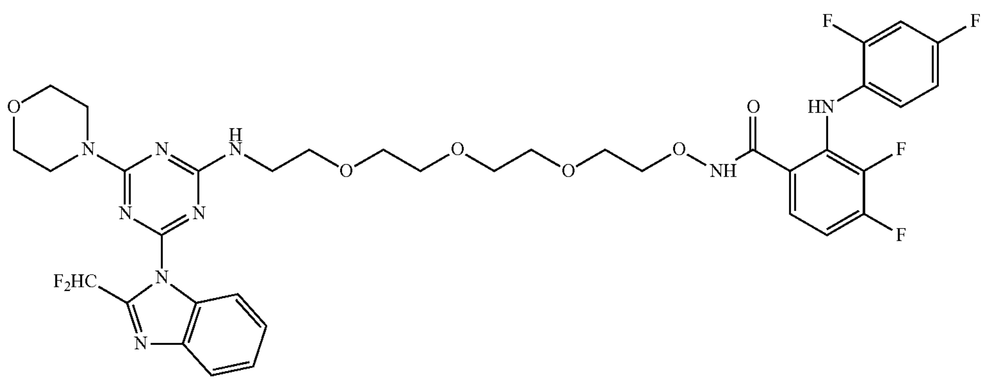 [SMILES: O=C(NOCCOCCOCCOCCNc1nc(N2CCOCC2)nc(-n2c(C(F)F)nc3ccccc32)n1)c1ccc(F)c(F)c1Nc1ccc(F)cc1F] | 130 ± 13 | 1537 ± 188 | 2745 ± 485 | 236 ± 29 | 124 ± 11 |

TABLE 14-continued
| Compound | Structure | IC$_{50}$ (nM) | | | | |
|---|---|---|---|---|---|---|
| | | PI3Kα | PI3Kβ | PI3Kγ | PI3Kδ | MEK1 |
| ST-5-47 | 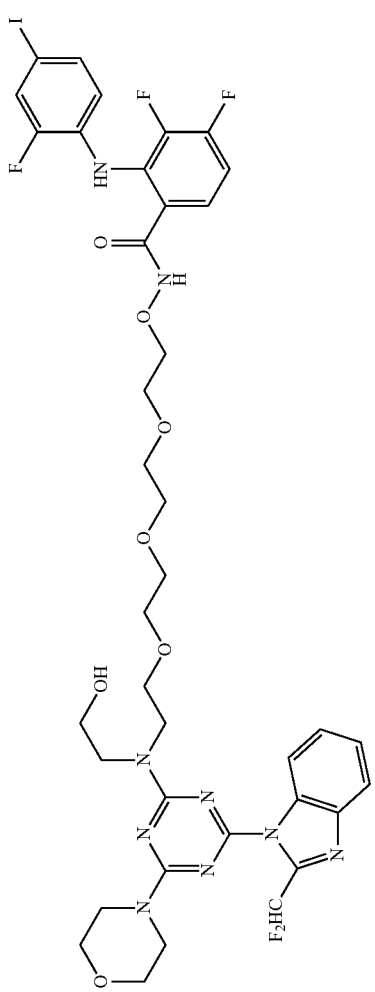 | 107 ± 21 | 3880 ± 725 | 2567 ± 364 | 137 ± 7 | 352 ± 2 |

Figure 7:
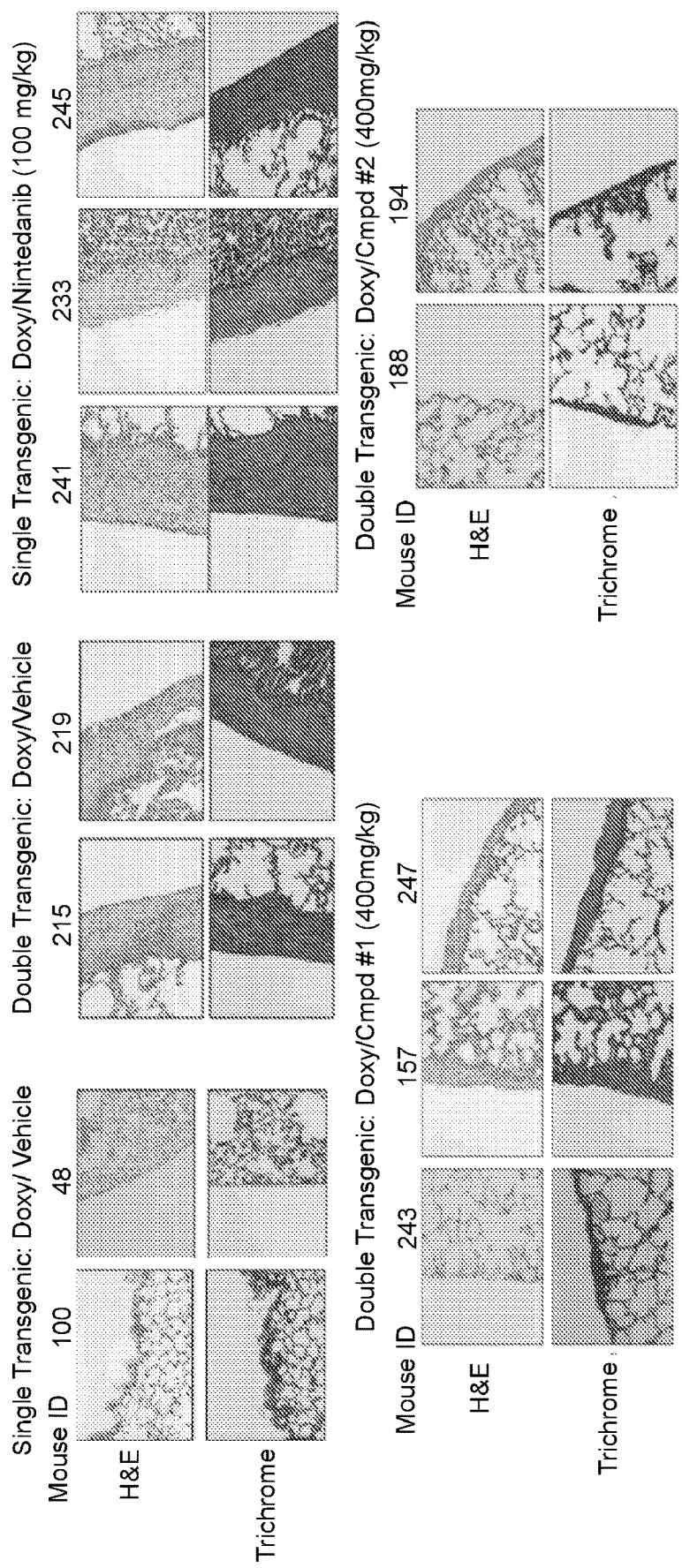
FIG. 7 contains histological sections of mouse lungs with idiopathic lung fibrosis treated for several weeks of a daily dose of ST-182.

Treatment of inflammatory-mediated fibrotic diseases were also evaluated using a doxycycline (Dox)-inducible transforming growth factor-α (TGFα)-transgenic mouse model of idiopathic pulmonary fibrosis (IPF) expressing lung-epithelial specific TGFα following Dox administration. ST-168 (n=7) or ST-182 (n=5) (400 mg/kg, PO) was administered in mice with established fibrotic burden for up to 4 weeks after 5 weeks of Dox induction with continued Dox administration during treatment. Weekly lung micro-CT exams were used for assessment of fibrotic burden. Nintenadib (n=5) (100 mg/kg) was also evaluated for comparison. Lung tissue was examined microscopy in a subset of animals at the conclusion of the study. Mouse chest CT scans revealed significant presence of parenchymal lung fibrosis and pleural thickening present at the time of treatment initiation. Both ST-168 and ST-182 were demonstrated to have strong activity for reversal of lung fibroproliferative disease and reversal of pleural thickness at the 3 week follow up CT scan. As shown in lung histopathology sections in FIG. 7, these compounds were able to significantly reverse fibrosis in this IPF mouse model.

Figure 8:
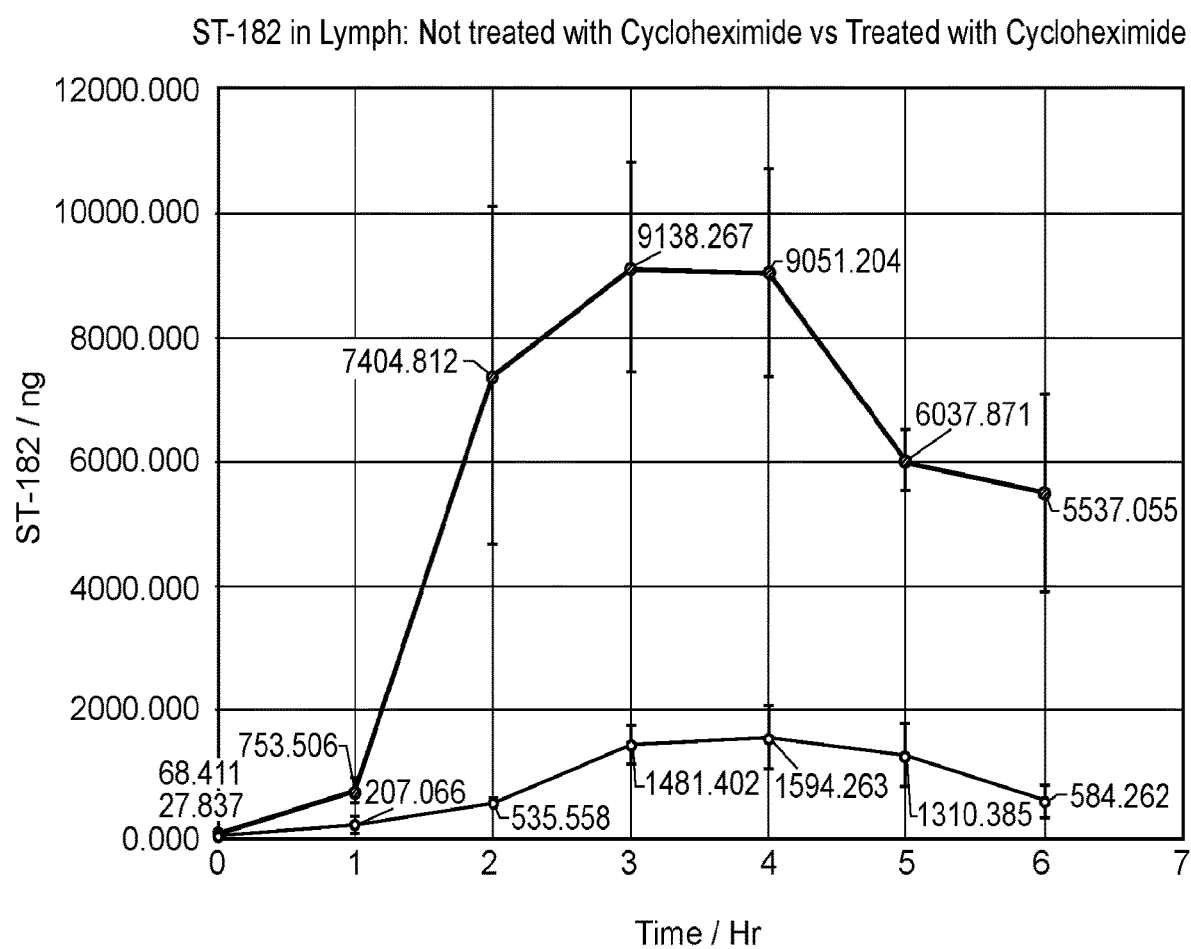
FIG. 8 contains a plot showing the lymphatic uptake of ST-182 in a rat and the reduced uptake following chemical inhibition of the lymphatic transport system.

Evaluation of compound mechanism for lymphatic uptake was also undertaken. A messenteric lymph duct cannulation rat model was used to evaluate the transport process involved in the movement of ST-182 from the intestinal millieu to the mesenteric lymphatics. The amount and rate of transport from the intestine via the lymphatic system was quantified using LC-MS/MS and is shown in FIG. 8 under two different conditions following administration of 50 mg/kg of ST-182 into the duodenum over a one hour infusion period. The upper curve revealed the time course of ST-182 in the lymphatic fluid which reached approximately 9,000 ng levels (approximately 15-30 µM). Pretreatment of animals with cycloheximide, a chemical inhibitor of the lymphatic active transport system, significantly reduced the transport of the drug into the lymphatics. This study shows that the lymphatic system recognizes ST-182 for transport and thus actively transported it into the lymphatic system. This data supports attachment of mEG moieties to compounds to improve lymphatic avidity thus assisting with lymphatic transport and uptake.

The present invention includes (a) development of individual mTOR, PI3K, and MEK inhibitors that are chemically modified with conjugating linkers to maintain high-binding affinity towards their respective enzyme targets; and (b) conjugation of these chemical entities in a final synthetic step to provide the prototype single chemical entity functional inhibitor compounds. The present compounds are capable of a lymph-directed therapeutic activity. This strategy could also be used to link alternate MEK inhibitors such as Trametinib, Selumetinib, Pimersertib, SMK-17, for example. Other MEK inhibitors are disclosed in Chapter 8, FIGS. 8.10 and 8.11: Sebolt-Leopold, et al. (2009), *Road to PD0325901 and Beyond: The MEK Inhibitor Quest*, in *Kinase Inhibitor Drugs* (Eds. R. Li and J. A. Stafford), John Wiley & Sons, Inc., Hoboken, N.J., USA.

Alternate PI3K inhibitors include, for example, GDC 0941, GDC 0980, BKM-120, BEZ235, PIK-90, and Duvelisib.

Alternate mTOR inhibitors include, for example, rapamycin, AZD8055, KU0063794, Torkinib (PP242), and Voxtalisib.

The present invention therefore provides mTOR and/or MEK and/or JAK and/or PI3K inhibitors, as exemplified by the present compounds, for the treatment of diseases and conditions wherein inhibition of at least one, and preferably at least two, of mTOR, MEK, JAK and PI3K has a beneficial effect. In one embodiment, the present invention relates to a method of treating an individual suffering from a disease or condition wherein inhibition of mTOR or MEK or JAK or PI3K, and preferably all, provides a benefit comprising administering a therapeutically effective amount of a present compound to an individual in need thereof. It is envisioned that a present compound exhibits a greater activity against KRAS mutant tumors.

The method of the present invention can be accomplished by administering a present compound as the neat compound or as a pharmaceutical composition. Administration of a pharmaceutical composition, or neat present compound, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a present compound and, optionally, a second therapeutic agent useful in the treatment of diseases and conditions wherein inhibition of mTOR and/or MEK and/or JAK and/or PI3K provides a benefit, packaged separately or together, and an insert having instructions for using these active agents.

In many embodiments, a present compound is administered in conjunction with a second therapeutic agent useful in the treatment of a disease or condition wherein inhibition of one or more of mTOR, MEK, JAK and PI3K provides a benefit. The second therapeutic agent is different from the present functional compound. A present compound and the second therapeutic agent can be administered simultaneously or sequentially to achieve the desired effect. In addition, the present compound and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A present compound and the second therapeutic agent can be administered together as a single-unit dose or separately as multi-unit doses, wherein the present compound is administered before the second therapeutic agent or vice versa. One or more dose of the present compound and/or one or more dose of the second therapeutic agent can be administered. The present compounds therefore can be used in conjunction with one or more second therapeutic agents, for example, but not limited to, anticancer agents.

The diseases and conditions that can be treated in accordance to the invention include, for example, cancers. A variety of cancers can be treated including, but not limited to: carcinomas, including bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the MEK/PI3K inhibitors of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, non-small cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, myelofibrosis, myeloid malignancy including acute myelogenous leukemia (AML), myelodysplastic syndrome (MDS), chronic myeloid leukemia (CML), and Kaposi's sarcoma.

The present compounds are particularly useful in the treatment of pancreatic and colorectal cancers, and tumor metastatic disease Route of administration also can be by direct intraocular injection of the compounds for tumor treatments of the eye, for example including uveal melanoma and retinoblastoma. The present inhibitors also can be delivered topically, orally, or intravenously, or by intraocular implant, to improve ocular drug bioavailability. As cell signaling pathways can have significant "cross-talk" and thus many different molecular interactions with other biological pathways, targeting the JAK/STAT, PI3K/Akt/mTOR and Raf/MEK/ERK pathways can be beneficial for eye diseases, including glaucoma, cataract, age-related macular degeneration, amblyopia, and diabetic retinopathy.

Additional diseases and conditions, including cancers, inflammatory diseases, allergic diseases, inflammatory bowel diseases, vasculitis, Behcet's syndrome, psoriasis, inflammatory dermatoses, asthma, respiratory allergic diseases, autoimmune diseases, graft rejection, fever, cardiovascular disorders, cerebrovascular disorders, fibrosis, connective tissue disease, sarcoidosis, genital and reproductive disorders, gastrointestinal disorders, neurologic disorders, sleep disorders, pain, renal disorders, and infectious diseases, including HIV, chronic pain including neuropathic pain (pain caused by damage to or malfunction of the nerves themselves) and nociceptive pain (nociceptors are receptors in the nervous system that activate during injury) and chronic pain associated with clinical diagnosis as for example, fibromyalgia, inflammation, musculoskeletal malfunction that can be treated by administration of a present JAK and/or mTOR and/or MEK and/or PI3K inhibitor are disclosed in U.S. Patent Publication No. 2011/0053907; U.S. Pat. No. 7,897,792; U.S. Patent Publication No. 2011/0009405, and U.S. Patent Publication No. 2010/0249099, each incorporated herein by reference in its entirety.

In the present method, a therapeutically effective amount of one or more of a present inhibitor, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A present compound can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present compound is administered in an effective amount to achieve its intended purpose. The exact formulation, route of administration, and dosage is determined by an individual physician in view of the diagnosed condition or disease. Dosage amount and interval can be adjusted individually to provide levels of a present compound that is sufficient to maintain therapeutic effects.

Toxicity and therapeutic efficacy of the present compounds can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g., inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present compound required for use in therapy varies with the nature of the condition being treated, the length of time that activity is desired, and the age and the condition of the patient, and ultimately is determined by the attendant physician. Dosage amounts and intervals can be adjusted individually to provide plasma levels of the functional inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days' rest, and another five daily doses (5/2/5); or, any dose regimen determined to be appropriate for the circumstance.

A present compound used in a method of the present invention can be administered in an amount of about 0.005 to about 500 milligrams per dose, about 0.05 to about 250 milligrams per dose, or about 0.5 to about 100 milligrams per dose. For example, a present compound can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a present inhibitor, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

In the treatment of a cancer, a present compound can be administered with a chemotherapeutic agent and/or radiation.

Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, an inhibitor of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof.

Examples of chemotherapeutic agents useful in a method of the present invention are listed in the following table.

| Alkylating agents |
| --- |
| Nitrogen mustards |
| mechlorethamine |
| cyclophosphamide |
| ifosfamide |
| melphalan |
| chlorambucil |
| uracil mustard |
| temozolomide |

| Nitrosoureas |
| --- |
| carmustine (BCNU) |
| lomustine (CCNU) |
| semustine (methyl-CCNU) |
| chlormethine |
| streptozocin |
| Ethylenimine/Methyl-melamine |
| triethylenemelamine (TEM) |
| triethylene thiophosphoramide (thiotepa) |
| Hexamethylmelamine (HMM, altretamine) |
| Alkyl sulfonates |
| busulfan |
| pipobroman |
| Triazines |
| dacarbazine (DTIC) |
| Antimetabolites |
| Folic Acid analogs |
| methotrexate |
| trimetrexate |
| pemetrexed (Multi-targeted antifolate) |
| Pyrimidine analogs |
| 5-fluorouracil |
| fluorodeoxyuridine |
| gemcitabine |
| cytosine arabinoside (AraC, cytarabine) |
| 5-azacytidine |
| 2,2'-difluorodeoxy-cytidine |
| floxuridine |
| pentostatine |
| Purine analogs |
| 6-mercaptopurine |
| 6-thioguanine |
| azathioprine |
| 2'-deoxycoformycin (pentostatin) |
| erythrohydroxynonyl-adenine (EHNA) |
| fludarabine phosphate |
| 2-chlorodeoxyadenosine (cladribine, 2-CdA) |
| Type I Topoisomerase Inhibitors |
| camptothecin |
| topotecan |
| irinotecan |
| Biological response modifiers |
| G-CSF |
| GM-CSF |
| Differentiation Agents |
| retinoic acid derivatives |
| Hormones and antagonists |
| Adrenocorticosteroids/antagonists |
| prednisone and equivalents |
| dexamethasone |
| ainoglutethimide |
| Progestins |
| hydroxyprogesterone caproate |
| medroxyprogesterone acetate |
| megestrol acetate |
| Estrogens |
| diethylstilbestrol |
| ethynyl estradiol/equivalents |
| Antiestrogen |
| tamoxifen |
| Androgens |
| testosterone propionate |
| fluoxymesterone/equivalents |
| Antiandrogens |
| flutamide |
| gonadotropin-releasing |
| hormone analogs |
| leuprolide |
| Natural products |
| Antimitotic drugs |
| Taxanes |
| paclitaxel |
| Vinca alkaloids |
| vinblastine (VLB) |
| vincristine |
| vinorelbine |
| vindesine |
| Taxotere ® (docetaxel) |
| estramustine |
| estramustine phosphate |
| Epipodophylotoxins |
| etoposide |
| teniposide |
| Antibiotics |
| actimomycin D |
| daunomycin (rubidomycin) |
| doxorubicin (adriamycin) |
| mitoxantroneidarubicin |
| bleomycin |
| splicamycin (mithramycin) |
| mitromycin-C |
| dactinomycin |
| aphidicolin |
| epirubicin |
| idarubicin |
| daunorubicin |
| mithramycin |
| deoxy co-formycin |
| Enzymes |
| L-asparaginase |
| L-arginase |
| Radiosensitizers |
| metronidazole |
| misonidazole |
| desmethylmisonidazole |
| pimonidazole |
| etanidazole |
| nimorazole |
| RSU 1069 |
| EO9 |
| RB 6145 |
| Nonsteroidal antiandrogens |
| SR4233 |
| flutamide |
| nicotinamide |
| 5-bromodeozyuridine |
| 5-iododeoxyuridine |
| bromodeoxycytidine |
| Miscellaneous agents |
| Platinum coordination complexes |
| cisplatin |
| carboplatin |
| oxaliplatin |
| anthracenedione |
| mitoxantrone |
| Substituted urea |
| hydroxyurea |
| Methylhydrazine derivatives |
| N-methylhydrazine (MIH) |
| procarbazine |

| Adrenocortical suppressant |
| --- |
| mitotane (o,p'-DDD)<br>ainoglutethimide |

| Cytokines |
| --- |
| interferon (α, β, γ)<br>interleukin-2 |

| Photosensitizers |
| --- |
| hematoporphyrin derivatives<br>PHOTOFRIN ®<br>benzoporphyrin derivatives<br>Npe6<br>tin etioporphyrin (SnET2)<br>pheoboride-a<br>bacteriochlorophyll-a<br>naphthalocyanines<br>phthalocyanines<br>zinc phthalocyanines |

| Radiation |
| --- |
| X-ray<br>ultraviolet light<br>gamma radiation<br>visible light<br>infrared radiation<br>microwave radiation |

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274:2009) estramustine, nocodazole, MAP4, and the like. Examples of such agents are also described in Bulinski (1997) *J. Cell Sci.* 110:3055 3064; Panda (1997) *Proc. Natl. Acad. Sci. USA* 94:10560-10564; Muhlradt (1997) *Cancer Res.* 57:3344-3346; Nicolaou (1997) *Nature* 397:268-272; Vasquez (1997) *Mol. Biol. Cell.* 8:973-985; and Panda (1996) *J. Biol. Chem.* 271:29807-29812.

Cytostatic agents that may be used include, but are not limited to, hormones and steroids (including synthetic analogs): 17-α-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutamide, toremifene, zoladex.

Other cytostatic agents are antiangiogenics, such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, PI3 inhibitors, Src kinase inhibitors, and PDGF inhibitors.

Compounds could also be administered in combination with opioids or cannabinoids, NSAIDS, steroids for chronic pain relief. Additional second therapeutic agents that can be administered with a present inhibitor of the present invention are well known in the art, for example as disclosed in U.S. Patent Publication 2011/0053907; and U.S. Patent Publication No. 2011/0009405, and U.S. Patent Publication No. 2010/0249099, each incorporated herein by reference in its entirety.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of present compounds.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the present compound is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present compound. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present compound.

When a therapeutically effective amount of a present compound is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

The present compounds can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present inhibitor to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present inhibitor can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present inhibitor can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present inhibitor also can be formulated in rectal compositions, such as suppositories or retention enemas, e.g., containing conventional suppository bases. In addition to the formulations described previously, the present inhibitor also can be formulated as a depot preparation. Such long-acting formulations can be administered by implantation (for example, subcutaneously or intramuscularly) or by intramuscular injection. Thus, for example, the present inhibitors can be formulated with suitable polymeric or hydrophobic materials (for example, as an emulsion in an acceptable oil) or ion exchange resins.

In particular, the present inhibitors can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The present compounds also can be injected parenterally, for example, intravenously, intramuscularly, subcutaneously, or intracoronarily. For parenteral administration, the inhibitors are best used in the form of a sterile aqueous solution which can contain other substances, for example, salts or monosaccharides, such as mannitol or glucose, to make the solution isotonic with blood. Compounds could also be administered using an inhaler as a spray to reach the lung tissue or by administration as a nasal spray.

A present inhibitor and the second therapeutic agent can be administered together as a single-unit dose or separately as multi-unit doses, wherein the inhibitor is administered before the second therapeutic agent or vice versa. It is envisioned that one or more dose of a inhibitor and/or one or more dose of a second therapeutic agent can be administered.

In one embodiment, a present inhibitor and a second therapeutic agent are administered simultaneously. In related embodiments, a present inhibitor and second therapeutic agent are administered from a single composition or from separate compositions. In a further embodiment, a present inhibitor and second therapeutic agent are administered sequentially.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a present functional compound and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

Prior mTOR, MEK, JAK and PI3K inhibitors possessed properties that hindered their development as therapeutic agents. In accordance with an important feature of the invention, present compounds were synthesized and evaluated as inhibitors for mTOR and/or MEK and/or JAK and/or PI3K acting through the lymphatic system.

REFERENCES

Anighoro, A., J. Bajorath and G. Rastelli (2014). "Polypharmacology: challenges and opportunities in drug discovery." *J Med Chem* 57(19): 7874-7887.

Bakhru, S. H., S. Furtado, A. P. Morello and E. Mathiowitz (2013). "Oral delivery of proteins by biodegradable nanoparticles." *Adv Drug Deliv Rev* 65(6): 811-821.

Caliph, S. M., W. N. Charman and C. J. Porter (2000). "Effect of short-, medium-, and long-chain fatty acid-based vehicles on the absolute oral bioavailability and intestinal lymphatic transport of halofantrine and assessment of mass balance in lymph-cannulated and non-cannulated rats." *J Pharm Sci* 89(8): 1073-1084.

Charman, W. N. a. S., V. J. (1986). "Estimating the maximum potential for intestinal lymphatic transport of lipophilic drug molecules." *Int. J. Pharm* 34: 175-178.

Choo, E. F., J. Boggs, C. Zhu, J. W. Lubach, N. D. Catron, G. Jenkins, A. J. Souers and R. Voorman (2014). "The role of lymphatic transport on the systemic bioavailability of the Bcl-2 protein family inhibitors navitoclax (ABT-263) and ABT-199." *Drug Metab Dispos* 42(2): 207-212.

Faisal, W., T. Ruane-O'Hora, C. M. O'Driscoll and B. T. Griffin (2013). "A novel lipid-based solid dispersion for enhancing oral bioavailability of Lycopene—in vivo evaluation using a pig model." *Int J Pharm* 453(2): 307-314.

Florence, A. T. (2005). "Nanoparticle uptake by the oral route: Fulfilling its potential?" *Drug Discov Today Technol* 2(1): 75-81.

Gershkovich, P., J. Fanous, B. Qadri, A. Yacovan, S. Amselem and A. Hoffman (2009). "The role of molecular physicochemical properties and apolipoproteins in association of drugs with triglyceride-rich lipoproteins: in-silico prediction of uptake by chylomicrons." *J Pharm Pharmacol* 61(1): 31-39.

Gershkovich, P. and A. Hoffman (2005). "Uptake of lipophilic drugs by plasma derived isolated chylomicrons: linear correlation with intestinal lymphatic bioavailability." *Eur J Pharm Sci* 26(5): 394-404.

Han, S., T. Quach, L. Hu, A. Wahab, W. N. Charman, V. J. Stella, N. L. Trevaskis, J. S. Simpson and C. J. Porter (2014). "Targeted delivery of a model immunomodulator to the lymphatic system: comparison of alkyl ester versus triglyceride mimetic lipid prodrug strategies." *J Control Release* 177: 1-10.

Hauss, D. J., S. E. Fogal, J. V. Ficorilli, C. A. Price, T. Roy, A. A. Jayaraj and J. J. Keirns (1998). "Lipid-based delivery systems for improving the bioavailability and lymphatic transport of a poorly water-soluble LTB4 inhibitor." *J Pharm Sci* 87(2): 164-169.

Holm, R. and J. Hoest (2004). "Successful in silico predicting of intestinal lymphatic transfer." *Int J Pharm* 272(1-2): 189-193.

Hopkins, A. L., G. M. Keseru, P. D. Leeson, D. C. Rees and C. H. Reynolds (2014). "The role of ligand efficiency metrics in drug discovery." *Nat Rev Drug Discov* 13(2): 105-121.

Hu, L., T. Quach, S. Han, S. F. Lim, P. Yadav, D. Senyschyn, N. L. Trevaskis, J. S. Simpson and C. J. Porter (2016). "Glyceride-Mimetic Prodrugs Incorporating Self-Immolative Spacers Promote Lymphatic Transport, Avoid First-Pass Metabolism, and Enhance Oral Bioavailability." *Angew Chem Int Ed Enql* 55(44): 13700-13705.

Karaman, S. and M. Detmar (2014). "Mechanisms of lymphatic metastasis." *J Clin Invest* 124(3): 922-928.

Khoo, S. M., D. M. Shackleford, C. J. Porter, G. A. Edwards and W. N. Charman (2003). "Intestinal lymphatic transport of halofantrine occurs after oral administration of a unit-dose lipid-based formulation to fasted dogs." *Pharm Res* 20(9): 1460-1465. Kunisawa, J., Y. Kurashima and H. Kiyono (2012). "Gut-associated lymphoid tissues for the development of oral vaccines." *Adv Drug Deliv Rev* 64(6): 523-530.

Lambert, D. M. (2000). "Rationale and applications of lipids as prodrug carriers." *Eur J Pharm Sci* 11 Suppl 2: S15-27.

Lawless, E., B. T. Griffin, A. O'Mahony and C. M. O'Driscoll (2015). "Exploring the impact of drug properties on the extent of intestinal lymphatic transport—in vitro and in vivo studies." *Pharm Res* 32(5): 1817-1829.

Leeson, P. D. and B. Springthorpe (2007). "The influence of drug-like concepts on decision-making in medicinal chemistry." *Nat Rev Drug Discov* 6(11): 881-890.

Lindenberg, M., S. Kopp and J. B. Dressman (2004). "Classification of orally administered drugs on the World Health Organization Model list of Essential Medicines according to the biopharmaceutics classification system." *Eur J Pharm Biopharm* 58(2): 265-278.

Lipinski, C. A., F. Lombardo, B. W. Dominy and P. J. Feeney (2001). "Experimental and computational approaches to estimate solubility and permeability in drug discovery and development settings." *Adv Drug Deliv Rev* 46(1-3): 3-26.

Lu, Y., Y. Qiu, J. Qi, M. Feng, D. Ju and W. Wu (2015). "Biomimetic reassembled chylomicrons as novel association model for the prediction of lymphatic transportation of highly lipophilic drugs via the oral route." *Int J Pharm* 483(1-2): 69-76.

Ma, B.-L., Yang, Y, Dai, Y, Li Q, Lin Ge and Ma Y-M (2017). "Polyethylene glycol 400 (PEG400) affects the systemic exposure of oral drugs based on multiple mechanisms: taking berberine as an example." *RSC Adv* 7: 2435-2442.

Myers, R. A. a. S., V. J. (1992). "Factors affecting the lymphatic transport of penclomedine (NSC-338720), a lipophilic cytoxic drug-comparison to DDT and hexachlorobenzene." *Int. J. Pharm.* 80: 51-62.

O'Driscoll, C. M. (2002). "Lipid-based formulations for intestinal lymphatic delivery." *Eur J Pharm Sci* 15(5): 405-415.

Oprea, T. I., A. M. Davis, S. J. Teague and P. D. Leeson (2001). "Is there a difference between leads and drugs? A historical perspective." *J Chem Inf Comput Sci* 41(5): 1308-1315.

Paliwal, R., S. R. Paliwal, N. Mishra, A. Mehta and S. P. Vyas (2009). "Engineered chylomicron mimicking carrier emulsome for lymph targeted oral delivery of methotrexate." *Int J Pharm* 380(1-2): 181-188.

Porter, C. J., S. A. Charman, A. J. Humberstone and W. N. Charman (1996). "Lymphatic transport of halofantrine in the conscious rat when administered as either the free base or the hydrochloride salt: effect of lipid class and lipid vehicle dispersion." *J Pharm Sci* 85(4): 357-361.

Rautio, J., H. Kumpulainen, T. Heimbach, R. Oliyai, D. Oh, T. Jarvinen and J. Savolainen (2008). "Prodrugs: design and clinical applications." *Nat Rev Drug Discov* 7(3): 255-270.

Reddy, A. S. and S. Zhang (2013). "Polypharmacology: drug discovery for the future." *Expert Rev Clin Pharmacol* 6(1): 41-47.

Shackleford, D. M., W. A. Faassen, N. Houwing, H. Lass, G. A. Edwards, C. J. Porter and W. N. Charman (2003). "Contribution of lymphatically transported testosterone undecanoate to the systemic exposure of testosterone after oral administration of two andriol formulations in conscious lymph duct-cannulated dogs." *J Pharmacol Exp Ther* 306(3): 925-933.

Sugihara, J., S. Furuuchi, H. Ando, K. Takashima and S. Harigaya (1988). "Studies on intestinal lymphatic absorption of drugs. II. Glyceride prodrugs for improving lymphatic absorption of naproxen and nicotinic acid." *J Pharmacobiodyn* 11(8): 555-562.

Sugihara, J., S. Furuuchi, K. Nakano and S. Harigaya (1988). "Studies on intestinal lymphatic absorption of drugs. I. Lymphatic absorption of alkyl ester derivatives and alpha-monoglyceride derivatives of drugs." *J Pharmacobiodyn* 11(5): 369-376.

Trevaskis, N. L., S. M. Caliph, G. Nguyen, P. Tso, W. N. Charman and C. J. Porter (2013). "A mouse model to evaluate the impact of species, sex, and lipid load on lymphatic drug transport." *Pharm Res* 30(12): 3254-3270.

Trevaskis, N. L., W. N. Charman and C. J. Porter (2008). "Lipid-based delivery systems and intestinal lymphatic drug transport: a mechanistic update." *Adv Drug Deliv Rev* 60(6): 702-716.

Trevaskis, N. L., L. M. Kaminskas and C. J. Porter (2015). "From sewer to saviour—targeting the lymphatic system to promote drug exposure and activity." *Nat Rev Drug Discov* 14(11): 781-803.

Trevaskis, N. L., D. M. Shackleford, W. N. Charman, G. A. Edwards, A. Gardin, S. Appel-Dingemanse, O. Kretz, B. Galli and C. J. Porter (2009). "Intestinal lymphatic transport enhances the post-prandial oral bioavailability of a novel cannabinoid receptor agonist via avoidance of first-pass metabolism." *Pharm Res* 26(6): 1486-1495.

Trevaskis, N. L., R. M. Shanker, W. N. Charman and C. J. Porter (2010). "The mechanism of lymphatic access of two cholesteryl ester transfer protein inhibitors (CP524, 515 and CP532,623) and evaluation of their impact on lymph lipoprotein profiles." *Pharm Res* 27(9): 1949-1964.

Turecek, P. L., M. J. Bossard, F. Schoetens and I. A. Ivens (2016). "PEGylation of Biopharmaceuticals: A Review of Chemistry and Nonclinical Safety Information of Approved Drugs." *J Pharm Sci* 105(2): 460-475.

van Witteloostuijn, S. B., S. L. Pedersen and K. J. Jensen (2016). "Half-Life Extension of Biopharmaceuticals using Chemical Methods: Alternatives to PEGylation." *ChemMedChem* 11(22): 2474-2495.

Yanez, J. A., S. W. Wang, I. W. Knemeyer, M. A. Wirth and K. B. Alton (2011). "Intestinal lymphatic transport for drug delivery." *Adv Drug Deliv Rev* 63(10-11): 923-942.

What is claimed:

1. An MEK inhibitor selected from the group consisting of

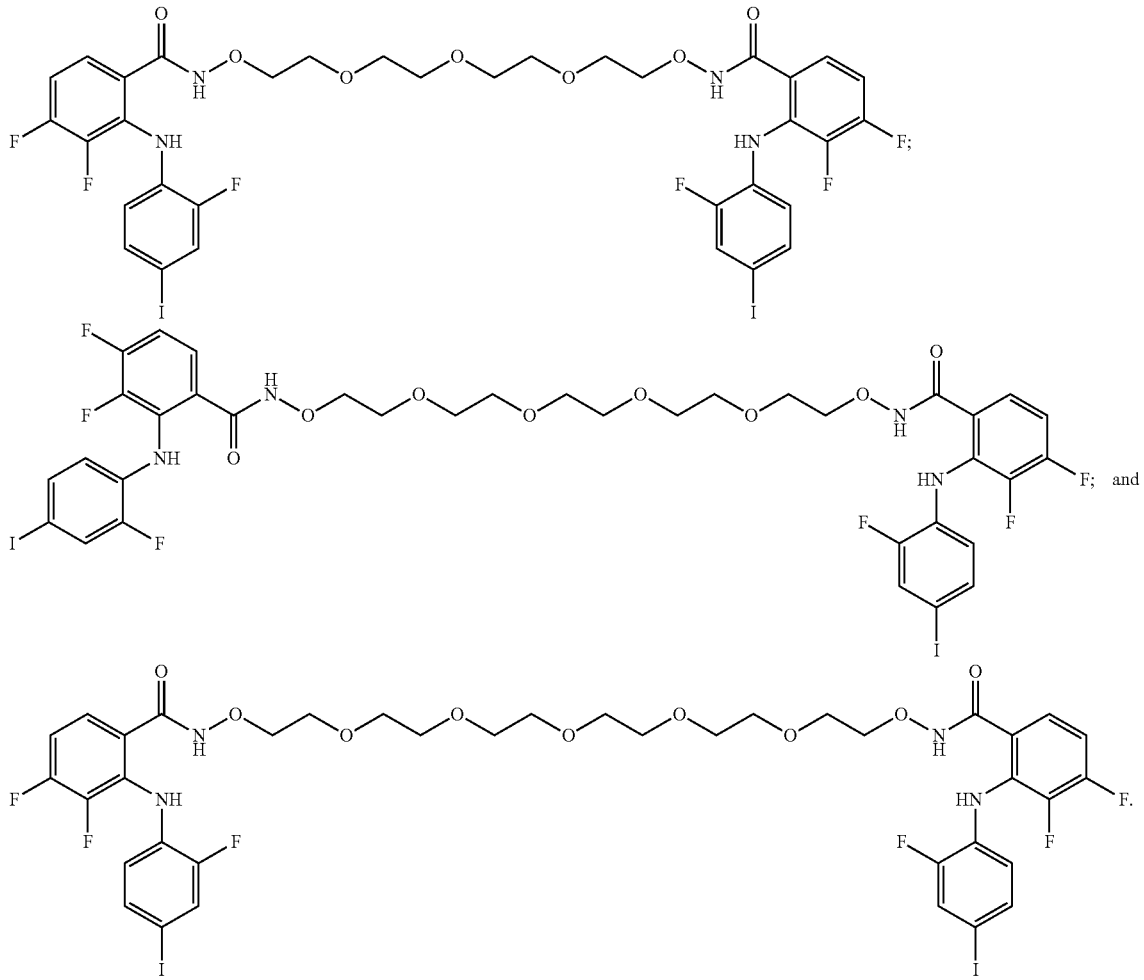

2. A method of treating a disease or condition wherein inhibition of MEK provides a benefit comprising administering a therapeutically effective amount of a compound of claim 1 to an individual in need thereof.

3. The method of claim 2 wherein the disease or condition is selected from the group consisting of a cancer;

a pulmonary disease, a fibrotic disorder, an inflammatory disorder, chronic pain, and a neurodegenerative disease; and a chronic obstructive pulmonary disease, IPF, an autoimmune disease, multiple sclerosis, and Alzheimer's disease.

* * * * *